(12) United States Patent
Rezvani et al.

(10) Patent No.: US 11,344,578 B2
(45) Date of Patent: May 31, 2022

(54) IMMUNE CELLS EXPRESSING ENGINEERED ANTIGEN RECEPTORS

(71) Applicant: Board of Regents, The University of Texas System, Austin, TX (US)

(72) Inventors: Katy Rezvani, Houston, TX (US); Elizabeth J. Shpall, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 296 days.

(21) Appl. No.: 16/606,700

(22) PCT Filed: Apr. 19, 2018

(86) PCT No.: PCT/US2018/028418
§ 371 (c)(1),
(2) Date: Oct. 18, 2019

(87) PCT Pub. No.: WO2018/195339
PCT Pub. Date: Oct. 25, 2018

(65) Prior Publication Data
US 2020/0085872 A1  Mar. 19, 2020

Related U.S. Application Data

(60) Provisional application No. 62/487,248, filed on Apr. 19, 2017.

(51) Int. Cl.
| | |
|---|---|
| *A61K 35/17* | (2015.01) |
| *A61P 35/02* | (2006.01) |
| *A61K 9/00* | (2006.01) |
| *A61K 45/06* | (2006.01) |
| *C07K 14/54* | (2006.01) |
| *C07K 14/55* | (2006.01) |
| *C07K 14/725* | (2006.01) |
| *C07K 14/705* | (2006.01) |
| *C07K 16/28* | (2006.01) |
| *C07K 16/30* | (2006.01) |
| *C07K 16/32* | (2006.01) |
| *C12N 5/0783* | (2010.01) |
| *C12N 5/0775* | (2010.01) |
| *C12N 5/074* | (2010.01) |
| *C12N 9/22* | (2006.01) |
| *C12N 9/64* | (2006.01) |
| *C12N 15/11* | (2006.01) |
| *A61K 39/00* | (2006.01) |

(52) U.S. Cl.
CPC ............ *A61K 35/17* (2013.01); *A61K 9/0019* (2013.01); *A61K 45/06* (2013.01); *A61P 35/02* (2018.01); *C07K 14/54* (2013.01); *C07K 14/5443* (2013.01); *C07K 14/55* (2013.01); *C07K 14/7051* (2013.01); *C07K 14/70521* (2013.01); *C07K 16/2863* (2013.01); *C07K 16/2878* (2013.01); *C07K 16/30* (2013.01); *C07K 16/3092* (2013.01); *C07K 16/32* (2013.01); *C12N 5/0638* (2013.01); *C12N 5/0646* (2013.01); *C12N 5/0668* (2013.01); *C12N 5/0696* (2013.01); *C12N 9/22* (2013.01); *C12N 9/6472* (2013.01); *C12N 15/11* (2013.01); *C12Y 304/22062* (2013.01); *A61K 2039/5156* (2013.01); *A61K 2039/5158* (2013.01); *C07K 2319/02* (2013.01); *C07K 2319/03* (2013.01); *C07K 2319/30* (2013.01); *C07K 2319/33* (2013.01); *C12N 2310/20* (2017.05); *C12N 2506/45* (2013.01); *C12N 2510/00* (2013.01); *C12N 2800/80* (2013.01)

(58) Field of Classification Search
CPC ....................................................... A61K 35/17
See application file for complete search history.

(56) References Cited

U.S. PATENT DOCUMENTS

| | | | |
|---|---|---|---|
| 4,536,468 | A | 8/1985 | Yasui et al. |
| 4,981,784 | A | 1/1991 | Evans et al. |
| 5,164,897 | A | 11/1992 | Clark et al. |
| 5,171,671 | A | 12/1992 | Evans et al. |
| 5,342,929 | A | 8/1994 | Ernst et al. |
| 5,552,303 | A | 9/1996 | Grabstein et al. |
| 5,571,696 | A | 11/1996 | Evans et al. |
| 5,602,009 | A | 2/1997 | Evans et al. |
| 5,686,281 | A | 11/1997 | Roberts |
| 5,696,233 | A | 12/1997 | Evans et al. |
| 5,707,798 | A | 1/1998 | Brann |

(Continued)

FOREIGN PATENT DOCUMENTS

| | | |
|---|---|---|
| CA | 2994751 A1 | 2/2017 |
| CN | 103483453 A | 1/2014 |

(Continued)

OTHER PUBLICATIONS

Menger et al. ("TALEN-mediated genetic inactivation of the glucocorticoid receptor in cytomegalovirus-specific T cells." 2015. Blood. 126(26):2781-2789). (Year: 2015).*

(Continued)

*Primary Examiner* — Scott Long
(74) *Attorney, Agent, or Firm* — Norton Rose Fulbright US LLP

(57) ABSTRACT

Provided herein are immune cells expressing antigenic receptors, such as a chimeric antigen receptor and a T cell receptor. Further provided herein are methods of treating immune-related disorder by administering the antigen-specific immune cells.

25 Claims, 21 Drawing Sheets
Specification includes a Sequence Listing.

(56) References Cited

U.S. PATENT DOCUMENTS

| | | | |
|---|---|---|---|
| 5,723,329 | A | 3/1998 | Mangelsdorf et al. |
| 5,747,292 | A | 5/1998 | Greenberg et al. |
| 5,789,187 | A | 8/1998 | Ross et al. |
| 5,843,728 | A | 12/1998 | Seed et al. |
| 5,851,828 | A | 12/1998 | Seed et al. |
| 5,906,936 | A | 5/1999 | Eshhar et al. |
| 5,912,132 | A | 6/1999 | Brann |
| 5,912,170 | A | 6/1999 | Seed et al. |
| 5,912,172 | A | 6/1999 | Eshhar et al. |
| 5,981,195 | A | 11/1999 | Fuller et al. |
| 6,001,973 | A | 12/1999 | Strom et al. |
| 6,004,811 | A | 12/1999 | Seed et al. |
| 6,077,675 | A | 6/2000 | Stormann et al. |
| 6,083,751 | A | 7/2000 | Feldhaus et al. |
| 6,090,914 | A | 7/2000 | Linsley et al. |
| 6,103,521 | A | 8/2000 | Capon et al. |
| 6,120,669 | A | 9/2000 | Bradley |
| 6,284,240 | B1 | 9/2001 | Seed et al. |
| 6,361,714 | B1 | 3/2002 | Iwabuchi et al. |
| 6,376,198 | B1 | 4/2002 | Kopin et al. |
| 6,392,013 | B1 | 5/2002 | Seed et al. |
| 6,410,014 | B1 | 6/2002 | Seed et al. |
| 6,410,319 | B1 | 6/2002 | Raubitschek et al. |
| 6,416,957 | B1 | 7/2002 | Evans et al. |
| 6,451,308 | B1 | 9/2002 | Strom et al. |
| 6,500,672 | B1 | 12/2002 | Sladek et al. |
| 6,509,016 | B1 | 1/2003 | Chatterjee et al. |
| 6,534,289 | B1 | 3/2003 | Fuller et al. |
| 6,607,879 | B1 | 8/2003 | Cocks et al. |
| 6,706,867 | B1 | 3/2004 | Lorenz |
| 6,747,665 | B1 | 6/2004 | Stoval, III et al. |
| 6,797,263 | B2 | 9/2004 | Strom et al. |
| 6,824,974 | B2 | 11/2004 | Pisharody et al. |
| 6,937,446 | B2 | 8/2005 | Kamiguchi et al. |
| 6,958,236 | B2 | 10/2005 | Pascal et al. |
| 6,998,476 | B2 | 2/2006 | Strom et al. |
| 7,001,733 | B1 | 2/2006 | Ferrick et al. |
| 7,041,467 | B2 | 5/2006 | Ferrick et al. |
| 7,049,136 | B2 | 5/2006 | Seed et al. |
| 7,052,906 | B1 | 5/2006 | Lawson et al. |
| 7,070,995 | B2 | 7/2006 | Jensen |
| 7,089,052 | B2 | 8/2006 | Kodama et al. |
| 7,094,599 | B2 | 8/2006 | Seed et al. |
| 7,105,644 | B2 | 9/2006 | Rosen et al. |
| 7,118,751 | B1 | 10/2006 | Ledbetter et al. |
| 7,135,603 | B2 | 11/2006 | Messenger |
| 7,196,164 | B2 | 3/2007 | Rosen et al. |
| 7,196,877 | B2 | 3/2007 | Yoshikawa et al. |
| 7,235,190 | B1 | 6/2007 | Wilcoxon et al. |
| 7,258,853 | B2 | 8/2007 | Strom et al. |
| 7,294,468 | B2 | 11/2007 | Bell et al. |
| 7,319,140 | B2 | 1/2008 | Bakker et al. |
| 7,320,787 | B2 | 1/2008 | Seed et al. |
| 7,332,574 | B2 | 2/2008 | Bakker et al. |
| 7,341,944 | B2 | 3/2008 | Harutyunyan |
| 7,347,995 | B2 | 3/2008 | Strom et al. |
| 7,354,762 | B2 | 4/2008 | Jensen |
| 7,379,278 | B2 | 5/2008 | Koui et al. |
| 7,446,179 | B2 | 11/2008 | Jensen et al. |
| 7,446,190 | B2 | 11/2008 | Sadelain et al. |
| 7,468,248 | B2 | 12/2008 | DeNise et al. |
| 7,485,600 | B2 | 2/2009 | Harutyunyan et al. |
| 7,514,537 | B2 | 4/2009 | Jensen |
| 7,569,664 | B2 | 8/2009 | Jakobsen et al. |
| 7,569,670 | B2 | 8/2009 | Novak et al. |
| 7,572,772 | B2 | 8/2009 | Linsley et al. |
| 7,579,439 | B2 | 8/2009 | Strom et al. |
| 7,628,986 | B2 | 12/2009 | Weber et al. |
| 7,629,171 | B2 | 12/2009 | Meagher et al. |
| 7,659,093 | B2 | 2/2010 | Bakker et al. |
| 7,700,728 | B2 | 4/2010 | Bates et al. |
| 7,723,111 | B2 | 5/2010 | Hwu et al. |
| 7,732,133 | B2 | 6/2010 | Yabuta et al. |
| 7,732,149 | B2 | 6/2010 | Kojima et al. |
| 7,736,644 | B2 | 6/2010 | Weber et al. |
| 7,741,465 | B1 | 6/2010 | Eshhar et al. |
| 7,834,152 | B2 | 11/2010 | Strom et al. |
| 7,919,086 | B2 | 4/2011 | Nakano et al. |
| 7,948,154 | B2 | 5/2011 | Ifuku et al. |
| 7,964,349 | B2 | 6/2011 | Bell et al. |
| 7,968,687 | B2 | 6/2011 | McDonagh et al. |
| 7,972,438 | B2 | 7/2011 | Fei et al. |
| 7,998,736 | B2 | 8/2011 | Morgan et al. |
| 8,008,029 | B2 | 8/2011 | Lefevre |
| 8,088,589 | B2 | 1/2012 | Muraca |
| 8,105,769 | B2 | 1/2012 | Bell et al. |
| 8,120,239 | B2 | 2/2012 | Cheon et al. |
| 8,124,084 | B2 | 2/2012 | Lefrancois et al. |
| 8,124,361 | B2 | 2/2012 | Slack et al. |
| 8,129,125 | B2 | 3/2012 | Muraca |
| 8,158,360 | B2 | 4/2012 | Heise et al. |
| 8,178,660 | B2 | 5/2012 | Weiner et al. |
| 8,263,375 | B2 | 9/2012 | Abassi et al. |
| 8,329,421 | B2 | 12/2012 | Powell et al. |
| 8,350,108 | B2 | 1/2013 | Cortright et al. |
| 8,367,882 | B2 | 2/2013 | Cortright et al. |
| 8,399,645 | B2 | 3/2013 | Campana et al. |
| 8,435,762 | B2 | 5/2013 | Sternson et al. |
| 8,450,112 | B2 | 5/2013 | Li et al. |
| 8,465,743 | B2 | 6/2013 | Rosenberg et al. |
| 8,465,916 | B2 | 6/2013 | Bell et al. |
| 8,535,672 | B2 | 9/2013 | Kaempfer et al. |
| 8,591,858 | B2 | 11/2013 | Harutyunyan et al. |
| 8,592,567 | B2 | 11/2013 | Weiner et al. |
| 8,679,492 | B2 | 3/2014 | Blein et al. |
| 8,710,186 | B2 | 4/2014 | Li et al. |
| 8,771,664 | B2 | 7/2014 | Berraondo Lopez et al. |
| 8,796,421 | B2 | 8/2014 | Li et al. |
| 8,802,374 | B2 | 8/2014 | Jensen |
| 8,822,196 | B2 | 9/2014 | Rosenberg et al. |
| 8,822,647 | B2 | 9/2014 | Jensen |
| 8,859,275 | B2 | 10/2014 | Notka et al. |
| 8,871,114 | B2 | 10/2014 | Miyagawa et al. |
| 8,871,191 | B2 | 10/2014 | Pavlakis et al. |
| 8,877,199 | B2 | 11/2014 | Rader et al. |
| 8,883,992 | B2 | 11/2014 | Damschroder et al. |
| 8,900,816 | B2 | 12/2014 | Schmittling et al. |
| 8,900,820 | B2 | 12/2014 | Muraca |
| 8,906,682 | B2 | 12/2014 | June et al. |
| 8,911,993 | B2 | 12/2014 | June et al. |
| 8,912,385 | B2 | 12/2014 | Meagher |
| 8,916,381 | B1 | 12/2014 | June et al. |
| 8,940,288 | B2 | 1/2015 | Lefrancois et al. |
| 8,975,071 | B1 | 3/2015 | June et al. |
| 9,035,036 | B2 | 5/2015 | Bell et al. |
| 9,040,669 | B2 | 5/2015 | Cheung et al. |
| 9,101,584 | B2 | 8/2015 | June et al. |
| 9,102,760 | B2 | 8/2015 | June et al. |
| 9,102,761 | B2 | 8/2015 | June et al. |
| 9,115,171 | B2 | 8/2015 | Ong et al. |
| 9,156,915 | B2 | 10/2015 | Waldman et al. |
| 9,163,258 | B2 | 10/2015 | Riddell et al. |
| 9,169,328 | B2 | 10/2015 | Spriggs et al. |
| 9,175,308 | B2 | 11/2015 | Shiku et al. |
| 9,181,527 | B2 | 11/2015 | Sentman |
| 9,187,732 | B2 | 11/2015 | Wolschek et al. |
| 9,212,104 | B2 | 12/2015 | Qiao et al. |
| 9,212,229 | B2 | 12/2015 | Schonfeld et al. |
| 9,220,728 | B2 | 12/2015 | Sadelain et al. |
| 9,233,125 | B2 | 1/2016 | Davila et al. |
| 9,266,960 | B2 | 2/2016 | Morgan et al. |
| 9,272,002 | B2 | 3/2016 | Powell, Jr. et al. |
| 9,273,283 | B2 | 3/2016 | Sentman |
| 9,315,585 | B2 | 4/2016 | Cheung et al. |
| 9,328,156 | B2 | 5/2016 | June et al. |
| 9,359,447 | B2 | 6/2016 | Feldman et al. |
| 9,365,630 | B2 | 6/2016 | Lefrancois et al. |
| 9,365,641 | B2 | 6/2016 | June et al. |
| 9,371,368 | B2 | 6/2016 | Lefrancois et al. |
| 9,393,268 | B2 | 7/2016 | Waldman et al. |
| 9,394,368 | B2 | 7/2016 | Brogdon et al. |
| 9,402,865 | B2 | 8/2016 | Powell et al. |
| 9,422,351 | B2 | 8/2016 | Scholler et al. |
| 9,422,360 | B2 | 8/2016 | Suo et al. |

(56) References Cited

U.S. PATENT DOCUMENTS

| | | |
|---|---|---|
| 9,446,105 B2 | 9/2016 | Powell, Jr. |
| 9,447,194 B2 | 9/2016 | Jensen |
| 9,453,075 B2 | 9/2016 | Cheung et al. |
| 9,464,140 B2 | 10/2016 | June et al. |
| 9,476,028 B2 | 10/2016 | Karlsson-Parra et al. |
| 9,481,728 B2 | 11/2016 | June et al. |
| 9,487,800 B2 | 11/2016 | Schonfeld et al. |
| 9,492,499 B2 | 11/2016 | Jaynes et al. |
| 9,493,740 B2 | 11/2016 | Brenner et al. |
| 9,499,629 B2 | 11/2016 | June et al. |
| 9,499,823 B2 | 11/2016 | De Lorenzo et al. |
| 9,511,092 B2 | 12/2016 | Campana et al. |
| 9,518,119 B2 | 12/2016 | Bergstein |
| 9,518,123 B2 | 12/2016 | June et al. |
| 9,518,132 B2 | 12/2016 | Li et al. |
| 9,522,955 B2 | 12/2016 | Rosenberg et al. |
| 9,540,445 B2 | 1/2017 | June et al. |
| 9,562,087 B2 | 2/2017 | Ring et al. |
| 9,572,836 B2 | 2/2017 | June et al. |
| 9,572,837 B2 | 2/2017 | Wu |
| 9,573,988 B2 | 2/2017 | Brogdon et al. |
| 9,580,685 B2 | 2/2017 | Jensen |
| 9,587,020 B2 | 3/2017 | Wu et al. |
| 9,597,357 B2 | 3/2017 | Gregory et al. |
| 9,605,049 B2 | 3/2017 | Campana et al. |
| 9,617,336 B2 | 4/2017 | Cojocaru et al. |
| 9,623,049 B2 | 4/2017 | Eshhar et al. |
| 9,624,276 B2 | 4/2017 | Young et al. |
| 9,624,306 B2 | 4/2017 | Morgan et al. |
| 9,629,877 B2 | 4/2017 | Cooper et al. |
| 9,650,428 B2 | 5/2017 | Sampath et al. |
| 9,657,105 B2 | 5/2017 | Forman et al. |
| 9,663,763 B2 | 5/2017 | Sentman |
| 9,670,281 B2 | 6/2017 | Lim et al. |
| 9,677,136 B2 | 6/2017 | Denise et al. |
| 9,685,295 B2 | 6/2017 | King et al. |
| 9,688,740 B2 | 6/2017 | Choi et al. |
| 9,688,760 B2 | 6/2017 | Kufer et al. |
| 9,701,758 B2 | 7/2017 | Cooper et al. |
| 9,708,384 B2 | 7/2017 | Scholler et al. |
| 9,714,278 B2 | 7/2017 | June et al. |
| 9,725,492 B2 | 8/2017 | Felber et al. |
| 9,725,519 B2 | 8/2017 | Masuko et al. |
| 9,745,368 B2 | 8/2017 | Milone et al. |
| 9,765,142 B2 | 9/2017 | Dimitrov et al. |
| 9,765,342 B2 | 9/2017 | Kochenderfer |
| 9,777,061 B2 | 10/2017 | Ebersbach et al. |
| 9,783,591 B2 | 10/2017 | June et al. |
| 9,790,261 B2 | 10/2017 | Felber et al. |
| 9,790,278 B2 | 10/2017 | Sentman et al. |
| 9,790,282 B2 | 10/2017 | Orentas et al. |
| 9,809,581 B2 | 11/2017 | Chen et al. |
| 9,815,901 B2 | 11/2017 | Brogdon et al. |
| 9,815,908 B2 | 11/2017 | Schonfeld et al. |
| 9,821,011 B1 | 11/2017 | Sentman |
| 9,821,012 B2 | 11/2017 | Wu et al. |
| 9,822,340 B1 | 11/2017 | Sentman |
| 9,828,399 B2 | 11/2017 | Tremblay et al. |
| 9,828,435 B2 | 11/2017 | Evans et al. |
| 9,833,476 B2 | 12/2017 | Zhang et al. |
| 9,833,480 B2 | 12/2017 | Junghans et al. |
| 9,834,545 B2 | 12/2017 | Chen et al. |
| 9,834,590 B2 | 12/2017 | Campana et al. |
| 9,845,362 B2 | 12/2017 | Mukherjee |
| 9,855,297 B2 | 1/2018 | Duchateau et al. |
| 9,855,298 B2 | 1/2018 | Bot et al. |
| 9,856,176 B2 | 1/2018 | Harris et al. |
| 9,856,322 B2 | 1/2018 | Campana et al. |
| 9,856,497 B2 | 1/2018 | Qi et al. |
| 9,868,774 B2 | 1/2018 | Orentas et al. |
| 9,889,160 B2 | 2/2018 | Jantz et al. |
| 9,889,161 B2 | 2/2018 | Jantz et al. |
| 9,913,882 B2 | 3/2018 | Slawin et al. |
| 9,914,909 B2 | 3/2018 | Brown et al. |
| 9,920,132 B2 | 3/2018 | Wels et al. |
| 9,931,347 B2 | 4/2018 | Cowley et al. |
| 9,931,377 B2 | 4/2018 | Pavlakis et al. |
| 9,932,387 B2 | 4/2018 | Lefrancois et al. |
| 9,932,405 B2 | 4/2018 | Xiao et al. |
| 9,932,572 B2 | 4/2018 | Spencer et al. |
| 9,938,497 B2 | 4/2018 | Sentman |
| 9,944,702 B2 | 4/2018 | Galetto |
| 9,944,709 B2 | 4/2018 | Galetto |
| 9,944,931 B2 | 4/2018 | Wucherpfennig et al. |
| 9,950,010 B1 | 4/2018 | Jantz et al. |
| 9,950,011 B1 | 4/2018 | Jantz et al. |
| 9,951,118 B2 | 4/2018 | Kitchen et al. |
| 9,957,480 B2 | 5/2018 | Sentman |
| 9,963,497 B2 | 5/2018 | Kaempfer et al. |
| 9,969,790 B2 | 5/2018 | Lefrancois et al. |
| 9,987,308 B2 | 6/2018 | Riddell et al. |
| 10,011,658 B2 | 7/2018 | Liu et al. |
| 10,023,648 B2 | 7/2018 | Hombach et al. |
| 10,040,846 B2 | 8/2018 | Frigault et al. |
| 10,071,118 B2 | 9/2018 | Katz et al. |
| 10,072,078 B2 | 9/2018 | Orentas et al. |
| 10,117,897 B2 | 11/2018 | Sadelain et al. |
| 10,166,255 B2 | 1/2019 | Moriarity et al. |
| 10,351,612 B2 | 7/2019 | Schonfeld et al. |
| 10,406,177 B2 | 9/2019 | Moriarity et al. |
| 2002/0102264 A1 | 8/2002 | Cheung |
| 2003/0148982 A1 | 8/2003 | Brenner et al. |
| 2004/0038886 A1 | 2/2004 | Finney et al. |
| 2006/0110360 A1 | 5/2006 | Klingemann |
| 2007/0071759 A1 | 3/2007 | Shin et al. |
| 2008/0050341 A1 | 2/2008 | Morgan et al. |
| 2010/0105136 A1 | 4/2010 | Carter et al. |
| 2011/0286980 A1 | 11/2011 | Brenner |
| 2012/0040452 A1 | 2/2012 | Nishimura et al. |
| 2012/0148552 A1 | 6/2012 | Jensen |
| 2013/0001376 A1 | 1/2013 | Peled et al. |
| 2013/0280221 A1 | 10/2013 | Schonfeld et al. |
| 2014/0044714 A1 | 2/2014 | Ho et al. |
| 2014/0255363 A1 | 9/2014 | Metelitsa et al. |
| 2014/0322216 A1 | 10/2014 | Kaplan |
| 2015/0368360 A1 | 12/2015 | Liang et al. |
| 2015/0376296 A1* | 12/2015 | Fedorov .............. A61P 19/00 424/93.71 |
| 2016/0145337 A1 | 5/2016 | Galetto et al. |
| 2016/0158285 A1 | 6/2016 | Cooper et al. |
| 2016/0207989 A1 | 7/2016 | Short |
| 2017/0008963 A1 | 1/2017 | Brogdon et al. |
| 2017/0067021 A1 | 3/2017 | Moriarity et al. |
| 2017/0081405 A1 | 3/2017 | Adusumilli et al. |
| 2017/0152480 A1 | 6/2017 | Jensen |
| 2017/0335281 A1 | 11/2017 | Loew et al. |
| 2018/0142035 A1 | 5/2018 | Lobb et al. |
| 2019/0046659 A1 | 2/2019 | Wang et al. |
| 2019/0345217 A1 | 11/2019 | Ma et al. |
| 2021/0230548 A1* | 7/2021 | Daher ................ C07K 14/7051 |

FOREIGN PATENT DOCUMENTS

| | | |
|---|---|---|
| CN | 106397593 A | 2/2017 |
| EP | 2614151 A1 | 7/2013 |
| EP | 2995682 A1 | 3/2016 |
| EP | 3333192 A1 | 6/2018 |
| WO | 2006133398 A2 | 12/2006 |
| WO | 2010042189 A2 | 4/2010 |
| WO | 2012033885 A1 | 3/2012 |
| WO | 2012/136231 A1 | 10/2012 |
| WO | 2013040371 A2 | 3/2013 |
| WO | 2013/070468 A1 | 5/2013 |
| WO | 2014138314 A1 | 9/2014 |
| WO | 2014/186469 A2 | 11/2014 |
| WO | 2015/051247 | 4/2015 |
| WO | 2016/044811 A1 | 3/2016 |
| WO | 2016/102965 A1 | 6/2016 |
| WO | 2016/172606 A1 | 10/2016 |
| WO | 2016/174405 A1 | 11/2016 |
| WO | 2016/197108 A1 | 12/2016 |
| WO | 2017/020812 A1 | 2/2017 |
| WO | 2017/027843 A1 | 2/2017 |
| WO | 2017/048902 A1 | 3/2017 |

(56) References Cited

FOREIGN PATENT DOCUMENTS

| WO | 2017/096329 | A1 | 6/2017 | |
|---|---|---|---|---|
| WO | 2017/100861 | A1 | 6/2017 | |
| WO | 2017/123556 | A1 | 7/2017 | |
| WO | 2017/220704 | A1 | 12/2017 | |
| WO | WO2017/222593 | * | 12/2017 | ............ A61K 35/17 |
| WO | 2018/027155 | A1 | 2/2018 | |
| WO | 2018/081470 | A1 | 5/2018 | |

OTHER PUBLICATIONS

Hofflin et al. "Generation of COB+ T cells expressing two additional T-cell receptors (TETARs) for personalised melanoma therapy," Cancer Biology & Therapy, Jul. 15, 2015 (Jul. 15, 2015), vol. 16, Iss. 9, pp. 1323-1331.
Agrawal V., et al., 14G2a anti-GD2 crossreactivity with the CD166 antigen., J Immunother., 1014-1015, Nov.-Dec. 2010;33(9).
Baev, J et al. "Distinct homeostatic requirements of CD4+ and CD4-subsets of Va24-invariant natural kileer T cells in humans", Blood, vol. 104, No. 13 (2004), pp. 4150-4156.
Batra et al: "Armored Glypican-3-Specific CART Cells for the Immunotherapy of Hepatocellular Carcinoma", Molecular Therapy, vol. 26, No. 5, Suppl. 1, May 2018 (May 2018), p. 441.
Bendelac, et al. "Teh Biology of NKT Cells", Annu. Rev. Immunol., 25, (2007), pp. 297-336.
Bendelac, et al. "CD1 Recognition by Mouse NK1+ T Lymphosytes", Science, 268, (1995), pp. 863-865.
Brocker and Karjalainen, "Signals through T Cell Receptor-z Chain Alone Are Insufficient to Prime Resting T Lymphocytes", J. Exp. Med., May 1, 1995, vol. 181, pp. 1653-1659, The Rockefeller University Press.
Cartellieri et al.: "Chimeric Antigen Receptor-Engineered T Cells for Immunotherapy of Cancer", Journal of Biomedicine and Biotechnology, vol. 21, No. 4, Jan. 1, 2010 (Jan. 1, 2010), pp. 427-513.
Chan et al. "Immunohistochemical Expression of Glypican-3 in Pediatric Tumors: An Analysis of 414 Cases", Pediatric and Developmental Pathology, 2013, vol. 16, pp. 272-277.
Chang, et al. "Sustained expansion of NKT cells and antigen-specific T cells after injection of a-galactosyl-ceramide loaded mature dendritic cells in cancer patients", J. Exp. Med.,vol. 201, No. 9, (2005), pp. 1503-1517.
Cheresh et al., "Biosynthesis and Expression of the Disialoganglioside GD2, a Relevant Target Antigen on Small Cell Lung Carcinoma for Monoclonal Antibody-mediated Cytolysis1", Cancer Research, vol. 46, Oct. 1, 1986 (Oct. 1, 1986), pp. 5112-5118.
Cohen et al., "Shared and distinct transcriptional programs underlie the hybrid nature of iNKT cells", Nat Immunol., Jan. 2013; 14(1): 90-99.
Crowe, et al. "Differential antitumor immunity mediated by NKT cell subsets in vivo", J. Exp. Med., vol. 202, No. 9, (2005), pp. 1279-1288.
Delconte et al:"CIS is a potent checkpoint in NK cell-mediated tumor immunity", Nature Immunology, vol. 17, No. 7, Jul. 2016, Nature America, Inc.
Dhodapkar, Madhav V. "Harnessing human CD1d restricted T cells for tumor immunity: progress and challenges", Front Biosci., 14, (2009), pp. 796-807.
Di Stasi, et al. "Inducible Apoptosis as a Safety Switch for Adoptive Cell Therapy", N. Engl. J. Med., 365, (2011), pp. 1673-1683.
Dotti et al., Fifteen Years of Gene Therapy Based on Chimeric Antigen Receptors: "Are We Nearly There Yet?", Human Gene Therapy, Nov. 2009, 20: 1229-1239.
Dotti G, et al.,. "Design and development of therapies using chimeric antigen receptorexpressing T cells," Immunol Rev. 2014;257(1): 107-126.
Exley et al., "Selective activation, expansion, and monitoring of human iNKT cells with a monoclonal antibody specific for the TCR a-chain CDR3 loop", Eur. J. Immunol. 2008. 38: 1756-1766.

Fehniger, et al. "Fatal Leukemia in Interleukin 15 Transgenic Mice Follows Early Expansions in Natural Killer and Memory Phenotype CD8+ T Cells", J. Exp. Med., vol. 193, No. 2, (2001), pp. 219-231.
Furukawa et al., Ann. N.Y. Acad. Sci. 1086: 185-198 (2006).
Gao et al.: "Development of T Cells Redirected to Glypican-3 for the Treatment of Hepatocellular Carcinoma", Clinical Cancer Research, vol. 20, No. 24, Dec. 15, 2014 (Dec. 15, 2014), pp. 6418-6428.
Gao et al.: "Supplementary Data: Development of T Cells Redirected to Glypican-3 for the Treatment of Hepatocellular Carcinoma", Clinical Cancer Research, Dec. 15, 2014 (Dec. 15, 2014), pp. 6418-6642, Figures Only—Retrieved from Internet: http://clincancerres.aacrjournals.org/content/20/24/6418.
Godfrey and Kronenberg, "Going both ways: immune regulation via CD1d-dependent NKT cells", Journal of Clinical Investigation, vol. 114, No. 10, Nov. 2004, pp. 1379-1388.
Godfrey et al., "Raising the NKT cell family", Nat Rev Immun, Mar. 2010, vol. 11, No. 3, pp. 197-206, Nature America, Inc.
Godfrey, Dale I., et al; NTK cells: what's in a name?; Nature Reviews Immunology; Nature Publishing Group; 2004, vol. 4; 231-237.
Graef P, et al. "Serial transfer of single-cell-derived immunocompetence reveals sternness of CDS(+)central memory T cells," Immunity. 2014;41(1):116-126.
Heczey et al., "Invariant NKT cells with chimeric antigen receptor provide a novel platform for safe and effective cancer immunotherapy", BLOOD, Oct. 30, 2014, vol. 124, No. 18, pp. 2824-2833, The American Society of Hematology.
Heczey et al: "NKT cells as a novel platform for cancer immunotherapy with chimeric antigen receptors", The Journal of Immuno, The American Association of Immunologists, US, vol. 190, May 1, 2013 (May 1, 2013 ), p. P2038.
Hsu, et al. "Cytokine-independent growth and clonal expansion of a primary human CD8+ T-cell clone following retroviral transduction with the IL-15 gene", Blood, vol. 109, No. 12, (2007), pp. 5168-5177.
Mai, et al., "Complement-Mediated Mechanisms in Anti-GD2 Monoclonal Antibody Therapy for Murine Metastatic Cancer". American Association for Cancer Research, 10562-10568, 2005.
Ishikawa, et al. "A Phase I Study of a-Galactosylceramide (KRN7000)-Pulsed Dendritic Cells in Patients with Advanced and Recurrent Non-Small Cell Lung Cancer", Clin. Cancer Res., 11, (2005), pp. 1910-1917.
Johnson et al. "Rational development and characterization of humanized anti-EGFR variant III chimeric antigen receptor T cells for glioblastoma" Science Translational Medicine, Feb. 2015, vol. 7, No. 275.
Kalos M, June CH. "Adoptive T cell transfer for cancer immunotherapy in the era of synthetic biology," Immunity 2013;39(1):49-60.
Kambayashi, Taku, et al; Emergence of D8+ T Cells Expressing NI Cell Receptors in Influenza A virus-infected mice; The Journal of Immunology; 2000, 165: 4964-4969.
Kershaw, et al. "A Phase I Study on Adoptive Immunotherapy Using Gene-Modified T cells for Ovarian Cancer", Clin. Cancer Res., 12, (2006), pp. 6106-6115.
Khor et al. "CISH and Susceptibility to Infectious Diseases," New England Journal of Medicine, Jun. 3, 2010 (Jun. 3, 2010), vol. 362, No. 22, pp. 2092-2101.
Kim, et al. "4-1BB Engagement Costimulates NKT Cell Activation and Exacerbates NKT Cell Ligand-Induced Airway Hyperresponsiveness and Inflammation", J. Immunol., 180, (2008), pp. 2062-2068.
Kronenberg, et al. "The unconventional lifestyle of NKT cells", Nat. Rev. Immunol., 2, (2002), pp. 557-568.
Kunii, et al. "Combination therapy of in vitro-expanded natural killer T cells and a-galactosylceramide-pulsed antigen-presenting cells in patients with recurrent head and neck carcinoma", Cancer Sci., vol. 100, No. 6, (2009), pp. 1092-1098.
Lantz, et al. "An Invariant T Cell Receptor a Chain Is Used by a Unique Subset of Major Histocompatibility Complex Class I-specific CD4+ and CD4-8-T Cells in Mice and Himans", J. Exp. Med., 180, (1994), pp. 1097-1106.
Lappas et al., "Adenosine A2A receptor activation reduces hepatic ischemia reperfusion injury by inhibiting CD1d-dependent NKT

(56) References Cited

OTHER PUBLICATIONS cell activation", J. Experimental Medicine, vol. 203, No. 12, Nov. 27, 2006, pp. 2639-2648, The Rockefeller University Press.
Levy et al. "Expression of glypican-3 in undifferentiated embryonal scarcoma and mesenchymal hamartoma of the liver", Human Patholoy (2012) 43, 695-791.
Li et al., "NKT Cell Activation Mediates Neutrophil IFN-g Production and Renal Ischemia-Reperfusion Injury", The Journal of Immunology, 2007, 178: 5899-5911.
Li et al.: "Immunotherapy of Hepatocellular Carcinoma With T Cells Engineered To Express Glypican-3-Specific Chimeric Antigen Receptors", Molecular Therapy, vol. 23, No. Suppl. 1, May 2015 (May 2015), pp. SI64-SI65.; and 18th Annual Meeting of the American-Society-of-Gene-and-Cell-Therapy (ASGCT); New Orleans, LA, USA; May 13-16, 2015.
Li et al.: "In vitro validation of human glypican-3 specific chimeric antigen receptors for hepatocellular carcinoma", HEPATOLOGY, vol. 60, No. Suppl. 1, Sp. Iss. SI, Oct. 2014, p. 870A, XP002780485; and 65th Annual Meeting of the American-Association-For-The-Study-of-Liver-Diseases; Boston, MA, USA Nov. 7-11, 2014, ISSN: 0270-9139.
Li et al.: "Validation of glypican-3-specific scFv isolated from paired display/secretory yeast display library", BMC Biotechnology, vol. 12, No. 1, May 7, 2012 (May 7, 2012), p. 23. Biomed Central Ltd., London, GB.
Liu et al., "IL-15 protects NKT cells from inhibition by tumor-associated macrophages and enhances antimetastatic activity", The Journal of Clinical Invesigation, vol. 122, No. 6, Jun. 2012, pp. 2221-2233.
Lo et al. (Cancer Res. 201 0; 16(1 0): 2769-2780).
Louis et al., "Treatment of High-Risk Neuroblastoma with Adoptively Transferred T Lymphocytes Genetically Engineered to Recognize GD2", Biology of Blood and Marrow Transplantation, 15(2):26, 2009.
MacDonald, H. Robson "NKT cellsL In the Beginning . . . " Eur. J. Immunol. 2007. 37: S111-115, Wiley-VCH Verlag GmbH & Co. KGaA, Weinheim.
Yvon et al., "Immunotherapy of Metastatic Melanoma Using Genetically Engineered GD3-Specific T cells", Clinical Cancer Research, 15(18):5852-5860, 2009.
Zaini, et al. "OX40 ligand expressed by DCs costimulates NKT and CD4+ Th cell antitumor immunity in mice", J. Clin, Invest., 117(11), (2007), pp. 3330-3338.
Zhao et al.,"GS2 Oligosaccharide: Target for Cytotoxic T Lymphocytes" The Journal of Experimental Medicine, Rockefeller University Press, US, vol. 182, Jul. 1, 1995 (Jul. 1, 1995), pp. 67-74.
Zou, et al. "Immunosuppressive networks in the tumour environment and their therapeutic relevance", Nat. Rev. Cancer, 5, (2005), pp. 263-274.
Maher, et al. "Human T-lymphocyte cytotoxicity and proliferation directed by a single chimeric TCRz/CD28 receptor", Nat. Biotechnol., 20, (2002), pp. 70-75.
Mantovani et al., "Cancer-related inflammation", NATURE, vol. 454:24, Jul. 2008, pp. 436-444, Macmillan Publishers Limited.
Matsuda, et al. "Homeostasis of Val 4iNKT cells", Nat. Immunol., vol. 3, No. 10, (2002), pp. 966-974.
Metelitsa et al., "Human NKT Cells Mediate Antitumor Cytotoxicity Directly by Recognizing Target Cell CD1d with Bound Ligand or Indirectly by Producing IL-2 to Activate NK Cells", Journal of Immunology, 2001; 167:3114-3122; The American Association of Immunologists, Inc.
Metelitsa, "Anti-tumor potential of type-I NKT cells against CD1d-positive and CD1d-negative tumors in humans", Clinical Immunology (2011) 140, pp. 119-129.
Metelitsa, et al. "Natural Killer T Cells Infiltrate Neuroblastomas Expressing the Chemokine CCL2", J. Exp. Med., vol. 199, No. 9, (2004), pp. 1213-1221.

Molling, et al. "Low Levels of Circulating Invariant Natural Killer T Cells Predict Poor Clinical Outcome in Patients With Head and Neck Squamous Cell Carcinoma", J. Clin. Oncol., vol. 25, No. 7, (2007), pp. 862-868.
Motohashi, et al. "A Phase I-II Study of a-Galactosylceramide-Pulsed IL-2/GM-CSF-Cultured Peripheral Blood Mononuclear Cells in Patients with Advanced and Recurrent Non-Small Cell Lung Cancer", J. Immunol., 182, (2009), pp. 2492-2501.
Mujoo, et al., "Functional Properties and Effect on Growth Suppression of Human Neuroblastoma Tumors by Isotype Switch Variants of Monoclonal Antiganglioside GD2". American Association for Cancer Research, 2857-2861, 1989.
Nandagopal et al. "The critical role of IL-15-PI3K-mTOR pathway in natural killer cell effector functions," Frontiers in Immunology, Apr. 23, 2014 (Apr. 23, 2014), vol. 5, Art. 187, pp. 1-12.
Navid et al. (Curr Cancer Drug Targets. 201 0; 1 0(2): 200-209).
Nguyen et al: "Glypican-3-Specific CAR NKT Cells Armored with IL-15 Exhibit Potent and Sustained Anti-Tumor Activity against Hepatocellular Carcinoma", Molecular Therapy, vol. 26, No. 5, Suppl. 1, May 2018 (May 2018), p. 62.
Nieda, et al. "Therapeutic activation of Va24+Vb11+ NKT cells in human subjects results in highly coordinated secondary activation of acquired and innate immunity", Blood, vol. 103, No. 2,(2004), pp. 383-389.
Peralbo, Esther, et al; Invariant NKT and NKT-like lymphocytes: Two different T cell subsets that are differentially affectedby ageing; Science Direct, Experimental Gerontology 42; Dept. of Immunology, 2007; pp. 703-708.
Porcelli, et al. "Analysis of T Cell Antigen Receptor (TCR) Expression by Human Peripheral Blood CD4-8-a/b T Cell Demonstrates Preferential Use of Several Vb genes and an Invariant TCR a Chain", J. Exp. Med., 178, (1993), pp. 1-16.
Porter, et al. "Chimeric Antigen Receptor-Modified T Cells in Chronic Lymphoid Leukemia", N. Engl. J. Med., 365 (8), (2011), pp. 725-733.
Pule et al., Molecular Therapy vol. 12: 933-941 (2005).
Pule, et al. "Virus-specific T cells engineered to coexpress tumor-specific receptors: persistence and antitumor activity in individuals with neuroblastoma", Nat. Med., 14(11), (2008), pp. 1264-1270.
Quintarelli, et al. "Co-expression of sytokine and suicide genes to enhance the activity and safety of tumor-specific cytotoxic T lymphosytes", Blood, 110(8), (2007), pp. 2793-2802.
Rettig, et al. "Transduction and Selection of Human T Cells with Novel CD34/Thymidine Kinase Chimeric Suicide Genes for the Treatment of Graft-versus-Host Disease", Milecular Ther., 8(1), (2003), pp. 29-11.
Riedl, et al. "The apoptosome: signalling platform of cell death", Nat. Rev. Mol. Cell Biol., 8, (2007), pp. 405-413.
Rossig et al., "Targeting of GD2-Positive Tumor Cells by Human T Lymphocytes Engineered to Express Chimeric T-Cell Receptor Genes", Int. J. Cancer, 94:228-236, 2001.
Rossig et al., Epstein-Barr virus-specific human T lymphocytes expressing antitumer chimeric T-cell receptors: potential for improved immunotherapy, Blood, Mar. 15, 2002; vol. 99, No. 6, 2009-2016.
Rossjohn, Jamie, et al; Recognition of CD1d-restricted antigens by natural killer T cells; Nat. Rev. Immunol., Dec. 2012; 12(12): 845-857.
Sadelain et al. (Current Opinion in Immunology 2009, 21 :215-223).
Sato, et al. "Development of an IL-15—autocrine CD8 T-cell leukemia in IL-15—transgenic mice requires the cis expression of IL-15Ra", Blood, 117, (2011), pp. 4032-4040.
Savoldo, et al. "CD28 costimulation improves expansion and persistence of chimeric antigen receptor-modified T cells in lymphoma patients", J. Clin. Invest., 112(5), (2011), pp. 1822-1826.
Shah, Divya K. "T-Cell Development in Thymus", British Society for Immunology, London.
Sica and Bronte, "Altered macrophage differentiation and immune dysfunction in tumor development", J. Clin. Invest., May 2007, vol. 117, No. 5, pp. 1155-1166.
Sica et al., "Macrophage polarization in tumour progression", Seminars in Cancer Biology, 18 (Apr. 2008) pp. 349-355.

(56) References Cited

OTHER PUBLICATIONS

Slifka, Mark K., et al; NK Markers are Expressed on a High Percentage of Virus-Specific CD8+ and CD4+ T Cells; J. Immunol 2000; 164: 209-2015.

Sommermeyer D, et al. "Chimeric antigen receptor-modified T cells derived from defined COB and CD4 subsets confer superior antitumor reactivity in vivo," Leukemia 2015.

Song et al: "In Vivo Persistence, Tumor Localization, and Antitumor Activity of CAR-Engineered T Cells Is Enhanced by Costimulatory Signaling through CD137 (4-1 BB)", Cancer Research, vol. 71, No. 13, Jul. 1, 2011 (Jul. 1, 2011 ), pp. 4617-4627.

Song, et al."Va24-invariant NKT cells mediate antitumor activity via killing of tumor-associated macrophages", J. Clin. Invest., 119(6), (2009), pp. 1524-1536.

Straathof, et al. "An inducible caspase 9 safety switch for T-cell therapy", Blood, 105(11), (2005), pp. 4247-4254.

Suzukil et al., "Glypian-3 (GPC3) as a novel tumor for malignant ovarian tumors and malignant melanoma", Japan Molecular Tumor Markers Research Journal, 2010, vol. 25, p. 31-32.

Swann, et al. "CD1-Restricted T Cells and Tumor Immunity", Curr. Top. Microbiol. immunol., 314, (2007), pp. 293-321.

Tachibana, et al. "Increased Intratumor Va24-Positive Natural Killer T Cells: A Prognostic Factor for Primary Colorectal Carcinomas", Clin. Cancer Res., 11(20), (2005), pp. 7322-7327.

Takahashi, Tsuyoshi, et al; Cutting Edge: Analysis of Human V ?24+CD8+ NK T Cells Activated by ?=Galactosylceramide-Pulsed Monocyte-Derived Dendritic Cells; The Journal of Immunology; 2002; 168:3140-3144.

Tey, et al. "Inducible caspase 9 suicide gene to improve the safety of allodepleted T cells after haploidentical stem cell transplantation", Biol. Blood Marrow Transplant., 13(8), (2007), pp. 913-924.

Till, et al. "Adoptive immunotherapy for indolent non-Hodgkin lymphoma and mantle cell lymphoma using genetically modified autologous CD20-specific T cells", Blood, 112(6), (2008), pp. 2261-2271.

Toretsky et al.: "Glypican-3 Expression in Wilms Tumor and Hepatoblastoma", Journal of Pediatric Hematology/Onocolgy, Nov. 1, 2001, vol. 23, No. 8, pp. 496-499, New York, US.

Torikai et a. "Translational Implications for Off-the-shelf Immune Cells Expressing Chimeric Antigen Receptors," Molecular Therapy, May 16, 2016 (May 16, 2016), vol. 24, No. 7, pp. 1178-1186.

Uldrich, et al. "NKT cell stimulation with glycolipid antigen in vivo: co-stimulation-dependent expansion, Bim-dependent contraction, and hypo-responsiveness to further antigenic challenge", J. Immunol., 175(5), (2005), pp. 3092-3101.

Vinay, et al. "CD137-Deficient Mice Have Reduced NK/NKT Cell Numbers and Function, Are Resistant to Lipopolysaccharide-Induced Shock Syndromes, and Have Lower IL-4 Responses", J. Immunol., 173, (2004), pp. 4218-4229.

Wang X, et al. "Phenotypic and functional attributes of lentivirus-modified CD19-specific human COB+central memory T cells manufactured at clinical scale," J. Immunother. 2012;35(9):689-701.

Wang, Huiming, et al; Tumor-derived soluble MICs impare CD3+ CD56+ NKT-like cell cytotoxicity in cancer patients; Elsevier Immunology Letters 120; 2008; pp. 65-71.

Wilkie et al., J Immunol 2008; 180: 4901-4909.

Xu and Dotti, "Selection bias: maintaining less-differentiated T cells for adoptive immunotherapy", J. Clinical Invest., Jan. 2016, Vo. 126, No. 1, pp. 35-37.

Yoshida et al., "Ganglioside G(D2) in Small Cell Lung Cancer Cell Lines: Enhancement of Cell Proliferation and Mediation of Apoptosis", Cancer Research, May 15, 2001 (May 15, 2001), pp. 4244-4252.

Jennifer Brudno, et al: "Toxicities of Chimeric antigen Receptor T Cells: Recognition and Management"; Blood 2016, Jun. 30; 127(26): 3321-3330.

* cited by examiner

IMMUNE CELLS EXPRESSING ENGINEERED ANTIGEN RECEPTORS

The present application is a national phase application under 35 U.S.C. § 371 of International Application No. PCT/US2018/028418, filed Apr. 19, 2018, which claims the priority benefit of U.S. Provisional Application Ser. No. 62/487,248, filed Apr. 19, 2017, the entire contents of both applications being hereby incorporated by reference.

INCORPORATION OF SEQUENCE LISTING

The sequence listing that is contained in the file named "UTSCP1321US.txt", which is 2 KB (as measured in Microsoft Windows) and was created on Oct. 10, 2019, is filed herewith by electronic submission and is incorporated by reference herein.

BACKGROUND

1. Field

The present invention relates generally to the fields of immunology and medicine. More particularly, it concerns immune cells expressing antigenic receptors, such as chimeric antigen receptors and T cell receptors, in the same cell type.

2. Description of Related Art

Despite technological advancements in the diagnosis and treatment options available to patients diagnosed with cancer, the prognosis still often remains poor and many patients cannot be cured. Immunotherapy holds the promise of offering a potent, yet targeted, treatment for patients diagnosed with various tumors with the potential to eradicate the malignant tumor cells without damaging normal tissues. In theory, the T cells of the immune system are capable of recognizing protein patterns specific for tumor cells and to mediate their destruction through a variety of effector mechanisms. Adoptive T cell therapy is an attempt to harness and amplify the tumor-eradicating capacity of a patient's own T cells and then return these effectors to the patient in such a state that they effectively eliminate residual tumor, however without damaging healthy tissue. Although this approach is not new to the field of tumor immunology, many drawbacks in the clinical use of adoptive T cell therapy impair the full use of this approach in cancer treatments.

Cell therapy using autologous or human leukocyte antigen (HLA)-matched allogeneic donor cells is a promising therapy for many types of diseases, including cancer, and for regenerative medicine. A number of groups have explored strategies to redirect the antigen-specificity of T cells by engineering them to express high affinity artificial TCRs. However, the introduction of additional TCR chains into T cells can result in the formation of mixed dimers between the endogenous and introduced TCR chains, with the potential to result in the generation of T cells with unknown specificity and toxicity. This has significantly limited the translation of this strategy to the clinic. Thus, there is a need to develop improved methods of engineering immune cells for adoptive cell therapy with enhanced specificity as well as dual targeting of tumors.

SUMMARY

In a first embodiment, the present disclosure provides an immune cell engineered to express human IL-15 (hIL-15) and at least two antigen receptors, wherein the at least two antigen receptors comprise a chimeric antigen receptor (CAR) and/or a T cell receptor (TCR). In one embodiment, there is provided an immune cell engineered to express a CAR, TCR, and hIL-15 or another cytokine such as hIL-21, hIL-2 or hIL-18. In another embodiment, there is provided an immune cell is engineered to express hIL-15 and two CARs. In yet another embodiment, there is provided an immune cell is engineered to express hIL-15 and two TCRs. In a further embodiment, there is provided an immune cell is engineered to express 3, 4, 5, or more antigen receptors. In some aspects, the immune cell is allogeneic. In certain aspects, the immune cell is autologous.

In some aspects, the immune cell is further defined as a T cell, peripheral blood lymphocyte, NK cell, invariant NK cell, NKT cell, or stem cell. In certain aspects, the stem cell is a mesenchymal stem cell (MSC) or an induced pluripotent stem (iPS) cell. In some aspects, the immune cell is derived from an iPS cell. In particular aspects, the T cell is a $CD8^+$ T cell, $CD4^+$ T cell, or gamma-delta T cell. In one specific aspects, the T cell is a cytotoxic T lymphocyte (CTL). In particular aspects, the immune cell is a T cell or NK cell.

In certain aspects, the immune cell is engineered to express one or more additional cytokines. In particular aspects, the one or more additional cytokines are IL-21, IL-18 and/or IL-2.

In additional aspects, the immune cell is engineered to have essentially no expression of glucocorticoid receptor (GR), TGFβ receptor, and/or CISH. In some aspects, said immune cell is engineered using one or more guide RNAs and a Cas9 enzyme. In specific aspects, the one or more guide RNAs comprise SEQ ID NOs: 1-2, such as to silence GR. In particular aspects, the one or more guide RNAs comprise SEQ ID NOs: 3-4, such as to silence TGFβ. In some aspects, the one or more guide RNAs comprise SEQ ID NOs.: 1-4, such as to target GR and TGFβ. In particular aspects, the TGFβ receptor is further defined as TGFβ-RII.

In some aspects, the immune cell is isolated from peripheral blood, cord blood, or bone marrow. In particular aspects, the immune cell is isolated from cord blood, such as cord blood pooled from 2 or more individual cord blood units.

In further aspects, the immune cell further expresses a suicide gene. In certain aspects, the suicide gene is CD20, CD52, EGFRv3, or inducible caspase 9. In particular aspects, the suicide gene is inducible caspase 9.

In some aspects, the at least two antigen receptors, such as CAR and/or TCR, comprise antigen binding regions selected from the group consisting of F(ab')2, Fab', Fab, Fv, and scFv. In certain aspects, the antigen binding regions of the at least two antigen receptors, such as CAR and/or TCR, bind one or more tumor associated antigens. In specific aspects, the tumor associated antigens are CD19, CD319/CS1, ROR1, CD20, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD99, CD33, CD5, CD7, ROR1, CD23, CD30, CD56, c-Met, mesothelin, GD3, HERV-K, IL-11Ralpha, kappa chain, lambda chain, CSPG4, ERBB2, WT-1, EGFRvIII, TRAIL/DR4, and/or VEGFR2. In certain aspects, the antigen binding region of the first antigen receptor, such as the CAR, is distinct from the antigen binding region of the second antigen receptor, such as the TCR. In some aspects, the antigen binding region of the a first antigen receptor, such as a CAR, binds to a first antigen and the antigen binding region of a second antigen receptor, such as a TCR, binds to a second antigen. In specific aspects, first antigen is EGFRvIII and the second antigen is NY-ESO. In other aspects, first antigen is HER2/Neu and the second antigen is MUC-1. In some aspects, first antigen is CA-125 and the second antigen is MUC-1. In certain aspects, first antigen is CA-125 and the second antigen is WT-1. In some aspects, first antigen is EGFRvIII and the second antigen is Mage-A3, Mage-A4, or Mage-A10. In particular aspects, first antigen is EGFRvIII and the second antigen is TRAIL/DR4. In certain aspects, first antigen is CEA-CAR and the second antigen is Mage-A3-TCR, Mage-A4-TCR or Mage-A10. In some aspects, first antigen is HER2/Neu, CEA-CAR, and/or CA-125, EGFRvIII and the second antigen is MUC-1, WT-1, TRAIL/DR4Mage-A3-TCR, Mage-A4-TCR and/or Mage-A10.

In some aspects, the at least two antigen receptors, such as CAR and/or TCR, comprise one or more intracellular signaling domains. In particular aspects, the one or more intracellular signaling domains are T-lymphocyte activation domains. In some aspects, the one or more intracellular signaling domains comprise CD3ξ, CD28, OX40/CD134, 4-1BB/CD137, FcεRIγ, ICOS/CD278, ILRB/CD122, IL-2RG/CD132, DAP12, CD70, CD40, or a combination thereof. In some aspects, the one or more intracellular signaling domains comprise CD3, CD28, 4-1BB-L, DAP10 and/or DAP12. In specific aspects, the at least two antigen receptors, such as CAR and/or TCR, comprise one or more transmembrane domains. In some aspects, the one or transmembrane domains comprise CD28 transmembrane domain, IgG4Fc hinge, Fc regions, CD4 transmembrane domain, the CD3ξ transmembrane domain, cysteine mutated human CD3 domain, CD16 transmembrane domain, CD8 transmembrane domain, and/or erythropoietin receptor transmembrane domain. In some aspects, DNA encoding the at least two antigen receptors, such as CAR and/or TCR, is integrated into the genome of the cell.

A further embodiment provides a pharmaceutical composition comprising an effective amount of an immune cell of the embodiments (e.g., expressing at least two antigen receptors, such as CAR and/or TCR). In another embodiment, there is provided a composition comprising an effective amount of an immune cell of an immune cell of the embodiments (e.g., expressing at least two antigen receptors, such as CAR and/or TCR) for the treatment of an immune-related disorder in a subject. In another embodiment there is provided a method of treating an immune-related disorder in a subject comprising administering an effective amount of immune cells of the embodiments (e.g., expressing at least two antigen receptors, such as CAR and/or TCR) to the subject.

In some aspects, the immune-related disorder is a cancer, autoimmune disorder, graft versus host disease, allograft rejection, or inflammatory condition. In certain aspects, the immune-related disorder is an inflammatory condition and the immune cells have essentially no expression of glucocorticoid receptor. In some aspects, the subject has been or is being administered a steroid therapy. In some aspects, the immune cells are autologous. In certain aspects, the immune cells are allogeneic.

In certain aspects, the immune-related disorder is a cancer. In particular aspects, the cancer is a solid cancer or a hematologic malignancy. In some aspects, the cancer is ovarian cancer and the immune cells have antigenic specificity for MUC-1, CA-125, and/or WT-1. In certain aspects, the cancer is lung cancer and the immune cells have antigenic specificity for NY-ESO, EGFR-vIII, Mage-A3, Mage-A4, Mage-A10, and/or TRAIL/DR4. In specific aspects, the cancer is pancreatic cancer or colon cancer and the immune cells have antigenic specificity for Mage-A3, Mage-A4, Mage-A10, and/or CEA. In some aspects, the cancer is breast cancer and the immune cells have antigenic specificity for MUC-1 and HER2/Neu. In certain aspects, the cancer is glioblastoma and the immune cells have antigenic specificity for Mage-A3, Mage-A4, Mage-A10v, and/or EGFRvIII. In some aspects, the cancer is sarcoma and the immune cells have antigenic specificity for NY-ESO and EGFR-vIII.

In additional aspects, the method further comprises administering at least a second therapeutic agent. In some aspects, the at least a second therapeutic agent comprises chemotherapy, immunotherapy, surgery, radiotherapy, or biotherapy. In certain aspects, the immune cells and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Flow cytometry of CAR expression in NK cells from 2 different donors. (FIG. 1B) iC9/CAR.CS1/IL-15-transduced NK cells exert superior killing of CS1-expressing myeloma cell lines. (FIG. 1C) iC9/CAR.CS1/IL-15-transduced NK cells produce more effector cytokines in response to CS1-expressing myeloma cell lines.

(FIG. 4A) Annexin V expression is shown after 4 hours of dexamethasone treatment in NK cells from 3 different donors. (FIG. 4B) Annexin V expression is shown after 24 hours of dexamethasone treatment in NK cells from 3 different donors. All cells were dead at 24 hours of 500 µM dexamethasone treatment.

(FIG. 6A) Successful knockout of TGFβ-RII using CRISPR/CAS9 technology (Cas9 plus gRNA targeting of Exon 3 of TGFβ-RII). (FIG. 6B) Wild type and TGF-β-RII knockout NK cells were treated with 10 ng/ml of recombinant TGF-β for 48 hrs and their response to K562 targets was assessed. TGF-β-RII knockout NK cells are resistant to the immunosuppressive effect of exogenous TGF-β. (FIG. 6C) TGFβ-RII knockout by CRISPR/CAS9 technology abrogates downstream Smad-2/3 phosphorylation in response to 10n g/ml of recombinant TGF-β compared to NK cells treated with CAS9 alone.

(FIG. 7A) Schematic depicting immune cells, such as NK cell, with two CARs and hIL-15 expression. (FIG. 7B) Schematic depicting immune cell, such as NK cell, with a CAR, TCR, and hIL-15 expression. (FIG. 7C) Schematic depicting immune cell, such as NK cell, with two TCRs and hIL-15 expression. (FIG. 7D) Schematic of constructs expressing CAR-CAR, TCR-CAR, or TCR-TCR and hIL-15.

DESCRIPTION OF ILLUSTRATIVE EMBODIMENTS

Figure 7A:
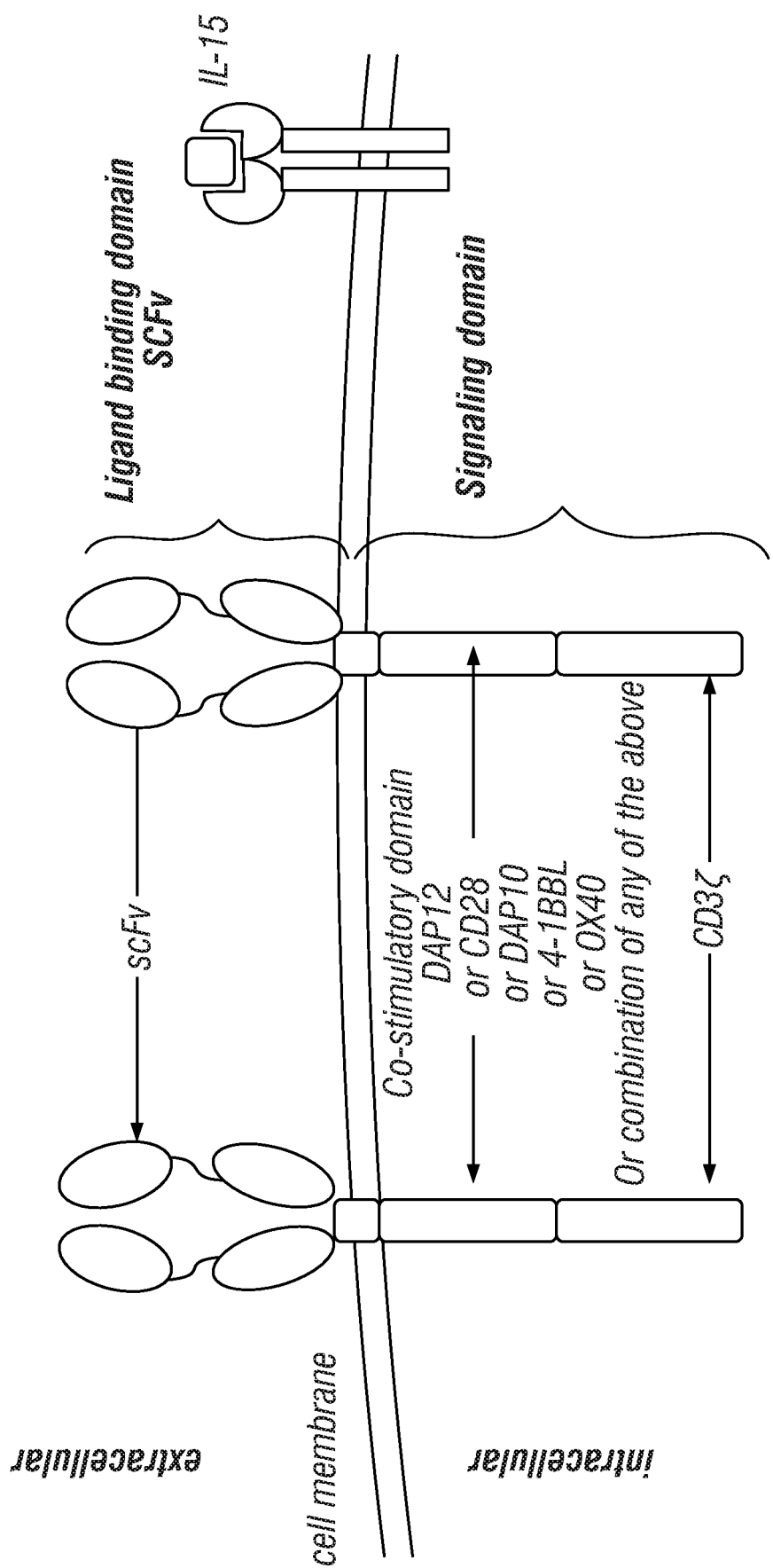
FIGS. 7A-7D.
Figure 7B:
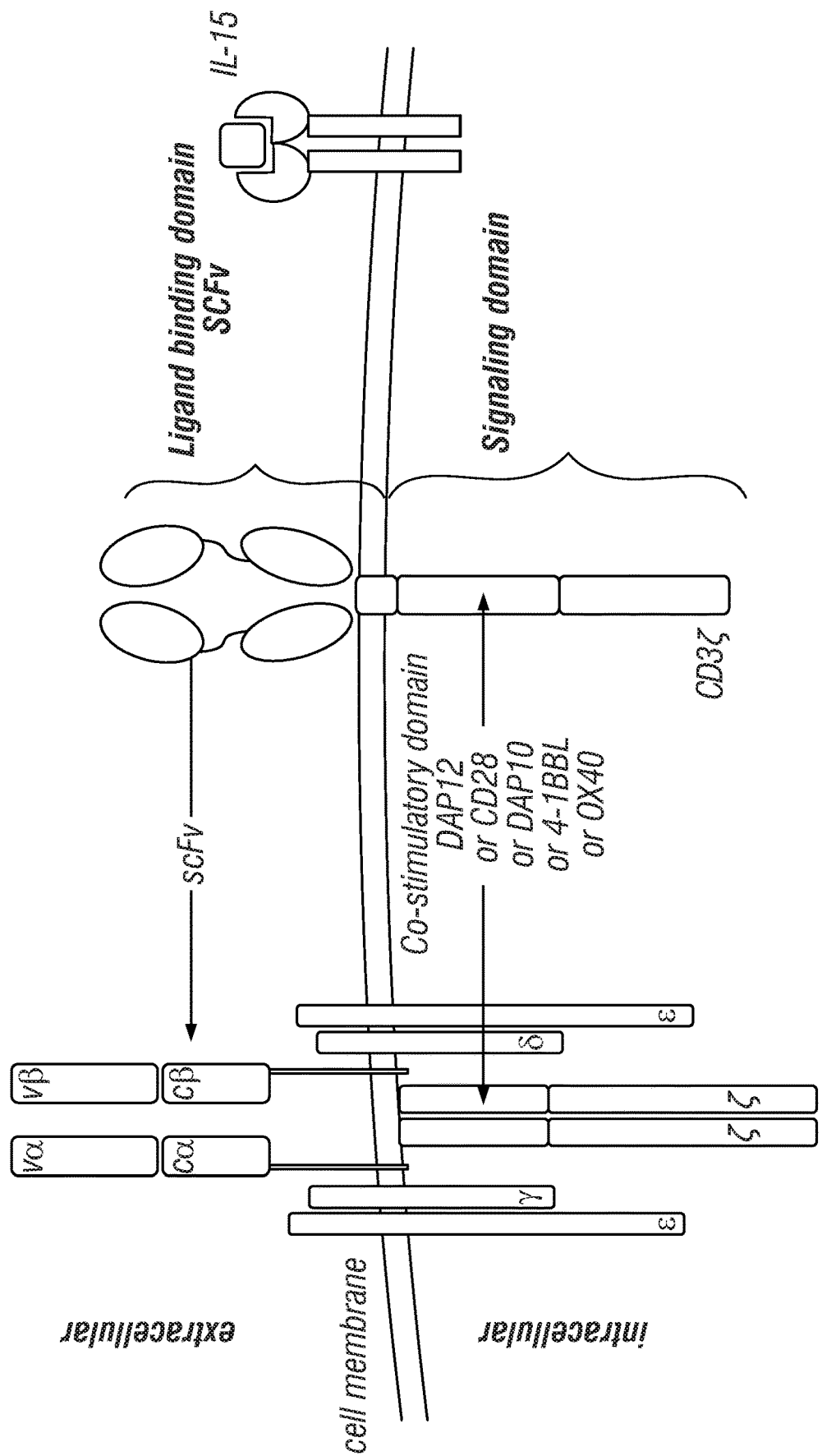
Figure 7C:
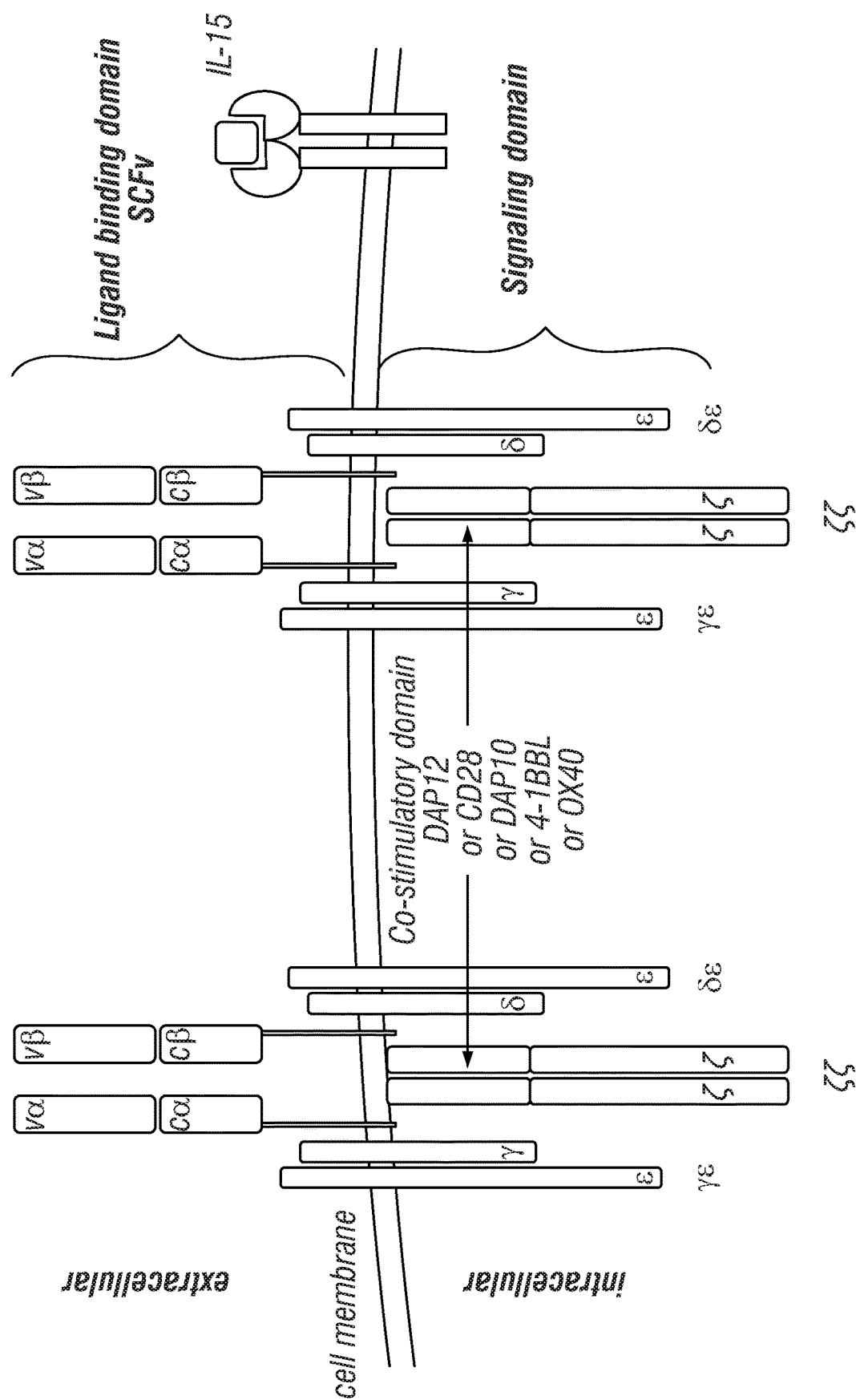
Figure 7D:
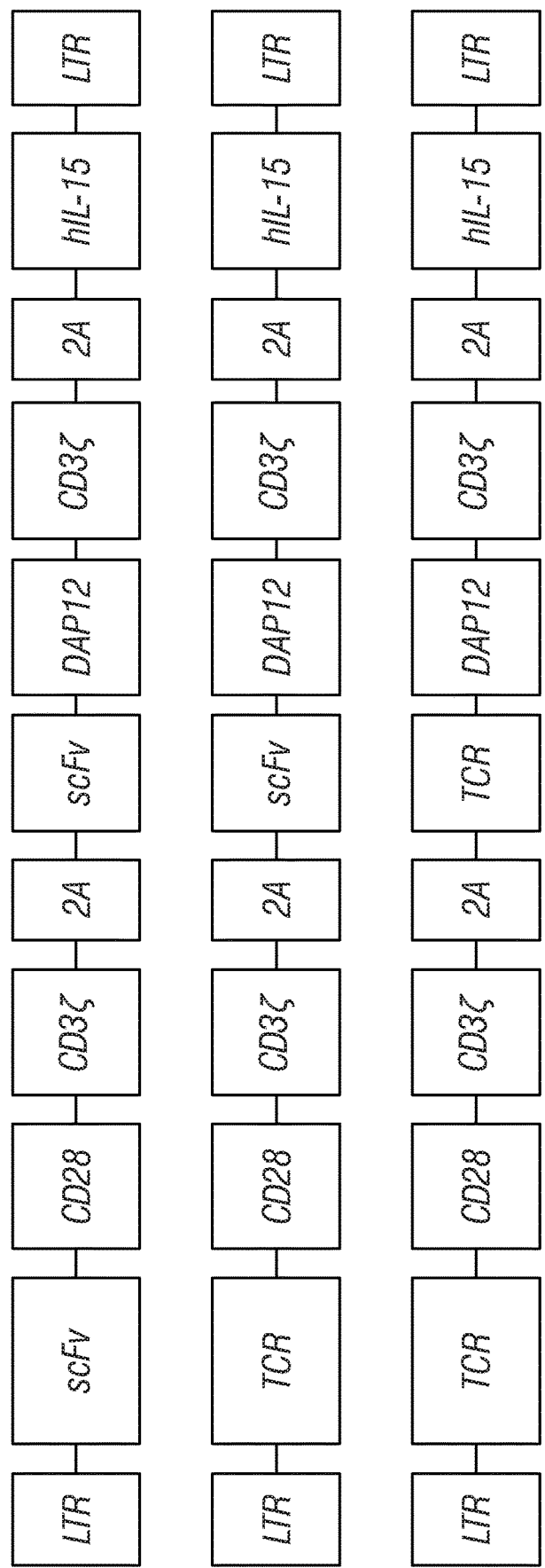

The present disclosure overcomes problems associated with current technologies by providing antigen-specific immune cells (e.g., T cells and NK cells) for immunotherapy, such as for the treatment of immune-related diseases, including cancer and autoimmune disorders, as well as infection including but not limited to viruses, such as CMV, EBV, and HIV. In one embodiment, the present disclosure provides NK cells which express one or more T cell receptors (TCRs). To enhance signaling, the TCR transduced in NK cells may be linked to a signaling domain. In contrast to conventional antibody-directed target antigens, antigens recognized by the TCR can include the entire array of potential intracellular proteins, which are processed and delivered to the cell surface as a peptide/MHC complex. As NK cells do not express endogenous TCR, the introduction of high affinity TCRs in NK cells results in redirection of their antigen specificity without the risk of generating mixed dimers as seen with T cells which express exogenous and endogenous TCRs. To generate a more potent receptor that functions optimally in NK cells, the receptor may have a costimulatory domain (including but not limited to CD28, 41BB ligand, DAP12, DAP10 or any combination of these), as well as a CD3 signaling domain in the vector (FIG. 7D). Thus, the present disclosure also provides methods for application of NK cell immunotherapy to target antigens derived from tumors and pathogens that are normally only recognized by T cells. Further, unlike T cells, NK cells from an allogeneic source do not increase the risk of inducing graft-versus-host disease; thus, the use of allogeneic NK cells with TCRs provide a potential source of TCR-engineered NK cells for adoptive therapy.

Moreover, the present disclosure further provides immune cells, such as NK cells and T cells, comprising at least two antigen receptors, such as a combination of CAR and TCR, two CARs, or two TCRs, for dual targeting of tumors. This method of putting both multiple antigen receptors, such as both TCR and CAR, into a single cell type allows for the targeting of two or more antigens using two completely different mechanisms of antigen recognition, including surface antigen recognition via CAR and peptide/MHC complex recognition through the TCR. To allow for the enhanced in vivo persistence of NK cells, the cells may be engineered to express IL-15 or another cytokine such as IL21, IL15 or IL-18. Thus, the cells may express two CARs, one CAR+ one TCR, two TCRs, or any combinations of CARs and TCRs which may further express IL-15 or other cytokines. This method also allows for reduction in the risk of antigen-negative tumor escape. The immune cells may be derived from several sources including peripheral blood, cord blood, bone marrow, stem cells, induced pluripotent stem cells (iPSC cells), and NK cell lines, such as, but not limited to, the NK-92 cell line.

Further embodiments concern the targeting of the glucocorticoid receptor (GR), the TGFβ receptor 2 (TGFβRII), and/or the immune checkpoint gene CISH by gene editing to enhance the potency of immune cells, such as the CAR- and/or TCR-engineered immune cells. In particular, targeting GR renders the immune cells resistant to the lymphocytotoxic effect of corticosteroids and targeting of TGFβRII renders them resistant to the immunosuppressive tumor microenvironment. For example, the immune cells may be engineered to be steroid-resistant, and/or TGFB-resistant using the CRISPR-CAS system or other gene editing systems such as TALEN or zinc finger nucleases.

In addition, the antigenic receptors used in the present disclosure may contain IL15, such as human IL-15, or other supportive cytokines including, but not limited, to IL-21, IL-18 or IL-2. The antigenic receptor construct (TCR or CAR) can further include co-stimulatory molecules such as CD3ζ, 4-1BB-L, DAP12, DAP10, or other costimulatory molecules. While the immune cells of the present disclosure may be targeted to any combination of antigens, exemplary antigens for the CAR and/or TCR include but are not limited to CS1, BCMA, CD38, CD19, CD123, CD33, CD99, CLL1, ROR1, CD5, CD7, mesothelin and ROR1. In particular aspects, the immune cells are dually targeted to an antigen combination including CD19-CAR and TCR against EBNA peptide (e.g., for EBV lymphoma); WT1 and CD123 (e.g., for the treatment of myeloid malignancies (e.g., AML, MDS, CML)); CD19 and ROR1 (for the treatment of CLL or mantle cell lymphoma); NY-ESO TCR plus EGFRvIII—NK-CAR (e.g., for sarcoma and lung cancer); Muc-1-TCR and Her-2-neu-NK-CAR (e.g., for breast cancer); Muc-1-TCR and CA-125-NK-CAR (e.g., for ovarian cancer); WT1-TCR and CA-125-NK-CAR (e.g., for ovarian cancer); Mage-A3-TCR, Mage-A4-TCR or Mage-A10-TCR plus EGFRVII-NK-CAR (e.g., for lung cancer and glioblastoma); TRAIL/DR4-TCR plus EGFRv3-CAR (e.g., for lung cancer); and Mage-A3-TCR, Mage-A4-TCR or Mage-A10-TCR plus CEA-CAR (e.g., for colon cancer and pancreas cancer).

In further embodiments, immune cells, particularly NK cells, are transduced with a vector carrying two CARs (e.g., CD99 and CD33, or CD123 and CD33, or CD19 and ROR1, or CD38 and BCMA or CS1 or other combinations) to provide dual specificity to the immune cell and IL-15 or another cytokine to enhance their in vivo persistence. This method provides increased specificity of NK-CARs by limiting the off-target toxicity, such that a signal is only given to NK cells to kill when both antigens are expressed on the tumor, as well as enhanced in vivo proliferation and persistence. Thus, normal cells that express only one antigen will not be targeted. This strategy is applicable to any subset of immune cells including, but not limited to, NK cells, T cells, gamma delta T cells, and iNKT cells.

Genetic reprogramming of immune cells, such as NK cells and T cells, for adoptive cancer immunotherapy has clinically relevant applications and benefits such as 1) innate anti-tumor surveillance without prior need for sensitization 2) allogeneic efficacy without graft versus host reactivity in the case of NK cells and 3) direct cell-mediated cytotoxicity and cytolysis of target tumors. Accordingly, the present disclosure also provides methods for treating immune-related disorders, such as cancer, comprising adoptive cell immunotherapy with any of the engineered immune cells provided herein.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells, or is otherwise flanked by a different nucleic acid sequence than that found in nature.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extrachromosomal DNA molecule separate from the chromosomal DNA that is capable of replicating independently of the chromosomal DNA. In certain cases, it is circular and double-stranded.

An "origin of replication" ("ori") or "replication origin" is a DNA sequence, e.g., in a lymphotrophic herpes virus, that when present in a plasmid in a cell is capable of maintaining linked sequences in the plasmid and/or a site at or near where DNA synthesis initiates. As an example, an ori for EBV (Ebstein-Barr virus) includes FR sequences (20 imperfect copies of a 30 bp repeat), and preferably DS sequences; however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, methods of the present disclosure may also use genetically engineered replication origin of EBV, such as by insertion or mutation of individual elements.

A "gene," "polynucleotide," "coding region," "sequence," "segment," "fragment," or "transgene" that "encodes" a particular protein, is a nucleic acid molecule that is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites (IRES), enhancers, splice junctions, and the like, which collectively provide for the replication, transcription, post-transcriptional processing, and translation of a coding sequence in a recipient cell. Not all of these control elements need be present so long as the selected coding sequence is capable of being replicated, transcribed, and translated in an appropriate host cell.

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3' direction) coding sequence. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

By "enhancer" is meant a nucleic acid sequence that, when positioned proximate to a promoter, confers increased transcription activity relative to the transcription activity resulting from the promoter in the absence of the enhancer domain.

By "operably linked" or co-expressed" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" or "co-expressed" with reference to peptide and/or polypeptide molecules means that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that promote the formation of stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPSCs or iPS cells".

An "embryonic stem (ES) cell" is an undifferentiated pluripotent cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

"Induced pluripotent stem cells (iPSCs or iPS cells)" are cells generated by reprogramming a somatic cell by expressing or inducing expression of a combination of factors (herein referred to as reprogramming factors). iPS cells can be generated using fetal, postnatal, newborn, juvenile, or adult somatic cells. In certain embodiments, factors that can be used to reprogram somatic cells to pluripotent stem cells include, for example, Oct4 (sometimes referred to as Oct3/4), Sox2, c-Myc, Klf4, Nanog, and Lin28. In some embodiments, somatic cells are reprogrammed by expressing at least two reprogramming factors, at least three reprogramming factors, at least four reprogramming factors, at least five reprogramming factors, at least six reprogramming factors, or at least seven reprogramming factors to reprogram a somatic cell to a pluripotent stem cell.

"Hematopoietic progenitor cells" or "hematopoietic precursor cells" refers to cells which are committed to a hematopoietic lineage but are capable of further hematopoietic differentiation and include hematopoietic stem cells, multipotential hematopoietic stem cells, common myeloid progenitors, megakaryocyte progenitors, erythrocyte progenitors, and lymphoid progenitors. Hematopoietic stem cells (HSCs) are multipotent stem cells that give rise to all the blood cell types including myeloid (monocytes and macrophages, granulocytes (neutrophils, basophils, eosinophils, and mast cells), erythrocytes, megakaryocytes/platelets, dendritic cells), and lymphoid lineages (T-cells, B-cells, NK-cells) (see e.g., Doulatov et al., 2012; Notta et al., 2015). A "multilymphoid progenitor" (MLP) is defined to describe any progenitor that gives rise to all lymphoid lineages (B, T, and NK cells), but that may or may not have other (myeloid) potentials (Doulatov et al., 2010) and is $CD45RA^+$, $/CD10^+/CD7^-$. Any B, T, and NK progenitor can be referred to as an MLP. A "common myeloid progenitor" (CMP) refers to $CD45RA^-/CD135+/CD10^-/CD7^-$ cells that can give rise to granulocytes, monocytes, megakaryocytes and erythrocytes.

"Pluripotent stem cell" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system).

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

"Programming" is a process that alters the type of progeny a cell can produce. For example, a cell has been programmed when it has been altered so that it can form progeny of at least one new cell type, either in culture or in vivo, as compared to what it would have been able to form under the same conditions without programming. This means that after sufficient proliferation, a measurable proportion of progeny having phenotypic characteristics of the new cell type are observed, if essentially no such progeny could form before programming; alternatively, the proportion having characteristics of the new cell type is measurably more than before programming. This process includes differentiation, dedifferentiation and transdifferentiation.

"Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Typically, transdifferentiation by programming occurs without the cells passing through an intermediate pluripotency stage—i.e., the cells are programmed directly from one differentiated cell type to another differentiated cell type. Under certain conditions, the proportion of progeny with characteristics of the new cell type may be at least about 1%, 5%, 25% or more in order of increasing preference.

As used herein, the term "subject" or "subject in need thereof" refers to a mammal, preferably a human being, male or female at any age that is in need of a cell or tissue transplantation. Typically the subject is in need of cell or tissue transplantation (also referred to herein as recipient)

due to a disorder or a pathological or undesired condition, state, or syndrome, or a physical, morphological or physiological abnormality which is amenable to treatment via cell or tissue transplantation.

As used herein, a "disruption" or "alteration" of a gene refers to the elimination or reduction of expression of one or more gene products encoded by the subject gene in a cell, compared to the level of expression of the gene product in the absence of the alteration. Exemplary gene products include mRNA and protein products encoded by the gene. Alteration in some cases is transient or reversible and in other cases is permanent. Alteration in some cases is of a functional or full length protein or mRNA, despite the fact that a truncated or non-functional product may be produced. In some embodiments herein, gene activity or function, as opposed to expression, is disrupted. Gene alteration is generally induced by artificial methods, i.e., by addition or introduction of a compound, molecule, complex, or composition, and/or by alteration of nucleic acid of or associated with the gene, such as at the DNA level. Exemplary methods for gene alteration include gene silencing, knockdown, knockout, and/or gene alteration techniques, such as gene editing. Examples include antisense technology, such as RNAi, siRNA, shRNA, and/or ribozymes, which generally result in transient reduction of expression, as well as gene editing techniques which result in targeted gene inactivation or alteration, e.g., by induction of breaks and/or homologous recombination. Examples include insertions, mutations, and deletions. The alterations typically result in the repression and/or complete absence of expression of a normal or "wild type" product encoded by the gene. Exemplary of such gene alterations are insertions, frameshift and missense mutations, deletions, knock-in, and knock-out of the gene or part of the gene, including deletions of the entire gene. Such alterations can occur in the coding region, e.g., in one or more exons, resulting in the inability to produce a full-length product, functional product, or any product, such as by insertion of a stop codon. Such alterations may also occur by alterations in the promoter or enhancer or other region affecting activation of transcription, so as to prevent transcription of the gene. Gene alterations include gene targeting, including targeted gene inactivation by homologous recombination.

An "immune disorder," "immune-related disorder," or "immune-mediated disorder" refers to a disorder in which the immune response plays a key role in the development or progression of the disease. Immune-mediated disorders include autoimmune disorders, allograft rejection, graft versus host disease and inflammatory and allergic conditions.

An "immune response" is a response of a cell of the immune system, such as a B cell, or a T cell, or innate immune cell to a stimulus. In one embodiment, the response is specific for a particular antigen (an "antigen-specific response").

As used herein, the term "antigen" is a molecule capable of being bound by an antibody or T-cell receptor. An antigen may generally be used to induce a humoral immune response and/or a cellular immune response leading to the production of B and/or T lymphocytes.

The terms "tumor-associated antigen," "tumor antigen" and "cancer cell antigen" are used interchangeably herein. In each case, the terms refer to proteins, glycoproteins or carbohydrates that are specifically or preferentially expressed by cancer cells.

An "epitope" is the site on an antigen recognized by an antibody as determined by the specificity of the amino acid sequence. Two antibodies are said to bind to the same epitope if each competitively inhibits (blocks) binding of the other to the antigen as measured in a competitive binding assay. Alternatively, two antibodies have the same epitope if most amino acid mutations in the antigen that reduce or eliminate binding of one antibody reduce or eliminate binding of the other. Two antibodies are said to have overlapping epitopes if each partially inhibits binding of the other to the antigen, and/or if some amino acid mutations that reduce or eliminate binding of one antibody reduce or eliminate binding of the other.

An "autoimmune disease" refers to a disease in which the immune system produces an immune response (for example, a B-cell or a T-cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

The term "Graft-Versus-Host Disease (GVHD)" refers to a common and serious complication of bone marrow or other tissue transplantation wherein there is a reaction of donated immunologically competent lymphocytes against a transplant recipient's own tissue. GVHD is a possible complication of any transplant that uses or contains stem cells from either a related or an unrelated donor. In some embodiments, the GVHD is chronic GVHD (cGVHD).

A "parameter of an immune response" is any particular measurable aspect of an immune response, including, but not limited to, cytokine secretion (IL-6, IL-10, IFN-γ, etc.), chemokine secretion, altered migration or cell accumulation, immunoglobulin production, dendritic cell maturation, regulatory activity, number of immune cells and proliferation of any cell of the immune system. Another parameter of an immune response is structural damage or functional deterioration of any organ resulting from immunological attack. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. Similarly, an inhibition or decrease in a parameter of the immune response is a significant decrease in this parameter as compared to a control. Specific, non-limiting examples of a substantial decrease are at least about a 50% decrease, at least about a 75% decrease, at least about a 90% decrease, at least about a 100% decrease, at least about a 200% decrease, at least about a 300% decrease, and at least about a 500% decrease. A statistical test, such as a non-parametric ANOVA, or a T-test, can be used to compare differences in the magnitude of the response induced by one agent as compared to the percent of samples that respond using a second agent. In some examples, p≤0.05 is significant, and indicates that the chance that an increase or decrease in any observed parameter is due to random variation is less than 5%. One of skill in the art can readily identify other statistical assays of use.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "T cell" refers to T lymphocytes, and includes, but is not limited to, $\gamma:\delta+$ T cells, NK T cells, $CD4^+$ T cells and $CD8^+$ T cells. $CD4^+$ T cells include $T_H0$, $T_H1$ and $T_H2$ cells, as well as regulatory T cells ($T_{reg}$). There are at least three types of regulatory T cells: $CD4^+$ $CD25^+$ $T_{reg}$, $CD25$ $T_H3$ $T_{reg}$, and $CD25$ $T_R1$ $T_{reg}$. "Cytotoxic T cell" refers to a T cell that can kill another cell. The majority of cytotoxic T cells are $CD8^+$ MHC class I-restricted T cells, however some cytotoxic T cells are $CD4^+$. In preferred embodiments, the T cell of the present disclosure is $CD4^+$ or $CD8^+$.

The activation state of a T cell defines whether the T cell is "resting" (i.e., in the $G_0$ phase of the cell cycle) or "activated" to proliferate after an appropriate stimulus such as the recognition of its specific antigen, or by stimulation with OKT3 antibody, PHA or PMA, etc. The "phenotype" of the T cell (e.g., naïve, central memory, effector memory, lytic effectors, help effectors ($T_H1$ and $T_H2$ cells), and regulatory effectors), describes the function the cell exerts when activated. A healthy donor has T cells of each of these phenotypes, and which are predominately in the resting state. A naïve T cell will proliferate upon activation, and then differentiate into a memory T cell or an effector T cell. It can then assume the resting state again, until it gets activated the next time, to exert its new function and may change its phenotype again. An effector T cell will divide upon activation and antigen-specific effector function.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP10, DAP12 and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

The term "antigen presenting cells (APCs)" refers to a class of cells capable of presenting one or more antigens in the form of peptide-MHC complex recognizable by specific effector cells of the immune system, and thereby inducing an effective cellular immune response against the antigen or antigens being presented. APCs can be intact whole cells such as macrophages, B cells, endothelial cells, activated T cells, and dendritic cells; or other molecules, naturally occurring or synthetic, such as purified MHC Class I molecules complexed to β2-microglobulin. While many types of cells may be capable of presenting antigens on their cell surface for T cell recognition, only dendritic cells have the capacity to present antigens in an efficient amount to activate naive T cells for cytotoxic T-lymphocyte (CTL) responses.

The term "culturing" refers to the in vitro maintenance, differentiation, and/or propagation of cells in suitable media. By "enriched" is meant a composition comprising cells present in a greater percentage of total cells than is found in the tissues where they are present in an organism.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

II. IMMUNE CELLS

Certain embodiments of the present disclosure concern immune cells which express a chimeric antigen receptor (CAR) and/or a T cell receptor (TCR). The immune cells may be T cells (e.g., regulatory T cells, CD4+ T cells, CD8+ T cells, or gamma-delta T cells), NK cells, invariant NK cells, NKT cells, stem cells (e.g., mesenchymal stem cells (MSCs) or induced pluripotent stem (iPSC) cells). In some embodiments, the cells are monocytes or granulocytes, e.g., myeloid cells, macrophages, neutrophils, dendritic cells, mast cells, eosinophils, and/or basophils. Also provided herein are methods of producing and engineering the immune cells as well as methods of using and administering the cells for adoptive cell therapy, in which case the cells may be autologous or allogeneic. Thus, the immune cells may be used as immunotherapy, such as to target cancer cells.

The immune cells may be isolated from subjects, particularly human subjects. The immune cells can be obtained from a subject of interest, such as a subject suspected of having a particular disease or condition, a subject suspected of having a predisposition to a particular disease or condition, or a subject who is undergoing therapy for a particular disease or condition. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the immune cells are isolated from blood, such as peripheral blood or cord blood. In some aspects, immune cells isolated from cord blood have enhanced immunomodulation capacity, such as measured by CD4- or CD8-positive T cell suppression. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune cell activity. Thus, the cells will be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in said subject or donor. The immune cells can be isolated from a pool of subjects and/or donors, such as from pooled cord blood.

When the population of immune cells is obtained from a donor distinct from the subject, the donor is preferably allogeneic, provided the cells obtained are subject-compatible in that they can be introduced into the subject. Allogeneic donor cells are may or may not be human-leukocyte-antigen (HLA)-compatible. To be rendered subject-compatible, allogeneic cells can be treated to reduce immunogenicity.

A. T Cells

In some embodiments, the immune cells are T cells. Several basic approaches for the derivation, activation and expansion of functional anti-tumor effector cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor TCR; and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

In some embodiments, the T cells are derived from the blood, bone marrow, lymph, umbilical cord, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4$^+$ and/or CD8$^+$ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ T cells are further enriched for or depleted of naive, central memory, effector memory, and/or central memory stem cells, such as by positive or negative selection based on surface antigens associated with the respective subpopulation.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2).

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, in the presence of a T-cell growth factor, such as 300 IU/ml IL-2 or IL-15, with IL-2 being preferred. The in vitro-induced T cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

The autologous T-cells can be modified to express a T-cell growth factor that promotes the growth and activation of the autologous T-cells. Suitable T-cell growth factors include, for example, interleukin (IL)-2, IL-7, IL-15, and IL-12. Suitable methods of modification are known in the art. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. In particular aspects, modified autologous T cells express the T cell growth factor at high levels. T cell growth factor coding sequences, such as that of IL-12, are readily available in the art, as are promoters, the operable linkage of which to a T-cell growth factor coding sequence promote high-level expression.

B. NK Cells

In some embodiments, the immune cells are NK cells. NK cells are a subpopulation of lymphocytes that have spontaneous cytotoxicity against a variety of tumor cells, virus-infected cells, and some normal cells in the bone marrow and thymus. NK cells are critical effectors of the early innate immune response toward transformed and virus-infected cells. NK cells constitute about 10% of the lymphocytes in human peripheral blood. When lymphocytes are cultured in the presence of IL-2, strong cytotoxic reactivity develops. NK cells are effector cells known as large granular lymphocytes because of their larger size and the presence of characteristic azurophilic granules in their cytoplasm. NK cells differentiate and mature in the bone marrow, lymph nodes, spleen, tonsils, and thymus. NK cells can be detected by specific surface markers, such as CD16, CD56, and CD8 in humans. NK cells do not express T cell antigen receptors, the pan T marker CD3, or surface immunoglobulin B cell receptors.

Stimulation of NK cells is achieved through a cross-talk of signals derived from cell surface activating and inhibitory receptors. The activation status of NK cells is regulated by a balance of intracellular signals received from an array of germ-line-encoded activating and inhibitory receptors (Campbell, 2006). When NK cells encounter an abnormal cell (e.g., tumor or virus-infected cell) and activating signals predominate, the NK cells can rapidly induce apoptosis of the target cell through directed secretion of cytolytic granules containing perforin and granzymes or engagement of death domain-containing receptors. Activated NK cells can also secrete type I cytokines, such as interferon-γ, tumor necrosis factor-α and granulocyte-macrophage colony-stimulating factor (GM-CSF), which activate both innate and adaptive immune cells as well as other cytokines and chemokines (Wu et al., 2003). Production of these soluble factors by NK cells in early innate immune responses significantly influences the recruitment and function of other hematopoietic cells. Also, through physical contacts and production of cytokines, NK cells are central players in a regulatory crosstalk network with dendritic cells and neutrophils to promote or restrain immune responses.

In certain embodiments, NK cells are derived from human peripheral blood mononuclear cells (PBMC), unstimulated leukapheresis products (PBSC), human embryonic stem cells (hESCs), induced pluripotent stem cells (iPSCs), bone marrow, or umbilical cord blood by methods well known in the art. Particularly, umbilical CB is used to derive NK cells. In certain aspects, the NK cells are isolated and expanded by the previously described method of ex vivo expansion of NK cells (Shah et al., 2013). In this method, CB mononuclear cells are isolated by ficoll density gradient centrifugation and cultured in a bioreactor with IL-2 and artificial antigen presenting cells (aAPCs). After 7 days, the cell culture is depleted of any cells expressing CD3 and re-cultured for an additional 7 days. The cells are again CD3-depleted and characterized to determine the percentage of $CD56^+/CD3^-$ cells or NK cells. In other methods, umbilical CB is used to derive NK cells by the isolation of $CD34^+$ cells and differentiation into $CD56^+/CD3^-$ cells by culturing in medium contain SCF, IL-7, IL-15, and IL-2.

C. Stem Cells

In some embodiments, the immune cells of the present disclosure may be stem cells, such as induced pluripotent stem cells (PSCs), mesenchymal stem cells (MSCs), or hematopoietic stem cells (HSCs).

The pluripotent stem cells used herein may be induced pluripotent stem (iPS) cells, commonly abbreviated iPS cells or iPSCs. The induction of pluripotency was originally achieved in 2006 using mouse cells (Yamanaka et al. 2006) and in 2007 using human cells (Yu et al. 2007; Takahashi et al. 2007) by reprogramming of somatic cells via the introduction of transcription factors that are linked to pluripotency. The use of iPSCs circumvents most of the ethical and practical problems associated with large-scale clinical use of ES cells, and patients with iPSC-derived autologous transplants may not require lifelong immunosuppressive treatments to prevent graft rejection.

With the exception of germ cells, any cell can be used as a starting point for iPSCs. For example, cell types could be keratinocytes, fibroblasts, hematopoietic cells, mesenchymal cells, liver cells, or stomach cells. There is no limitation on the degree of cell differentiation or the age of an animal from which cells are collected; even undifferentiated progenitor cells (including somatic stem cells) and finally differentiated mature cells can be used as sources of somatic cells in the methods disclosed herein.

Somatic cells can be reprogrammed to produce iPS cells using methods known to one of skill in the art. One of skill in the art can readily produce iPS cells, see for example, Published U.S. Patent Application No. 2009/0246875, Published U.S. Patent Application No. 2010/0210014; Published U.S. Patent Application No. 2012/0276636; U.S. Pat. Nos. 8,058,065; 8,129,187; PCT Publication NO. WO 2007/069666 A1, U.S. Pat. Nos. 8,268,620; 8,546,140; 9,175,268; 8,741,648; U.S. Patent Application No. 2011/0104125, and U.S. Pat. No. 8,691,574, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 are utilized or Oct3/4, Sox2, Nanog, and Lin28.

Mouse and human cDNA sequences of these nuclear reprogramming substances are available with reference to the NCBI accession numbers mentioned in WO 2007/069666 and U.S. Pat. No. 8,183,038, which are incorporated herein by reference. Methods for introducing one or more reprogramming substances, or nucleic acids encoding these reprogramming substances, are known in the art, and disclosed for example, in U.S. Pat. Nos. 8,268,620, 8,691,574, 8,741,648, 8,546,140, in published U.S. Pat. Nos. 8,900,871 and 8,071,369, which are both incorporated herein by reference.

Once derived, iPSCs can be cultured in a medium sufficient to maintain pluripotency. The iPSCs may be used with various media and techniques developed to culture pluripotent stem cells, more specifically, embryonic stem cells, as described in U.S. Pat. No. 7,442,548 and U.S. Patent Pub. No. 2003/0211603. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF. Other methods for the culture and maintenance of iPSCs, as would be known to one of skill in the art, may be used with the methods disclosed herein.

In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium or E8™/Essential 8™ medium.

Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in *E. coli*, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments, plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. In particular aspects, the plasmids do not comprise a tyrosinase enhancer or promoter. There are numerous plasmid vectors that are known in the art for inducing a nucleic acid encoding a protein. These include, but are not limited to, the vectors disclosed in U.S. Pat. Nos.

6,103,470; 7,598,364; 7,989,425; and 6,416,998, and U.S. application Ser. No. 12/478,154 which are incorporated herein by reference.

An episomal gene delivery system can be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or a lentiviral vector. A viral gene delivery system can be an RNA-based or DNA-based viral vector.

D. Genetically Engineered Antigen Receptors

The immune cells (e.g., autologous or allogeneic T cells (e.g., regulatory T cells, $CD4^+$ T cells, $CD8^+$ T cells, or gamma-delta T cells), NK cells, invariant NK cells, NKT cells, stem cells (e.g., MSCs or iPS cells) can be genetically engineered to express antigen receptors such as engineered TCRs and/or CARs. For example, the host cells (e.g, autologous or allogeneic T-cells) are modified to express a TCR having antigenic specificity for a cancer antigen. In particular embodiments, NK cells are engineered to express a TCR. The NK cells may be further engineered to express a CAR. Multiple CARs and/or TCRs, such as to different antigens, may be added to a single cell type, such as T cells or NK cells.

Suitable methods of modification are known in the art. See, for instance, Sambrook and Ausubel, supra. For example, the cells may be transduced to express a TCR having antigenic specificity for a cancer antigen using transduction techniques described in Heemskerk et al., 2008 and Johnson et al., 2009.

Electroporation of RNA coding for the full length TCR α and β (or γ and δ) chains can be used as alternative to overcome long-term problems with autoreactivity caused by pairing of retrovirally transduced and endogenous TCR chains. Even if such alternative pairing takes place in the transient transfection strategy, the possibly generated autoreactive T cells will lose this autoreactivity after some time, because the introduced TCR α and β chain are only transiently expressed. When the introduced TCR α and β chain expression is diminished, only normal autologous T cells are left. This is not the case when full length TCR chains are introduced by stable retroviral transduction, which will never lose the introduced TCR chains, causing a constantly present autoreactivity in the patient.

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., 2013; Davila et al., 2013; Turtle et al., 2012; Wu et al., 2012. In some aspects, the genetically engineered antigen receptors include a CAR as described in U.S. Pat. No. 7,446,190, and those described in International Patent Application Publication No.: WO/2014055668 A1.

1. Chimeric Antigen Receptors

In some embodiments, the CAR comprises: a) an intracellular signaling domain, b) a transmembrane domain, and c) an extracellular domain comprising an antigen binding region.

In some embodiments, the engineered antigen receptors include CARs, including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

Certain embodiments of the present disclosure concern the use of nucleic acids, including nucleic acids encoding an antigen-specific CAR polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be human genes used to enhance cellular immunotherapy for human patients. In a specific embodiment, the invention includes a full-length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, DAP12, and 4-1BB (CD137). In addition to a primary signal initiated by CD3ζ, an additional signal provided by a human costimulatory receptor inserted in a human CAR is important for full activation of NK cells and could help improve in vivo persistence and the therapeutic success of the adoptive immunotherapy.

In some embodiments, CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In certain embodiments of the chimeric antigen receptor, the antigen-specific portion of the receptor (which may be referred to as an extracellular domain comprising an antigen binding region) comprises a tumor associated antigen or a pathogen-specific antigen binding domain. Antigens include carbohydrate antigens recognized by pattern-recognition receptors, such as Dectin-1. A tumor associated antigen may be of any kind so long as it is expressed on the cell surface of tumor cells. Exemplary embodiments of tumor associated antigens include CD19, CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, and so forth. In certain embodiments, the CAR may be co-expressed with a cytokine to improve persistence when there is a low amount of tumor-associated antigen. For example, CAR may be co-expressed with IL-15.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into immune cells. Suitable vectors for use in accordance with the method of the present disclosure are non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD16, CD22, CD33, CD37, CD64, CD80, CD86, CD 134, CD137, CD154, ICOS/CD278, GITR/CD357, NKG2D, and DAP molecules. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

In certain embodiments, the platform technologies disclosed herein to genetically modify immune cells, such as NK cells, comprise (i) non-viral gene transfer using an electroporation device (e.g., a nucleofector), (ii) CARs that signal through endodomains (e.g., CD28/CD3-ζ, CD137/CD3-ζ, or other combinations), (iii) CARs with variable lengths of extracellular domains connecting the antigen-recognition domain to the cell surface, and, in some cases, (iv) artificial antigen presenting cells (aAPC) derived from K562 to be able to robustly and numerically expand CAR$^+$ immune cells (Singh et al., 2008; Singh et al., 2011).

2. T Cell Receptor (TCR)

In some embodiments, the genetically engineered antigen receptors include recombinant TCRs and/or TCRs cloned from naturally occurring T cells. A "T cell receptor" or "TCR" refers to a molecule that contains a variable α and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form.

Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable α chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., 1990; Chothia et al., 1988; Lefranc et al., 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., α-chain, β-chain) can contain two immunoglobulin domains, a variable domain (e.g., $V_a$ or Vp; typically amino acids 1 to 116 based on Kabat numbering Kabat et al., "Sequences of Proteins of Immunological Interest, US Dept. Health and Human Services, Public Health Service National Institutes of Health, 1991, $5^{th}$ ed.) at the N-terminus, and one constant domain (e.g., a-chain constant domain or $C_a$, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T cell hybridomas or other publicly available source. In some embodiments, the T cells can be obtained from in vivo isolated cells. In some embodiments, a high-affinity T cell clone can be isolated from a patient, and the TCR isolated. In some embodiments, the T cells can be a cultured T cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al., 2009 and Cohen et al., 2005). In some embodiments, phage display is used to isolate TCRs against a target antigen (see, e.g., Varela-Rohena et al., 2008 and Li, 2005). In some embodiments, the TCR or antigen-binding portion thereof can be synthetically generated from knowledge of the sequence of the TCR.

3. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The MHC is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

In some cases, aAPCs are useful in preparing therapeutic compositions and cell therapy products of the embodiments. For general guidance regarding the preparation and use of antigen-presenting systems, see, e.g., U.S. Pat. Nos. 6,225, 042, 6,355,479, 6,362,001 and 6,790,662; U.S. Patent Application Publication Nos. 2009/0017000 and 2009/0004142; and International Publication No. WO2007/103009.

aAPC systems may comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD86, CD64 (FcγRI), 41BB ligand, and IL-21. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), which promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

4. Interleukin-15

Interleukin-15 (IL-15) is tissue restricted and only under pathologic conditions is it observed at any level in the serum, or systemically. IL-15 possesses several attributes that are desirable for adoptive therapy. IL-15 is a homeostatic cytokine that induces development and cell proliferation of natural killer cells, promotes the eradication of established tumors via alleviating functional suppression of tumor-resident cells, and inhibits AICD.

In one embodiments, the present disclosure concerns co-modifying CAR and/or TCR immune cells with IL-15. In addition to IL-15, other cytokines are envisioned. These include, but are not limited to, cytokines, chemokines, and other molecules that contribute to the activation and proliferation of cells used for human application. NK or T cells expressing IL-15 are capable of continued supportive cytokine signaling, which is critical to their survival post-infusion.

In certain embodiments, K562 aAPC were developed, expressing the desired antigen (e.g., CD19) along with costimulatory molecules, such as CD28, IL-15, and CD3ζ, to select for immune cells (e.g., NK cells) in vitro that are capable of sustained CAR-mediated propagation. This powerful technology allows the manufacture of clinically relevant numbers (up to $10^{10}$) of CAR$^+$ NK cells suitable for human application. As needed, additional stimulation cycles can be undertaken to generate larger numbers of genetically modified NK cells. Typically, at least 90% of the propagated NK cells express CAR and can be cryopreserved for infusion. Furthermore, this approach can be harnessed to generate NK cells to diverse tumor types by pairing the specificity of the introduced CAR with expression of the tumor-associated antigen (TAA) recognized by the CAR on the aAPC.

Following genetic modification the cells may be immediately infused or may be stored. In certain aspects, following genetic modification, the cells may be propagated for days, weeks, or months ex vivo as a bulk population within about 1, 2, 3, 4, 5 days or more following gene transfer into cells. In a further aspect, the transfectants are cloned and a clone demonstrating presence of a single integrated or episomally maintained expression cassette or plasmid, and expression of the chimeric receptor is expanded ex vivo. The clone selected for expansion demonstrates the capacity to specifically recognize and lyse CD19 expressing target cells. The recombinant immune cells may be expanded by stimulation with IL-2, or other cytokines that bind the common gamma-chain (e.g., IL-7, IL-12, IL-15, IL-21, and others). The recombinant immune cells may be expanded by stimulation with artificial antigen presenting cells. In a further aspect, the genetically modified cells may be cryopreserved.

5. Antigens

Among the antigens targeted by the genetically engineered antigen receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas. In some embodiments, the antigen is selectively expressed or over-expressed on cells of the disease or condition, e.g., the tumor or pathogenic cells, as compared to normal or non-targeted cells or tissues. In other embodiments, the antigen is expressed on normal cells and/or is expressed on the engineered cells.

Any suitable antigen may find use in the present method. Exemplary antigens include, but are not limited to, antigenic molecules from infectious agents, auto-/self-antigens, tumor-/cancer-associated antigens, and tumor neoantigens (Linnemann et al., 2015). In particular aspects, the antigens include NY-ESO, EGFRvIII, Muc-1, Her2, CA-125, WT-1, Mage-A3, Mage-A4, Mage-A10, TRAIL/DR4, and CEA. In particular aspects, the antigens for the two or more antigen receptors include, but are not limited to, CD19, EBNA, WT1, CD123, NY-ESO, EGFRvIII, MUC1, HER2, CA-125, WT1, Mage-A3, Mage-A4, Mage-A10, TRAIL/DR4, and/or CEA. The sequences for these antigens are known in the art, for example, CD19 (Accession No. NG_007275.1), EBNA (Accession No. NG_002392.2), WT1 (Accession No. NG_009272.1), CD123 (Accession No. NC_000023.11), NY-ESO (Accession No. NC_000023.11), EGFRvIII (Accession No. NG_007726.3), MUC1 (Accession No. NG_029383.1), HER2 (Accession No. NG_007503.1), CA-125 (Accession No. NG_055257.1), WT1 (Accession No. NG_009272.1), Mage-A3 (Accession No. NG_013244.1), Mage-A4 (Accession No. NG_013245.1), Mage-A10 (Accession No. NC_000023.11), TRAIL/DR4 (Accession No. NC_000003.12), and/or CEA (Accession No. NC_000019.10).

Tumor-associated antigens may be derived from prostate, breast, colorectal, lung, pancreatic, renal, mesothelioma, ovarian, or melanoma cancers. Exemplary tumor-associated antigens or tumor cell-derived antigens include MAGE 1, 3, and MAGE 4 (or other MAGE antigens such as those disclosed in International Patent Publication No. WO99/40188); PRAME; BAGE; RAGE, Lage (also known as NY ESO 1); SAGE; and HAGE or GAGE. These non-limiting examples of tumor antigens are expressed in a wide range of tumor types such as melanoma, lung carcinoma, sarcoma, and bladder carcinoma. See, e.g., U.S. Pat. No. 6,544,518. Prostate cancer tumor-associated antigens include, for example, prostate specific membrane antigen (PSMA), prostate-specific antigen (PSA), prostatic acid phosphates, NKX3.1, and six-transmembrane epithelial antigen of the prostate (STEAP).

Other tumor associated antigens include Plu-1, HASH-1, HasH-2, Cripto and Criptin. Additionally, a tumor antigen may be a self peptide hormone, such as whole length gonadotrophin hormone releasing hormone (GnRH), a short 10 amino acid long peptide, useful in the treatment of many cancers.

Tumor antigens include tumor antigens derived from cancers that are characterized by tumor-associated antigen expression, such as HER-2/neu expression. Tumor-associated antigens of interest include lineage-specific tumor antigens such as the melanocyte-melanoma lineage antigens MART-1/Melan-A, gp100, gp75, mda-7, tyrosinase and tyrosinase-related protein. Illustrative tumor-associated antigens include, but are not limited to, tumor antigens derived from or comprising any one or more of, p53, Ras, c-Myc, cytoplasmic serine/threonine kinases (e.g., A-Raf, B-Raf, and C-Raf, cyclin-dependent kinases), MAGE-A1, MAGE-A2, MAGE-A3, MAGE-A4, MAGE-A6, MAGE-A10, MAGE-A12, MART-1, BAGE, DAM-6, -10, GAGE-1, -2, -8, GAGE-3, -4, -5, -6, -7B, NA88-A, MART-1, MC1R, Gpl00, PSA, PSM, Tyrosinase, TRP-1, TRP-2, ART-4, CAMEL, CEA, Cyp-B, hTERT, hTRT, iCE, MUC1, MUC2, Phosphoinositide 3-kinases (PI3Ks), TRK receptors, PRAME, P15, RU1, RU2, SART-1, SART-3, Wilms' tumor antigen (WT1), AFP, -catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, receptor tyrosine kinases (e.g., Epidermal Growth Factor receptor (EGFR) (in particular, EGFRvIII), platelet derived growth factor receptor (PDGFR), vascular endothelial growth factor receptor (VEGFR)), cytoplasmic tyrosine kinases (e.g., src-family, syk-ZAP70 family), integrin-linked kinase (ILK), signal transducers and activators of transcription STAT3, STATS, and STATE, hypoxia inducible factors (e.g., HIF-1 and HIF-2), Nuclear Factor-Kappa B (NF-B), Notch receptors (e.g., Notchl-4), c-Met, mammalian targets of rapamycin (mTOR), WNT, extracellular signal-regulated kinases (ERKs), and their regulatory subunits, PMSA, PR-3, MDM2, Mesothelin, renal cell carcinoma-5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGsS, SART3, STn, PAX5, OY-TES1, sperm protein 17, LCK, HMWMAA, AKAP-4, SSX2, XAGE 1, B7H3, legumain, TIE2, Page4, MAD-CT-1, FAP, MAD-CT-2, fos related antigen 1, CBX2, CLDN6, SPANX, TPTE, ACTL8, ANKRD30A, CDKN2A, MAD2L1, CTAGiB, SUNC1, LRRN1 and idiotype.

Antigens may include epitopic regions or epitopic peptides derived from genes mutated in tumor cells or from genes transcribed at different levels in tumor cells compared to normal cells, such as telomerase enzyme, survivin, mesothelin, mutated ras, bcr/abl rearrangement, Her2/neu, mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; tumor antigens that include epitopic regions or epitopic peptides derived from oncoviral processes, such as human papilloma virus proteins E6 and E7; Epstein bar virus protein LMP2; nonmutated oncofetal proteins with a tumor-selective expression, such as carcinoembryonic antigen and alpha-fetoprotein.

In other embodiments, an antigen is obtained or derived from a pathogenic microorganism or from an opportunistic pathogenic microorganism (also called herein an infectious disease microorganism), such as a virus, fungus, parasite, and bacterium. In certain embodiments, antigens derived from such a microorganism include full-length proteins.

Illustrative pathogenic organisms whose antigens are contemplated for use in the method described herein include human immunodeficiency virus (HIV), herpes simplex virus (HSV), respiratory syncytial virus (RSV), cytomegalovirus (CMV), Epstein-Barr virus (EBV), Influenza A, B, and C, vesicular stomatitis virus (VSV), vesicular stomatitis virus (VSV), polyomavirus (e.g., BK virus and JC virus), adenovirus, Staphylococcus species including Methicillin-resistant Staphylococcus aureus (MRSA), and Streptococcus species including Streptococcus pneumoniae. As would be understood by the skilled person, proteins derived from these and other pathogenic microorganisms for use as antigen as described herein and nucleotide sequences encoding the proteins may be identified in publications and in public databases such as GENBANK®, SWISS-PROT®, and TREMBL®.

Antigens derived from human immunodeficiency virus (HIV) include any of the HIV virion structural proteins (e.g., gp120, gp41, p17, p24), protease, reverse transcriptase, or HIV proteins encoded by tat, rev, nef, vif, vpr and vpu.

Antigens derived from herpes simplex virus (e.g., HSV 1 and HSV2) include, but are not limited to, proteins expressed from HSV late genes. The late group of genes predominantly encodes proteins that form the virion particle. Such proteins include the five proteins from (UL) which form the viral capsid: UL6, UL18, UL35, UL38 and the major capsid protein UL19, UL45, and UL27, each of which may be used as an antigen as described herein. Other illustrative HSV proteins contemplated for use as antigens herein include the ICP27 (H1, H2), glycoprotein B (gB) and glycoprotein D (gD) proteins. The HSV genome comprises at least 74 genes, each encoding a protein that could potentially be used as an antigen.

Antigens derived from cytomegalovirus (CMV) include CMV structural proteins, viral antigens expressed during the immediate early and early phases of virus replication, glycoproteins I and III, capsid protein, coat protein, lower matrix protein pp65 (ppUL83), p52 (ppUL44), IE1 and IE2 (UL123 and UL122), protein products from the cluster of genes from UL128-UL150 (Rykman, et al., 2006), envelope glycoprotein B (gB), gH, gN, and pp150. As would be understood by the skilled person, CMV proteins for use as antigens described herein may be identified in public databases such as GENBANK®, SWISS-PROT®, and TREMBL® (see e.g., Bennekov et al., 2004; Loewendorf et al., 2010; Marschall et al., 2009).

Antigens derived from Epstein-Ban virus (EBV) that are contemplated for use in certain embodiments include EBV lytic proteins gp350 and gp110, EBV proteins produced during latent cycle infection including Epstein-Ban nuclear antigen (EBNA)-1, EBNA-2, EBNA-3A, EBNA-3B, EBNA-3C, EBNA-leader protein (EBNA-LP) and latent membrane proteins (LMP)-1, LMP-2A and LMP-2B (see, e.g., Lockey et al., 2008).

Antigens derived from respiratory syncytial virus (RSV) that are contemplated for use herein include any of the eleven proteins encoded by the RSV genome, or antigenic fragments thereof: NS 1, NS2, N (nucleocapsid protein), M (Matrix protein) SH, G and F (viral coat proteins), M2 (second matrix protein), M2-1 (elongation factor), M2 -2 (transcription regulation), RNA polymerase, and phosphoprotein P.

Antigens derived from Vesicular stomatitis virus (VSV) that are contemplated for use include any one of the five major proteins encoded by the VSV genome, and antigenic fragments thereof: large protein (L), glycoprotein (G), nucleoprotein (N), phosphoprotein (P), and matrix protein (M) (see, e.g., Rieder et al., 1999).

Antigens derived from an influenza virus that are contemplated for use in certain embodiments include hemagglutinin (HA), neuraminidase (NA), nucleoprotein (NP), matrix proteins M1 and M2, NS1, NS2 (NEP), PA, PB1, PB1-F2, and PB2.

Exemplary viral antigens also include, but are not limited to, adenovirus polypeptides, alphavirus polypeptides, calicivirus polypeptides (e.g., a calicivirus capsid antigen), coronavirus polypeptides, distemper virus polypeptides, Ebola virus polypeptides, enterovirus polypeptides, flavivirus polypeptides, hepatitis virus (AE) polypeptides (a hepatitis B core or surface antigen, a hepatitis C virus E1 or E2 glycoproteins, core, or non-structural proteins), herpesvirus polypeptides (including a herpes simplex virus or varicella zoster virus glycoprotein), infectious peritonitis virus polypeptides, leukemia virus polypeptides, Marburg virus polypeptides, orthomyxovirus polypeptides, papilloma virus polypeptides, parainfluenza virus polypeptides (e.g., the hemagglutinin and neuraminidase polypeptides), paramyxovirus polypeptides, parvovirus polypeptides, pestivirus polypeptides, picorna virus polypeptides (e.g., a poliovirus capsid polypeptide), pox virus polypeptides (e.g., a vaccinia virus polypeptide), rabies virus polypeptides (e.g., a rabies virus glycoprotein G), reovirus polypeptides, retrovirus polypeptides, and rotavirus polypeptides.

In certain embodiments, the antigen may be bacterial antigens. In certain embodiments, a bacterial antigen of interest may be a secreted polypeptide. In other certain embodiments, bacterial antigens include antigens that have a portion or portions of the polypeptide exposed on the outer cell surface of the bacteria.

Antigens derived from *Staphylococcus* species including Methicillin-resistant *Staphylococcus aureus* (MRSA) that are contemplated for use include virulence regulators, such as the Agr system, Sar and Sae, the Arl system, Sar homologues (Rot, MgrA, SarS, SarR, SarT, SarU, SarV, SarX, SarZ and TcaR), the Srr system and TRAP. Other *Staphylococcus* proteins that may serve as antigens include Clp proteins, HtrA, MsrR, aconitase, CcpA, SvrA, Msa, CfvA and CfvB (see, e.g., *Staphylococcus*: Molecular Genetics, 2008 Caister Academic Press, Ed. Jodi Lindsay). The genomes for two species of *Staphylococcus aureus* (N315 and Mu50) have been sequenced and are publicly available, for example at PATRIC (PATRIC: The VBI PathoSystems Resource Integration Center, Snyder et al., 2007). As would be understood by the skilled person, *Staphylococcus* proteins for use as antigens may also be identified in other public databases such as GenBank®, Swiss-Prot® and TrEMBL®.

Antigens derived from *Streptococcus pneumoniae* that are contemplated for use in certain embodiments described herein include pneumolysin, PspA, choline-binding protein A (CbpA), NanA, NanB, SpnHL, PavA, LytA, Pht, and pilin proteins (RrgA; RrgB; RrgC). Antigenic proteins of *Streptococcus pneumoniae* are also known in the art and may be used as an antigen in some embodiments (see, e.g., Zysk et al., 2000). The complete genome sequence of a virulent strain of *Streptococcus pneumoniae* has been sequenced and, as would be understood by the skilled person, *S. pneumoniae* proteins for use herein may also be identified in other public databases such as GENBANK®, SWISS-PROT®, and TREMBL®. Proteins of particular interest for antigens according to the present disclosure include virulence factors and proteins predicted to be exposed at the surface of the pneumococci (see, e.g., Frolet et al., 2010).

Examples of bacterial antigens that may be used as antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides (e.g., *B. burgdorferi* OspA), *Brucella* polypeptides, *Campylobacter* polypeptides, *Capnocytophaga* polypeptides, *Chlamydia* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides (e.g., *H. influenzae* type b outer membrane protein), *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides (i.e., *S. pneumoniae* polypeptides) (see description herein), *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, group A *streptococcus* polypeptides (e.g., *S. pyogenes* M proteins), group B *streptococcus* (*S. agalactiae*) polypeptides, *Treponema* polypeptides, and *Yersinia* polypeptides (e.g., *Y pestis* F1 and V antigens).

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammon-*

*dia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides. Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides. (e.g., *P. falciparum* circumsporozoite (PfCSP)), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of ectoparasite antigens include, but are not limited to, polypeptides (including antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

6. Suicide Genes

The CAR and/or TCR of the immune cells of the present disclosure may comprise one or more suicide genes. The term "suicide gene" as used herein is defined as a gene which, upon administration of a prodrug, effects transition of a gene product to a compound which kills its host cell. Examples of suicide gene/prodrug combinations which may be used are Herpes Simplex Virus-thymidine kinase (HSV-tk) and ganciclovir, acyclovir, or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

The *E. coli* purine nucleoside phosphorylase, a so-called suicide gene which converts the prodrug 6-methylpurine deoxyriboside to toxic purine 6-methylpurine. Other examples of suicide genes used with prodrug therapy are the *E. coli* cytosine deaminase gene and the HSV thymidine kinase gene.

Exemplary suicide genes include CD20, CD52, EGFRv3, or inducible caspase 9. In one embodiment, a truncated version of EGFR variant III (EGFRv3) may be used as a suicide antigen which can be ablated by Cetuximab. Further suicide genes known in the art that may be used in the present disclosure include Purine nucleoside phosphorylase (PNP), Cytochrome p450 enzymes (CYP), Carboxypeptidases (CP), Carboxylesterase (CE), Nitroreductase (NTR), Guanine Ribosyltransferase (XGRTP), Glycosidase enzymes, Methionine-α,γ-lyase (MET), and Thymidine phosphorylase (TP).

7. Methods of Delivery

One of skill in the art would be well-equipped to construct a vector through standard recombinant techniques (see, for example, Sambrook et al., 2001 and Ausubel et al., 1996, both incorporated herein by reference) for the expression of the antigen receptors of the present disclosure. Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors, parvovirus vectors, polio virus vectors, vesicular stomatitis virus vectors, maraba virus vectors and group B adenovirus enadenotucirev vectors.

a. Viral Vectors

Viral vectors encoding an antigen receptor may be provided in certain aspects of the present disclosure. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor mediated-endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Lentiviruses are complex retroviruses, which, in addition to the common retroviral genes gag, pol, and env, contain other genes with regulatory or structural function. Lentiviral vectors are well known in the art (see, for example, U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

b. Regulatory Elements

Expression cassettes included in vectors useful in the present disclosure in particular contain (in a 5'-to-3' direction) a eukaryotic transcriptional promoter operably linked to a protein-coding sequence, splice signals including intervening sequences, and a transcriptional termination/polyadenylation sequence. The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation. A promoter used in the context of the present disclosure includes constitutive, inducible, and tissue-specific promoters.

(i) Promoter/Enhancers

The expression constructs provided herein comprise a promoter to drive expression of the antigen receptor. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30110 bp—upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β lactamase (penicillinase), lactose and tryptophan (trp-) promoter systems. In addition to producing nucleic acid sequences of promoters and enhancers synthetically, sequences may be produced using recombinant cloning and/or nucleic acid amplification technology, including PCR™, in connection with the compositions disclosed herein. Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally, any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter, GADPH promoter, metallothionein promoter; and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). In certain embodiments, the promoter is CMV IE, dectin-1, dectin-2, human CD11c, F4/80, SM22, RSV, SV40, Ad MLP, beta-actin, MHC class I or MHC class II promoter, however any other promoter that is useful to drive expression of the therapeutic gene is applicable to the practice of the present disclosure.

In certain aspects, methods of the disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

(ii) Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Additionally, certain 2A sequence elements could be used to create linked- or co-expression of genes in the constructs provided in the present disclosure. For example, cleavage sequences could be used to co-express genes by linking open reading frames to form a single cistron. An exemplary cleavage sequence is the F2A (Foot-and-mouth diease virus 2A) or a "2A-like" sequence (e.g., Thosea asigna virus 2A; T2A).

(iii) Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

c. Selection and Screenable Markers

In some embodiments, cells containing a construct of the present disclosure may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

d. Other Methods of Nucleic Acid Delivery

In addition to viral delivery of the nucleic acids encoding the antigen receptor, the following are additional methods of recombinant gene delivery to a given host cell and are thus considered in the present disclosure.

Introduction of a nucleic acid, such as DNA or RNA, into the immune cells of the current disclosure may use any suitable methods for nucleic acid delivery for transformation of a cell, as described herein or as would be known to one of ordinary skill in the art. Such methods include, but are not limited to, direct delivery of DNA such as by ex vivo transfection, by injection, including microinjection); by electroporation; by calcium phosphate precipitation; by using DEAE-dextran followed by polyethylene glycol; by direct sonic loading; by liposome mediated transfection and receptor-mediated transfection; by microprojectile bombardment; by agitation with silicon carbide fibers; by *Agrobacterium*-mediated transformation; by desiccation/inhibition-mediated DNA uptake, and any combination of such methods. Through the application of techniques such as these, organelle(s), cell(s), tissue(s) or organism(s) may be stably or transiently transformed.

E. Modification of Gene Expression

In some embodiments, the immune cells of the present disclosure are modified to have altered expression of certain genes such as glucocorticoid receptor, TGFβ receptor (e.g., TGFβ-RII), and/or CISH. In one embodiment, the immune cells may be modified to express a dominant negative TGFβ receptor II (TGFβRIIDN) which can function as a cytokine sink to deplete endogenous TGFβ.

Cytokine signaling is essential for the normal function of hematopoietic cells. The SOCS family of proteins plays an important role in the negative regulation of cytokine signaling, acting as an intrinsic brake. CIS, a member of the SOCS family of proteins encoded by the CISH gene, has been identified as an important checkpoint molecule in NK cells in mice. Thus, in some embodiments, the present disclosure concerns the knockout of CISH in immune cells to improve cytotoxicity, such as in NK cells and $CD8^+$ T cells. This approach may be used alone or in combination with other checkpoint inhibitors to improve anti-tumor activity.

In some embodiments, the altered gene expression is carried out by effecting a disruption in the gene, such as a knock-out, insertion, missense or frameshift mutation, such as biallelic frameshift mutation, deletion of all or part of the gene, e.g., one or more exon or portion therefore, and/or knock-in. For example, the altered gene expression can be effected by sequence-specific or targeted nucleases, including DNA-binding targeted nucleases such as zinc finger nucleases (ZFN) and transcription activator-like effector nucleases (TALENs), and RNA-guided nucleases such as a CRISPR-associated nuclease (Cas), specifically designed to be targeted to the sequence of the gene or a portion thereof.

In some embodiments, the alteration of the expression, activity, and/or function of the gene is carried out by disrupting the gene. In some aspects, the gene is modified so that its expression is reduced by at least at or about 20, 30, or 40%, generally at least at or about 50, 60, 70, 80, 90, or 95% as compared to the expression in the absence of the gene modification or in the absence of the components introduced to effect the modification.

In some embodiments, the alteration is transient or reversible, such that expression of the gene is restored at a later time. In other embodiments, the alteration is not reversible or transient, e.g., is permanent.

In some embodiments, gene alteration is carried out by induction of one or more double-stranded breaks and/or one or more single-stranded breaks in the gene, typically in a targeted manner. In some embodiments, the double-stranded or single-stranded breaks are made by a nuclease, e.g. an endonuclease, such as a gene-targeted nuclease. In some aspects, the breaks are induced in the coding region of the gene, e.g. in an exon. For example, in some embodiments, the induction occurs near the N-terminal portion of the coding region, e.g. in the first exon, in the second exon, or in a subsequent exon.

In some aspects, the double-stranded or single-stranded breaks undergo repair via a cellular repair process, such as by non-homologous end-joining (NHEJ) or homology-directed repair (HDR). In some aspects, the repair process is error-prone and results in disruption of the gene, such as a frameshift mutation, e.g., biallelic frameshift mutation, which can result in complete knockout of the gene. For example, in some aspects, the disruption comprises inducing a deletion, mutation, and/or insertion. In some embodiments, the disruption results in the presence of an early stop codon. In some aspects, the presence of an insertion, deletion, translocation, frameshift mutation, and/or a premature stop codon results in disruption of the expression, activity, and/or function of the gene.

In some embodiments, gene alteration is achieved using antisense techniques, such as by RNA interference (RNAi), short interfering RNA (siRNA), short hairpin (shRNA), and/or ribozymes are used to selectively suppress or repress expression of the gene. siRNA technology is RNAi which employs a double-stranded RNA molecule having a sequence homologous with the nucleotide sequence of mRNA which is transcribed from the gene, and a sequence complementary with the nucleotide sequence. siRNA generally is homologous/complementary with one region of mRNA which is transcribed from the gene, or may be siRNA including a plurality of RNA molecules which are homologous/complementary with different regions. In some aspects, the siRNA is comprised in a polycistronic construct.

1. ZFPs and ZFNs

In some embodiments, the DNA-targeting molecule includes a DNA-binding protein such as one or more zinc finger protein (ZFP) or transcription activator-like protein (TAL), fused to an effector protein such as an endonuclease. Examples include ZFNs, TALEs, and TALENs.

In some embodiments, the DNA-targeting molecule comprises one or more zinc-finger proteins (ZFPs) or domains thereof that bind to DNA in a sequence-specific manner. A ZFP or domain thereof is a protein or domain within a larger protein that binds DNA in a sequence-specific manner through one or more zinc fingers, regions of amino acid sequence within the binding domain whose structure is stabilized through coordination of a zinc ion. The term zinc finger DNA binding protein is often abbreviated as zinc finger protein or ZFP. Among the ZFPs are artificial ZFP domains targeting specific DNA sequences, typically 9-18 nucleotides long, generated by assembly of individual fingers.

ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice.

In some embodiments, the DNA-targeting molecule is or comprises a zinc-finger DNA binding domain fused to a DNA cleavage domain to form a zinc-finger nuclease (ZFN). In some embodiments, fusion proteins comprise the cleavage domain (or cleavage half-domain) from at least one Type liS restriction enzyme and one or more zinc finger binding domains, which may or may not be engineered. In some embodiments, the cleavage domain is from the Type liS restriction endonuclease Fok I. Fok I generally catalyzes double-stranded cleavage of DNA, at 9 nucleotides from its recognition site on one strand and 13 nucleotides from its recognition site on the other.

Many gene-specific engineered zinc fingers are available commercially. For example, Sangamo Biosciences (Richmond, Calif., USA) has developed a platform (CompoZr) for zinc-finger construction in partnership with Sigma-Aldrich (St. Louis, Mo., USA), allowing investigators to bypass zinc-finger construction and validation altogether, and provides specifically targeted zinc fingers for thousands of proteins (Gaj et al., *Trends in Biotechnology*, 2013, 31(7), 397-405). In some embodiments, commercially available zinc fingers are used or are custom designed. (See, for example, Sigma-Aldrich catalog numbers CSTZFND, CSTZFN, CTil-1KT, and PZD0020).

2. TALs, TALEs and TALENs

In some embodiments, the DNA-targeting molecule comprises a naturally occurring or engineered (non-naturally occurring) transcription activator-like protein (TAL) DNA binding domain, such as in a transcription activator-like protein effector (TALE) protein, See, e.g., U.S. Patent Publication No. 2011/0301073, incorporated by reference in its entirety herein.

A TALE DNA binding domain or TALE is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Each TALE repeat unit includes 1 or 2 DNA-binding residues making up the Repeat Variable Diresidue (RVD), typically at positions 12 and/or 13 of the repeat. The natural (canonical) code for DNA recognition of these TALEs has been determined such that an HD sequence at positions 12 and 13 leads to a binding to cytosine (C), NG binds to T, NI to A, NN binds to G or A, and NO binds to T and non-canonical (atypical) RVDs are also known. In some embodiments, TALEs may be targeted to any gene by design of TAL arrays with specificity to the target DNA sequence. The target sequence generally begins with a thymidine.

In some embodiments, the molecule is a DNA binding endonuclease, such as a TALE nuclease (TALEN). In some aspects the TALEN is a fusion protein comprising a DNA-binding domain derived from a TALE and a nuclease catalytic domain to cleave a nucleic acid target sequence.

In some embodiments, the TALEN recognizes and cleaves the target sequence in the gene. In some aspects, cleavage of the DNA results in double-stranded breaks. In some aspects the breaks stimulate the rate of homologous recombination or non-homologous end joining (NHEJ). Generally, NHEJ is an imperfect repair process that often results in changes to the DNA sequence at the site of the cleavage. In some aspects, repair mechanisms involve rejoining of what remains of the two DNA ends through direct re-ligation or via the so-called microhomology-mediated end joining. In some embodiments, repair via NHEJ results in small insertions or deletions and can be used to disrupt and thereby repress the gene. In some embodiments, the modification may be a substitution, deletion, or addition of at least one nucleotide. In some aspects, cells in which a cleavage-induced mutagenesis event, i.e. a mutagenesis event consecutive to an NHEJ event, has occurred can be identified and/or selected by well-known methods in the art.

In some embodiments, TALE repeats are assembled to specifically target a gene. (Gaj et al., 2013). A library of TALENs targeting 18,740 human protein-coding genes has been constructed (Kim et al., 2013). Custom-designed TALE arrays are commercially available through Cellectis Bioresearch (Paris, France), Transposagen Biopharmaceuticals (Lexington, Ky., USA), and Life Technologies (Grand Island, N.Y., USA). Specifically, TALENs that target CD38 are commercially available (See Gencopoeia, catalog numbers HTN222870-1, HTN222870-2, and HTN222870-3). Exemplary molecules are described, e.g., in U.S. Patent Publication Nos. US 2014/0120622, and 2013/0315884.

In some embodiments the TALEN s are introduced as trans genes encoded by one or more plasmid vectors. In some aspects, the plasmid vector can contain a selection marker which provides for identification and/or selection of cells which received said vector.

3. RGENs (CRISPR/Cas Systems)

In some embodiments, the alteration is carried out using one or more DNA-binding nucleic acids, such as alteration via an RNA-guided endonuclease (RGEN). For example, the alteration can be carried out using clustered regularly interspaced short palindromic repeats (CRISPR) and CRISPR-associated (Cas) proteins. In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes*.

In some aspects, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The CRISPR system can induce double stranded breaks (DSBs) at the target site, followed by disruptions or alterations as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

The target sequence may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors.

When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2.

The CRISPR enzyme can be Cas9 (e.g., from S. pyogenes or S. pneumonia). The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Exemplary gRNA sequences for NR3CS (glucocorticoid receptor) include Ex3 NR3C1 sG1 5-TGC TGT TGA GGA GCT GGA-3 (SEQ ID NO:1) and Ex3 NR3C1 sG2 5-AGC ACA CCA GGC AGA GTT-3 (SEQ ID NO:2). Exemplary gRNA sequences for TGF-beta receptor 2 include EX3 TGFBR2 sG1 5-CGG CTG AGG AGC GGA AGA-3 (SEQ ID NO:3) and EX3 TGFBR2 sG2 5-TGG-AGG-TGA-GCA-ATC-CCC-3 (SEQ ID NO:4). The T7 promoter, target sequence, and overlap sequence may have the sequence TTAATACGACTCACTATAGG (SEQ ID NO:5)+target sequence+gttttagagctagaaatagc (SEQ ID NO:6).

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies), ELAND (Illumina, San Diego, Calif.), SOAP (available at soap.genomics.org.cn), and Maq (available at maq.sourceforge.net).

The CRISPR enzyme may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US 20110059502, incorporated herein by reference.

III. METHODS OF USE

In some embodiments, the present disclosure provides methods for immunotherapy comprising administering an effective amount of the immune cells of the present disclosure. In one embodiments, a medical disease or disorder is treated by transfer of an immune cell population that elicits an immune response. In certain embodiments of the present disclosure, cancer or infection is treated by transfer of an immune cell population that elicits an immune response. Provided herein are methods for treating or delaying progression of cancer in an individual comprising administering to the individual an effective amount an antigen-specific cell therapy. The present methods may be applied for the treatment of immune disorders, solid cancers, hematologic cancers, and viral infections.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

Particular embodiments concern methods of treatment of leukemia. Leukemia is a cancer of the blood or bone marrow and is characterized by an abnormal proliferation (production by multiplication) of blood cells, usually white blood cells (leukocytes). It is part of the broad group of diseases called hematological neoplasms. Leukemia is a broad term covering a spectrum of diseases. Leukemia is clinically and pathologically split into its acute and chronic forms.

In certain embodiments of the present disclosure, immune cells are delivered to an individual in need thereof, such as an individual that has cancer or an infection. The cells then enhance the individual's immune system to attack the respective cancer or pathogenic cells. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days.

Certain embodiments of the present disclosure provide methods for treating or preventing an immune-mediated disorder. In one embodiment, the subject has an autoimmune disease. Non-limiting examples of autoimmune diseases include: alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac spate-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, nephrotic syndrome (such as minimal change disease, focal glomerulosclerosis, or mebranous nephropathy), pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, Rheumatoid arthritis, sarcoidosis, scleroderma, Sjogren's syndrome, stiff-man syndrome, systemic lupus erythematosus, lupus erythematosus, ulcerative colitis, uveitis, vasculitides (such as polyarteritis nodosa, takayasu arteritis, temporal arteritis/giant cell arteritis, or dermatitis herpetiformis vasculitis), vitiligo, and Wegener's granulomatosis. Thus, some examples of an autoimmune disease that can be treated using the methods disclosed herein include, but are not limited to, multiple sclerosis, rheumatoid arthritis, systemic lupus erythematosis, type I diabetes mellitus, Crohn's disease; ulcerative colitis, myasthenia gravis, glomerulonephritis, ankylosing spondylitis, vasculitis, or psoriasis. The subject can also have an allergic disorder such as Asthma.

In yet another embodiment, the subject is the recipient of a transplanted organ or stem cells and immune cells are used to prevent and/or treat rejection. In particular embodiments, the subject has or is at risk of developing graft versus host disease. GVHD is a possible complication of any transplant that uses or contains stem cells from either a related or an unrelated donor. There are two kinds of GVHD, acute and chronic. Acute GVHD appears within the first three months following transplantation. Signs of acute GVHD include a reddish skin rash on the hands and feet that may spread and become more severe, with peeling or blistering skin. Acute GVHD can also affect the stomach and intestines, in which case cramping, nausea, and diarrhea are present. Yellowing of the skin and eyes (jaundice) indicates that acute GVHD has affected the liver. Chronic GVHD is ranked based on its severity: stage/grade 1 is mild; stage/grade 4 is severe. Chronic GVHD develops three months or later following transplantation. The symptoms of chronic GVHD are similar to those of acute GVHD, but in addition, chronic GVHD may also affect the mucous glands in the eyes, salivary glands in the mouth, and glands that lubricate the stomach lining and intestines. Any of the populations of immune cells disclosed herein can be utilized. Examples of a transplanted organ include a solid organ transplant, such as kidney, liver, skin, pancreas, lung and/or heart, or a cellular transplant such as islets, hepatocytes, myoblasts, bone marrow, or hematopoietic or other stem cells. The transplant can be a composite transplant, such as tissues of the face. Immune cells can be administered prior to transplantation, concurrently with transplantation, or following transplantation. In some embodiments, the immune cells are administered prior to the transplant, such as at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. In one specific, non-limiting example, administration of the therapeutically effective amount of immune cells occurs 3-5 days prior to transplantation.

In some embodiments, the subject can be administered nonmyeloablative lymphodepleting chemotherapy prior to the immune cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/m$^2$ fludarabine is administered for five days.

In certain embodiments, a growth factor that promotes the growth and activation of the immune cells is administered to the subject either concomitantly with the immune cells or subsequently to the immune cells. The immune cell growth factor can be any suitable growth factor that promotes the growth and activation of the immune cells. Examples of suitable immune cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of immune cells can be administered by a number of routes, including parenteral administration, for example, intravenous, intraperitoneal, intramuscular, intrasternal, or intraarticular injection, or infusion.

The therapeutically effective amount of immune cells for use in adoptive cell therapy is that amount that achieves a desired effect in a subject being treated. For instance, this can be the amount of immune cells necessary to inhibit advancement, or to cause regression of an autoimmune or alloimmune disease, or which is capable of relieving symptoms caused by an autoimmune disease, such as pain and inflammation. It can be the amount necessary to relieve symptoms associated with inflammation, such as pain, edema and elevated temperature. It can also be the amount necessary to diminish or prevent rejection of a transplanted organ.

The immune cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of immune cells will be dependent on the subject being treated, the severity and type of the affliction, and the manner of administration. In some embodiments, doses that could be used in the treatment of human subjects range from at least $3.8 \times 10^4$, at least $3.8 \times 10^5$, at least $3.8 \times 10^6$, at least $3.8 \times 10^7$, at least $3.8 \times 10^8$, at least $3.8 \times 10^9$, or at least $3.8 \times 10^{10}$ immune cells/m$^2$. In a certain embodiment, the dose used in the treatment of human subjects ranges from about $3.8\times10^9$ to about $3.8\times10^{10}$ immune cells/m$^2$. In additional embodiments, a therapeutically effective amount of immune cells can vary from about $5\times10^6$ cells per kg body weight to about $7.5\times10^8$ cells per kg body weight, such as about $2\times10^7$ cells to about $5\times10^8$ cells per kg body weight, or about $5\times10^7$ cells to about $2\times10^8$ cells per kg body weight. The exact amount of immune cells is readily determined by one of skill in the art based on the age, weight, sex, and physiological condition of the subject. Effective doses can be extrapolated from dose-response curves derived from in vitro or animal model test systems.

The immune cells may be administered in combination with one or more other therapeutic agents for the treatment of the immune-mediated disorder. Combination therapies can include, but are not limited to, one or more anti-microbial agents (for example, antibiotics, anti-viral agents and anti-fungal agents), anti-tumor agents (for example, fluorouracil, methotrexate, paclitaxel, fludarabine, etoposide, doxorubicin, or vincristine), immune-depleting agents (for example, fludarabine, etoposide, doxorubicin, or vincristine), immunosuppressive agents (for example, azathioprine, or glucocorticoids, such as dexamethasone or prednisone), anti-inflammatory agents (for example, glucocorticoids such as hydrocortisone, dexamethasone or prednisone, or non-steroidal anti-inflammatory agents such as acetylsalicylic acid, ibuprofen or naproxen sodium), cytokines (for example, interleukin-10 or transforming growth factor-beta), hormones (for example, estrogen), or a vaccine. In addition, immunosuppressive or tolerogenic agents including but not limited to calcineurin inhibitors (e.g., cyclosporin and tacrolimus); mTOR inhibitors (e.g., Rapamycin); mycophenolate mofetil, antibodies (e.g., recognizing CD3, CD4, CD40, CD154, CD45, IVIG, or B cells); chemotherapeutic agents (e.g., Methotrexate, Treosulfan, Busulfan); irradiation; or chemokines, interleukins or their inhibitors (e.g., BAFF, IL-2, anti-IL-2R, IL-4, JAK kinase inhibitors) can be administered. Such additional pharmaceutical agents can be administered before, during, or after administration of the immune cells, depending on the desired effect. This administration of the cells and the agent can be by the same route or by different routes, and either at the same site or at a different site.

A. Pharmaceutical Compositions

Also provided herein are pharmaceutical compositions and formulations comprising immune cells (e.g., T cells or NK cells) and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

B. Combination Therapies

In certain embodiments, the compositions and methods of the present embodiments involve an immune cell population in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

An immune cell therapy may be administered before, during, after, or in various combinations relative to an additional cancer therapy, such as immune checkpoint therapy. The administrations may be in intervals ranging from concurrently to minutes to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an immune cell therapy is "A" and an anti-cancer therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclophosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world.

Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer*, 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) Proc Natl Acad Sci USA 95(17): 10067-10071; Camacho et al. (2004) J Clin Oncology 22(145): Abstract No. 2505 (antibody CP-675206); and Mokyr et al. (1998) Cancer Res 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. ARTICLES OF MANUFACTURE OR KITS

An article of manufacture or a kit is provided comprising immune cells is also provided herein. The article of manufacture or kit can further comprise a package insert comprising instructions for using the immune cells to treat or delay progression of cancer in an individual or to enhance immune function of an individual having cancer. Any of the antigen-specific immune cells described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—CAR-NK Cells Expressing IL-15

Figure 1A:
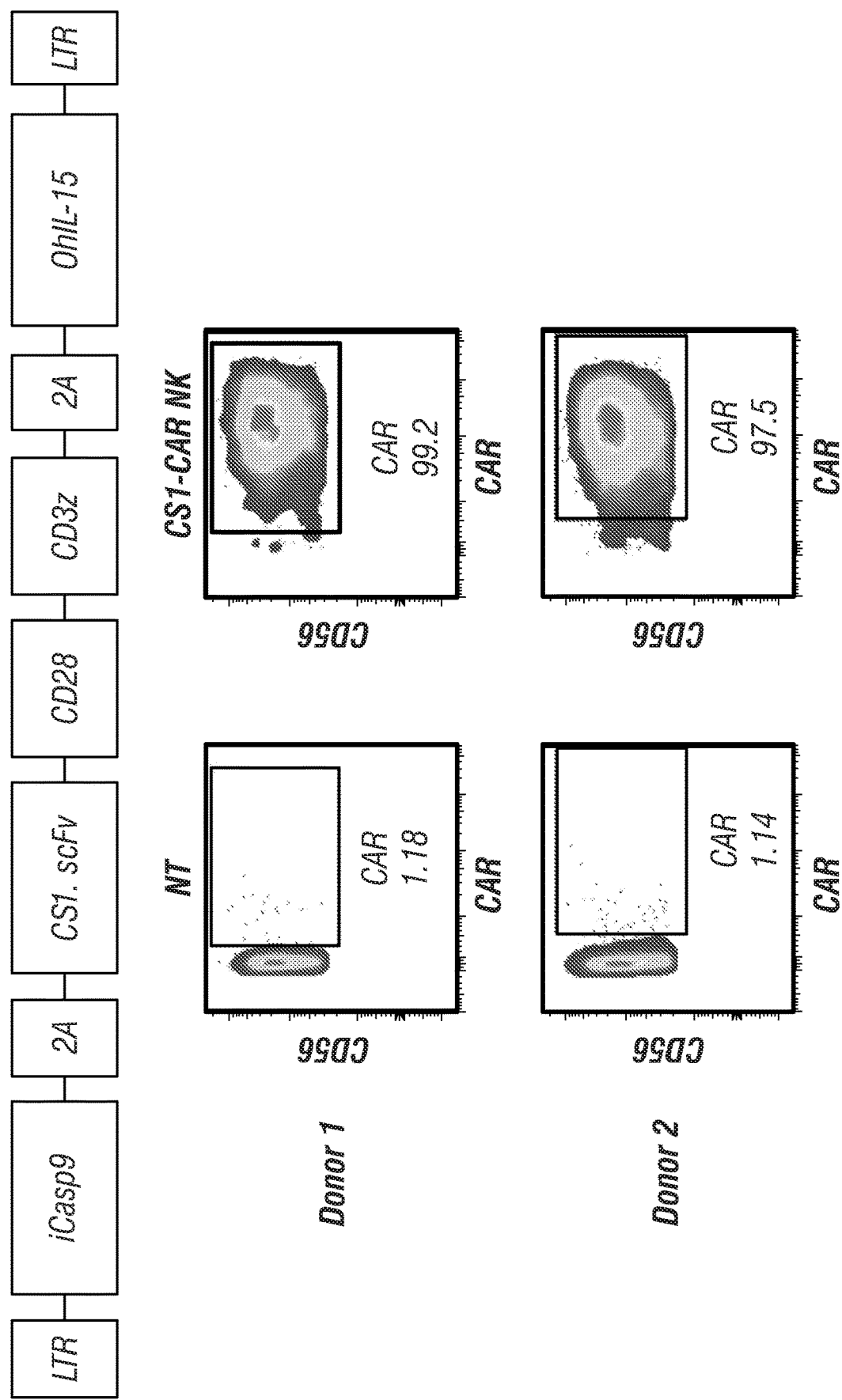
FIG. 1A-1C: Transduction efficiency of CS1 CAR in cord blood-derived NK cells.
Figure 1B:
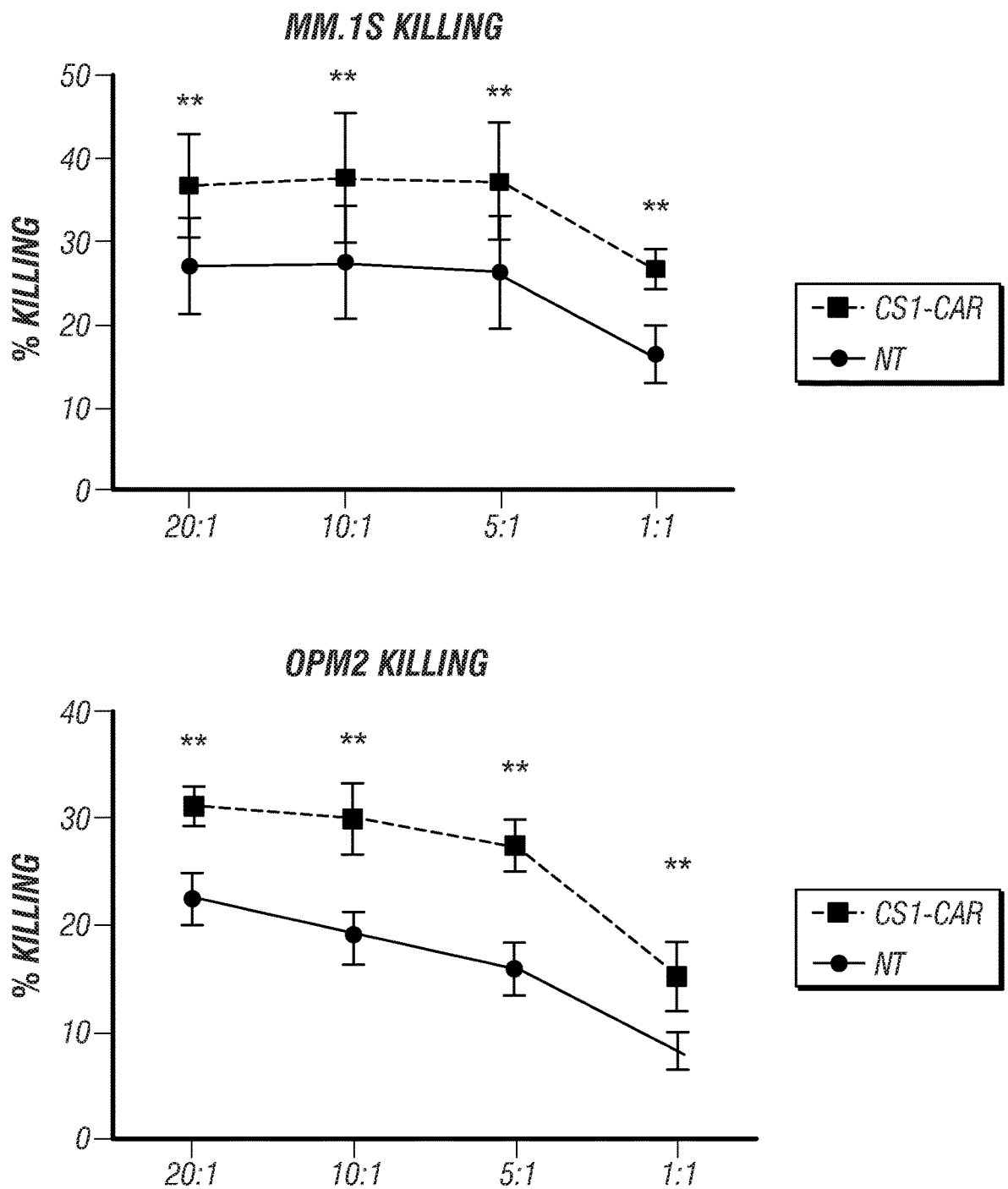
Figure 1C:
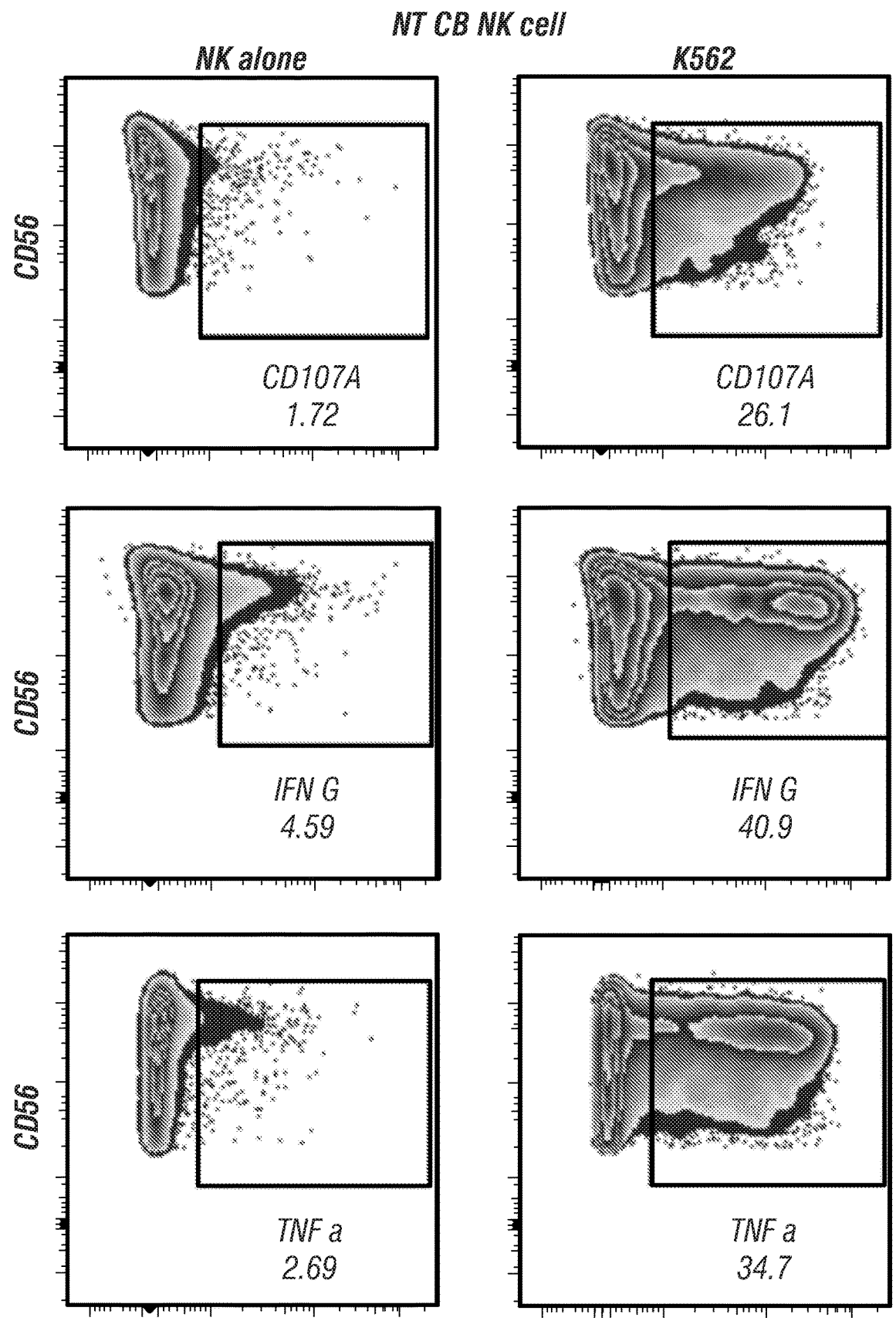
Figure 1C:
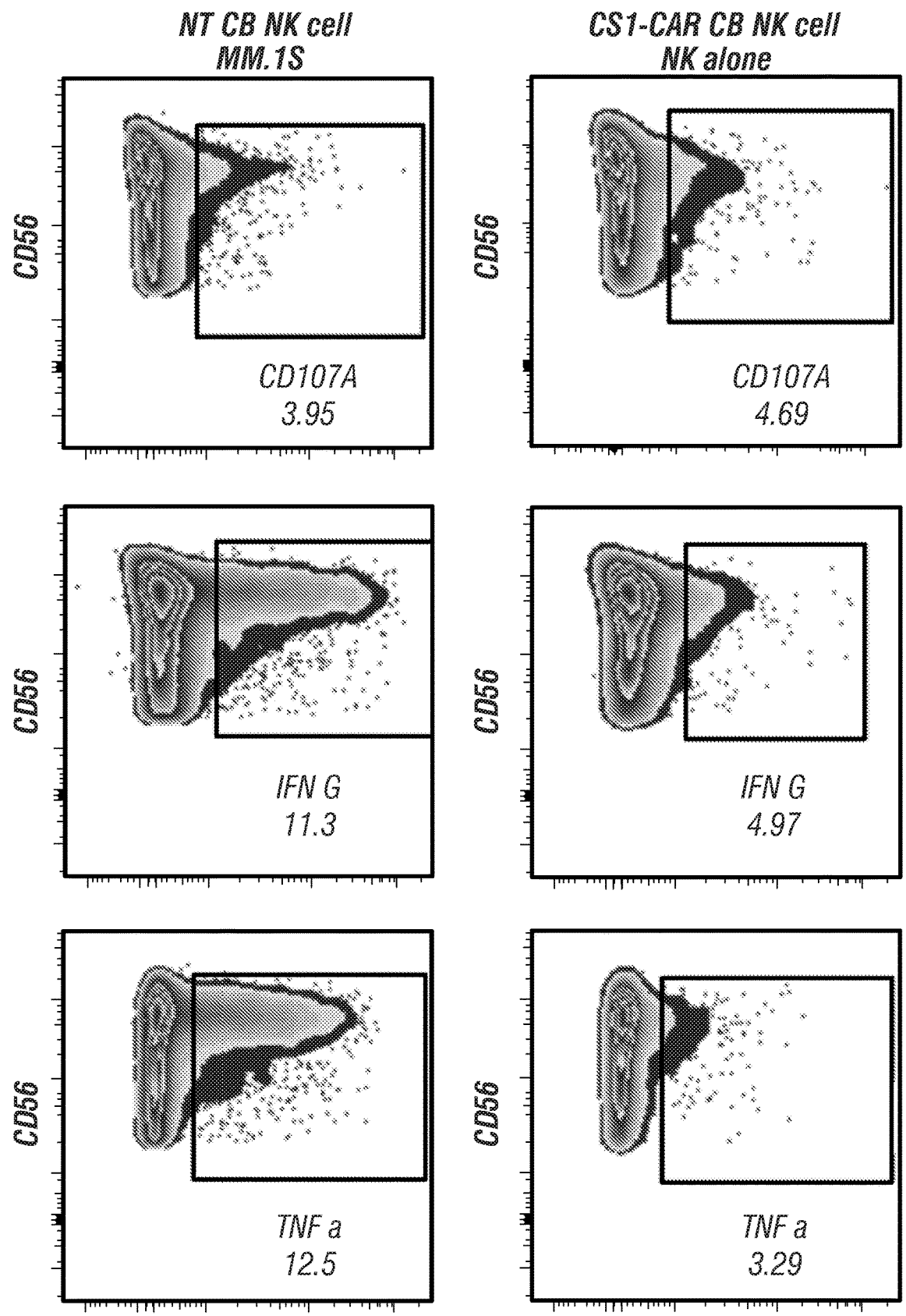
Figure 1C:
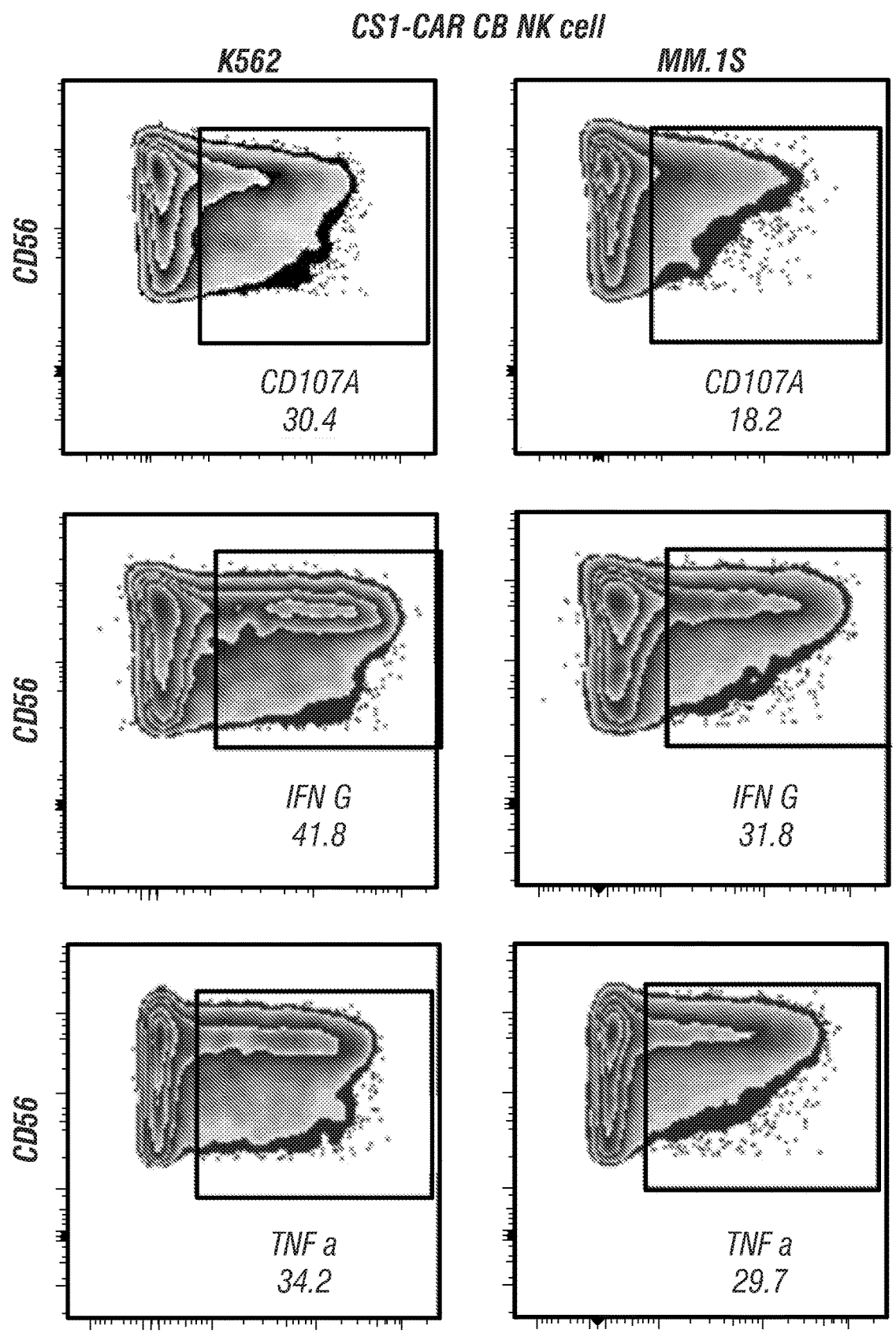

NK cells were derived from cord blood and their specificity was redirected by genetically engineering them to express tumor-specific chimeric antigen receptors (CARs) that could enhance their anti-tumor activity without increasing the risk of graft-versus-host disease (GVHD), thus providing an 'off-the-shelf' source of cells for therapy, such as immunotherapy of any cancer expressing the target. For genetic modification, CB-NK cells were transduced with a retroviral construct (iC9/CAR.CS1/IL-15) to redirect their specificity to recognize the tumor antigen CS1 and target myeloma. The transduction efficiency of the CB-NK cells transduced with the retroviral vector was monitored and transgene expression was found to be stable. The transduction efficiency of CAR expression in NK cells from 2 different donors is shown in FIG. 1A. The transduced NK cells were observed to exert superior killing of CS1-expressing myeloma cell lines (FIG. 1A) and to produce more effector cytokines in response to CS1-expressing myeloma cells lines (FIG. 1C).

Figure 2A:
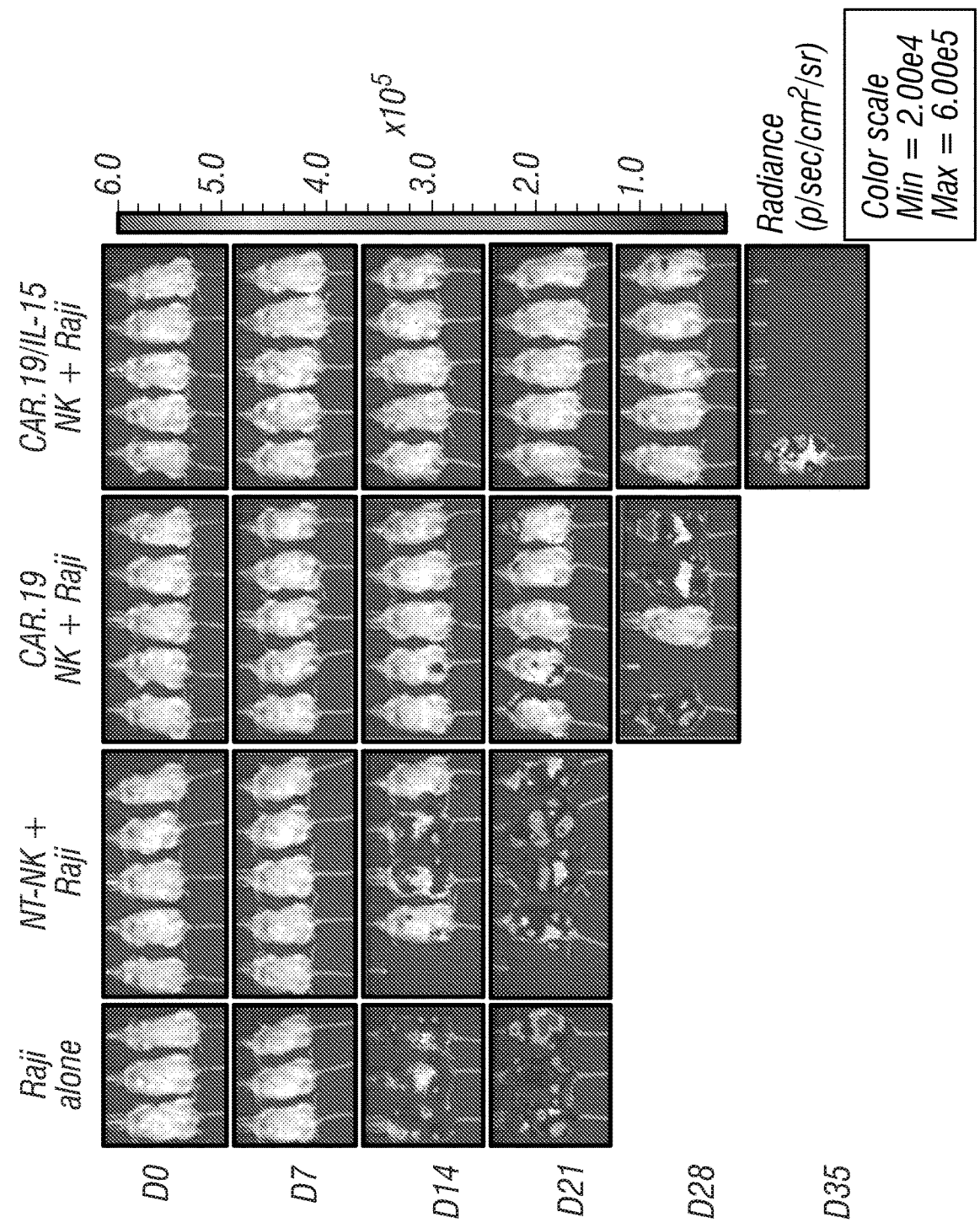
FIGS. 2A-2B: IL-15 enhances NK-CAR mediated killing of tumor (FIG. 2A) and prolongs survival (FIG. 2B).
Figure 2B:
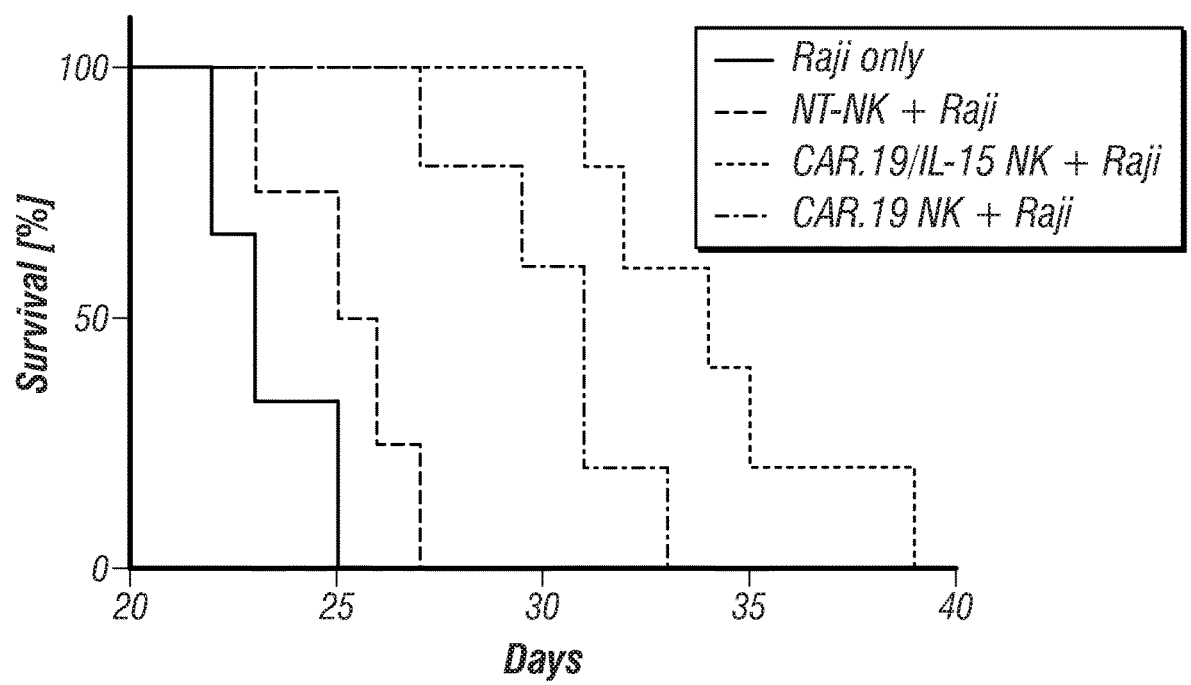

To determine the anti-leukemic effect of the CAR-transduced NK cells, they were infused into a "humanized" mouse model of lymphoblastic leukemia, the luciferase-expressing Raji NSG mouse model. To monitor the trafficking of CAR-CD19l+CB-NK cells to tumor sites in vivo, the cells were labeled with the FFLuc vector, enabling monitoring by bioluminescence imaging. Engrafted mice received CS1$^+$ Raji leukemic B cells ($2\times10^6$) injected intravenously and labeled with the RLuc vector to monitor tumor growth. Six to 10 days after tumor engraftment, mice were infused intravenously with $2\times10^7$ expanded CB-NK cells that were unmodified or CD19-CD28-zeta-2A-IL15 CB-NK cells labeled with FFLuc. All imaging was performed once a week for 3 weeks. Four groups of animals (n=10 per group) were studied, and the spleens, blood and lymph nodes of the mice were collected after they were euthanized. The CAR-transduced cells resulted in strong anti-tumor response, as evidenced by in vivo bioluminescence imaging. The IL-15 was observed to increase the NK-CAR mediated killing of tumors and prolong survival (FIGS. 2A-2B).

Because of concerns over autonomous, uncontrolled NK-cell growth due to autocrine production of IL-15, a suicide gene based on the inducible caspase-9 (IC9) gene was incorporated into the construct. To test the inducible caspase-9 suicide gene that was incorporated into the retroviral vector, 10 nM of CID AP20187 was added to cultures of iC9/CS1/IL15+NK cells. The AP20187 induced apoptosis/necrosis of transgenic cells within 4 hours as assessed by annexin-V-7AAD staining.

Example 2—Knockout of Glucocorticoid Receptor

Figure 3:
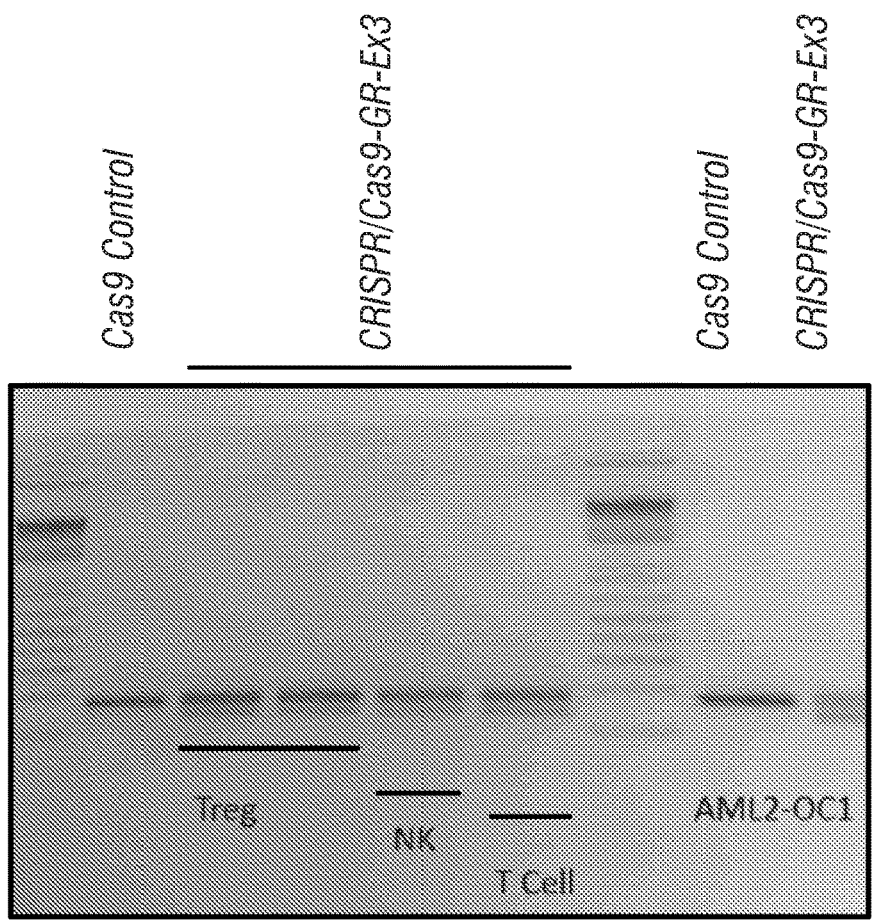
FIG. 3: PCR based screening of glucocorticoid receptor (GR) knockout in hematopoietic cells.

To produce steroid-resistant immune cells, the CRISPR-CAS9 system was used to knockout glucocorticoid receptor in hematopoietic cells using gRNA SEQ ID NOs:1-2. PCR based screening of the glucocorticoid receptor knockout showed efficient knockdown in T cells and NK cells (FIG. 3).

Figure 4A:
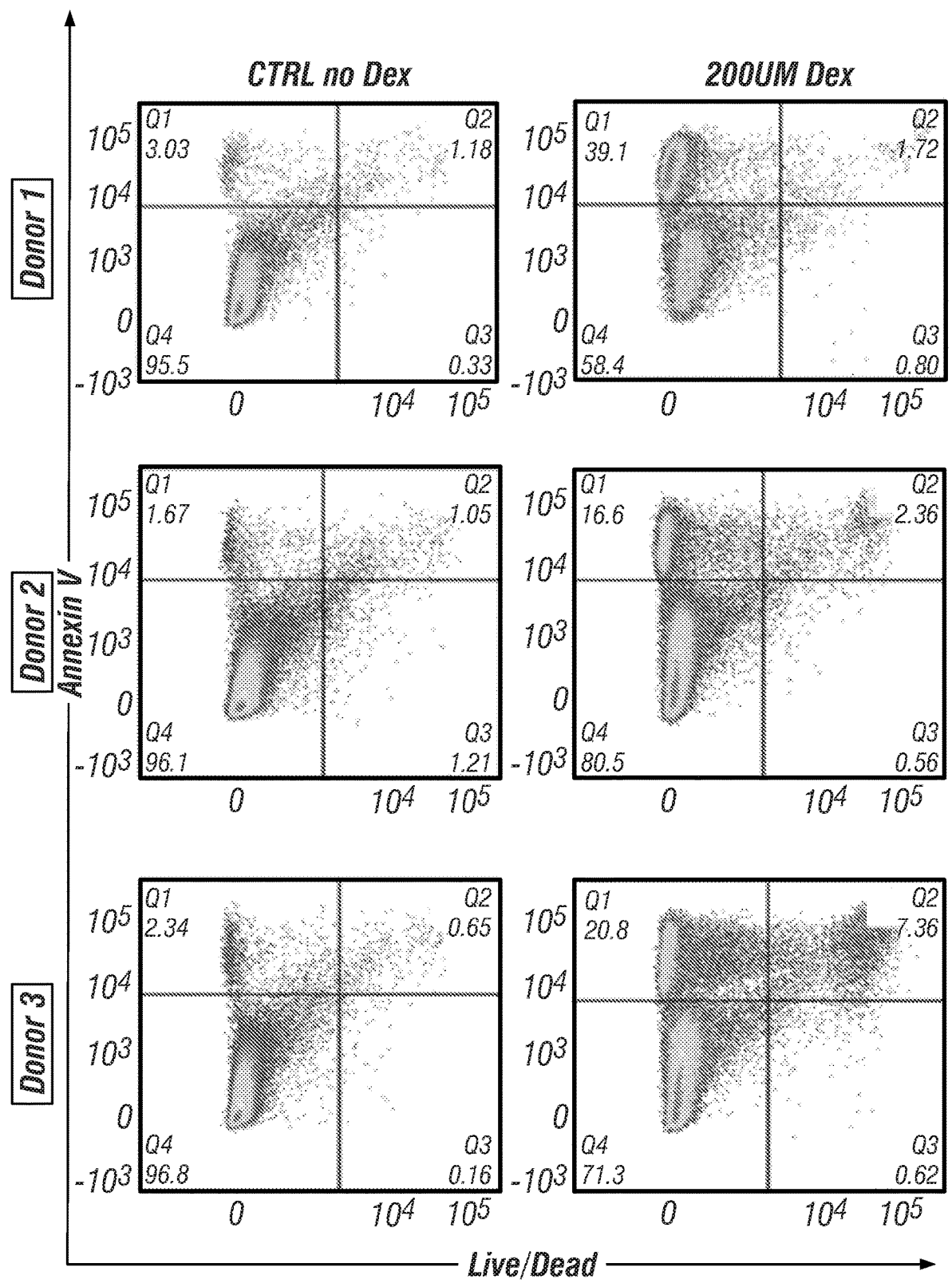
FIGS. 4A-4B: NK cells are sensitive to dexamethasone killing.
Figure 4A:
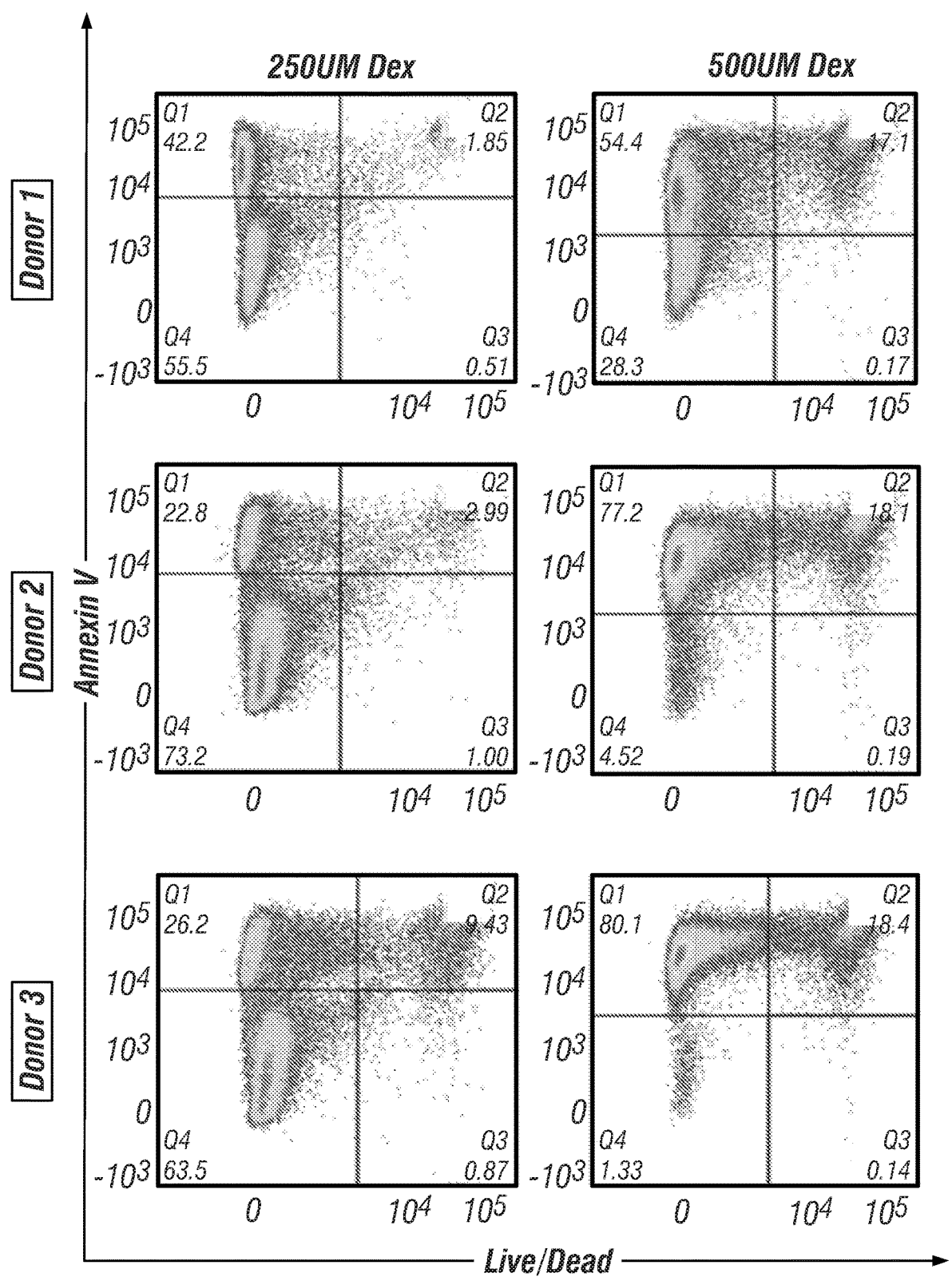
Figure 4B:
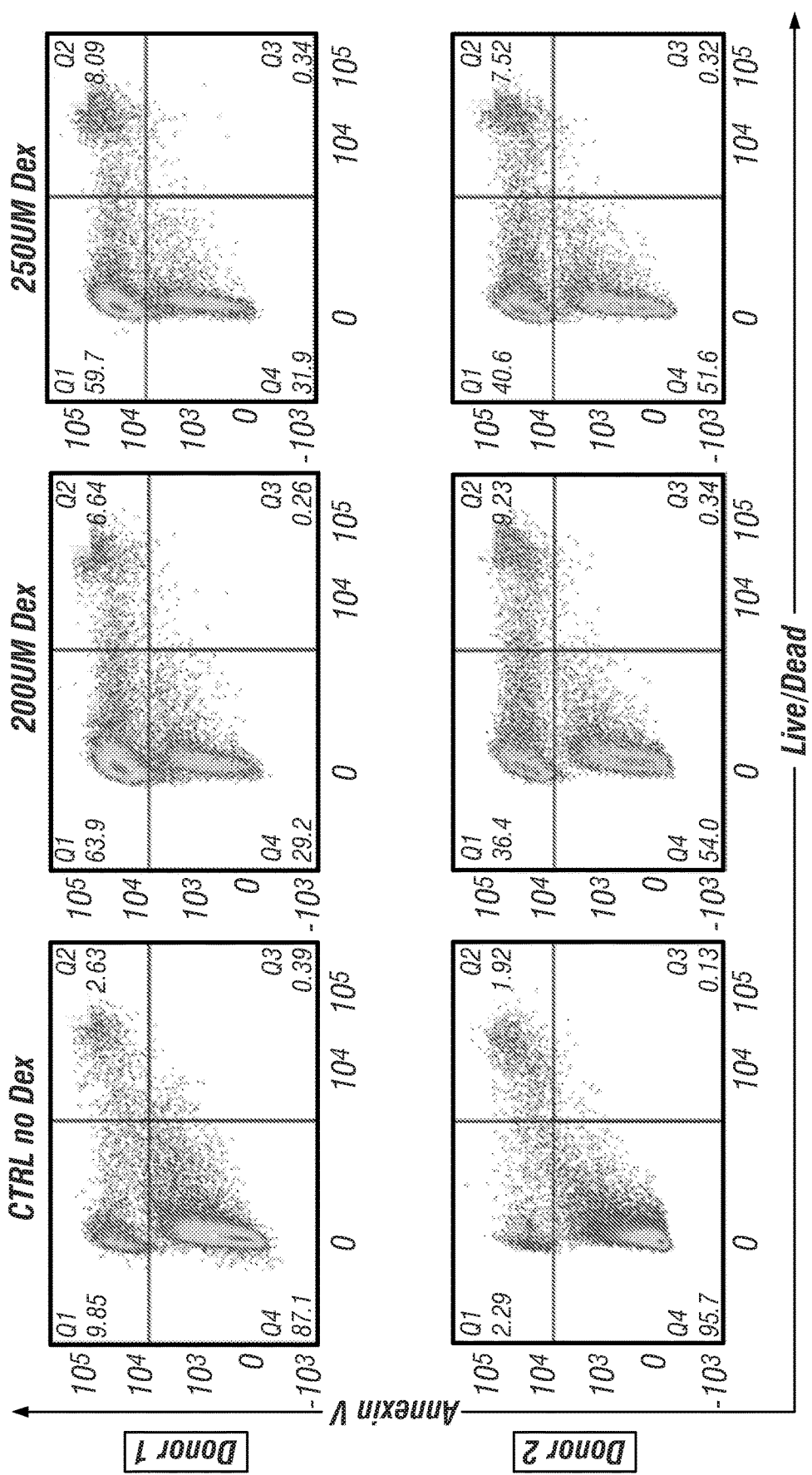
Figure 4B:
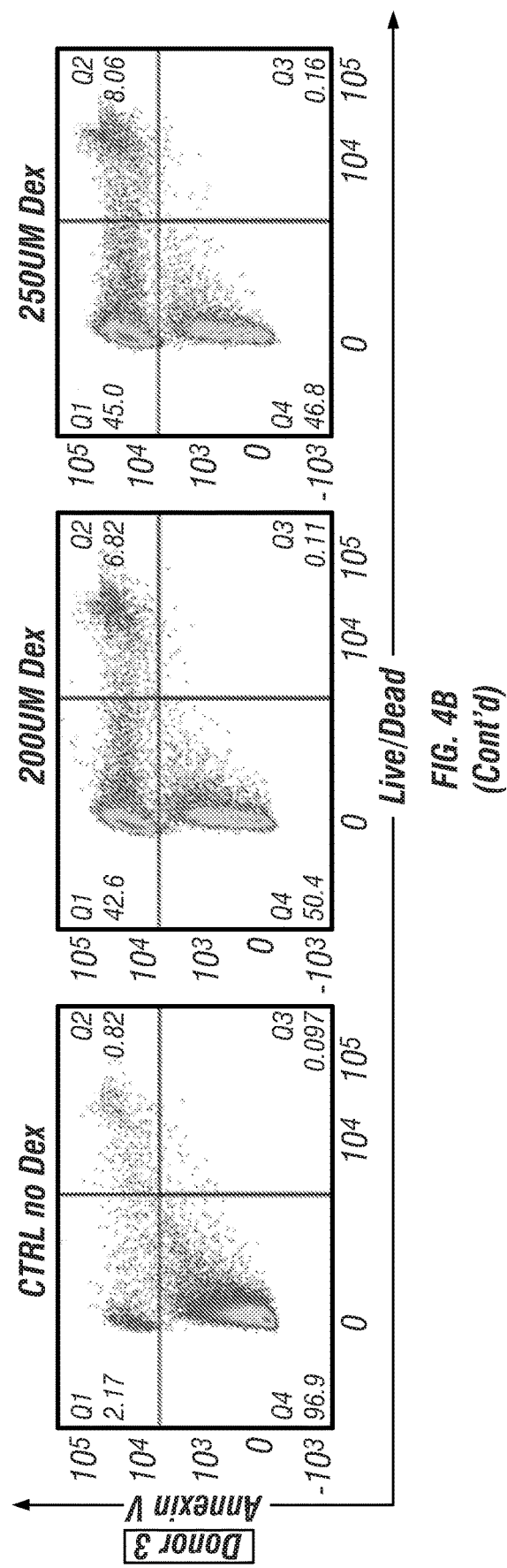
Figure 5:
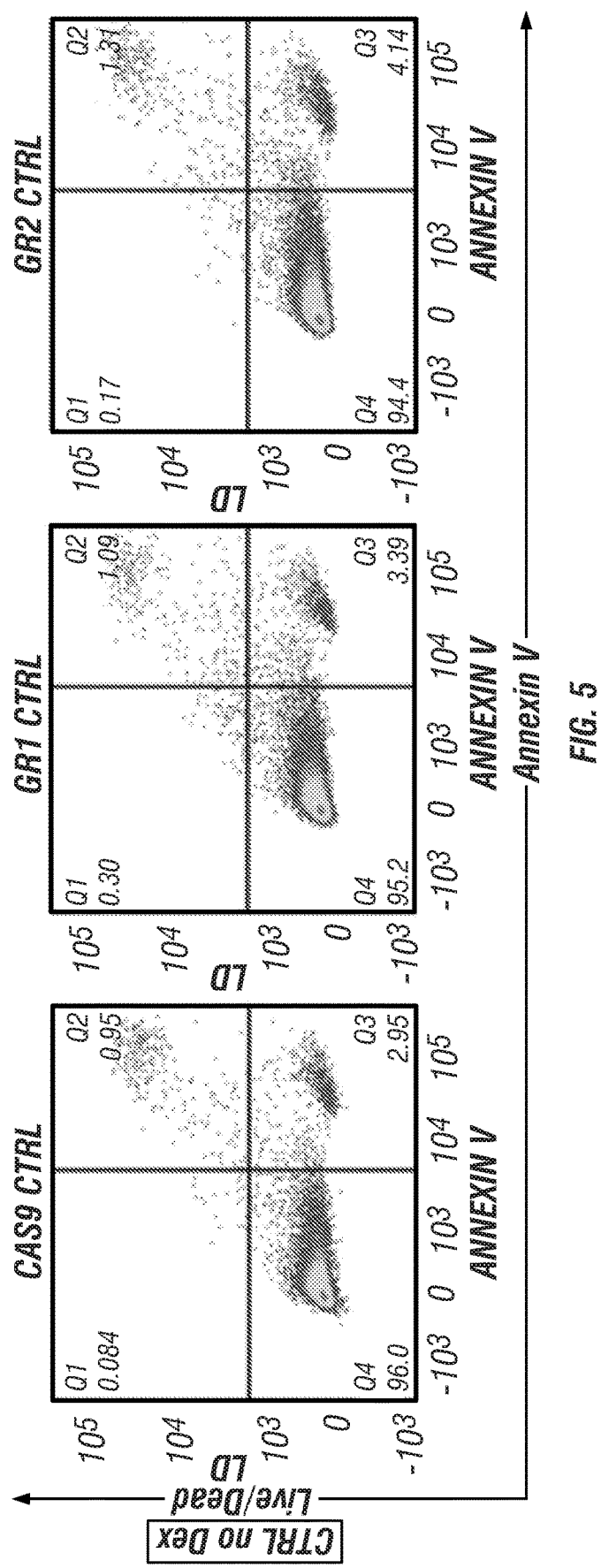
FIG. 5: GR knockout in CAR NK cells protects against dexamethasone killing. Annexin V staining of CAR NK controls cells or cells with GR knockout treated with 200 µM dexamethasone for 12 hours.
Figure 5:
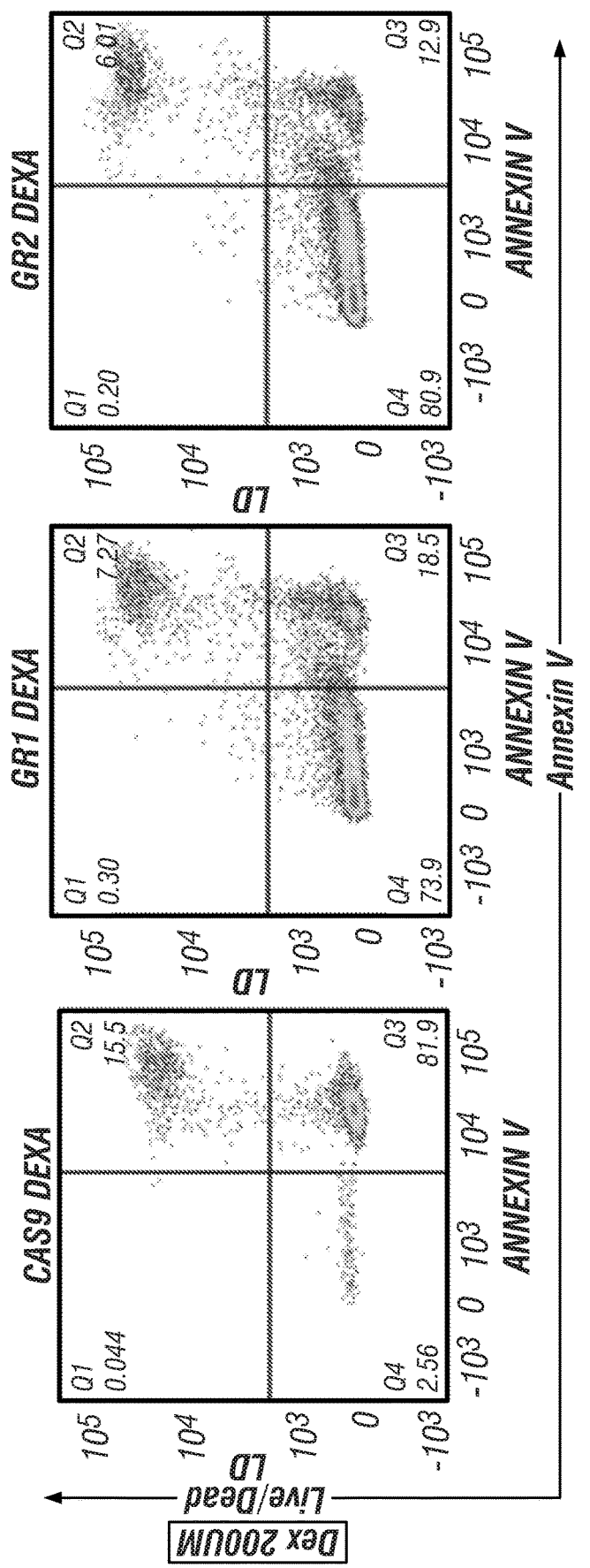

CAR-transduced NK cells were obtained from 3 different donors and assessed for their sensitivity to dexamethasone killing. After 4 and 24 hours of treatment at different doses of dexamethasone, Annexin V staining was performed to assess cell death. NK cells from all 3 donors were found to be sensitive to dexamethasone and at 24 hours of 500 µM dexamethasone treatment all cells were dead (FIGS. 4A-4B). GR knockout in CAR NK cells was found to protect against dexamethasone killing. Annexin V staining of CAR NK controls cells or cells with GR knockout treated with 200 µM dexamethasone for 12 hours is shown in FIG. 5. NK cells with GR knockout were found to be significantly resistant to dexamethasone killing as compared to the control NK cells (FIG. 5). Thus, GR knockout using the CRISPR-CAS9 system was able to generate steroid-resistant NK cells.

Example 3—Knockout of TGFβ-RII in Immune Cells

Figure 6A:
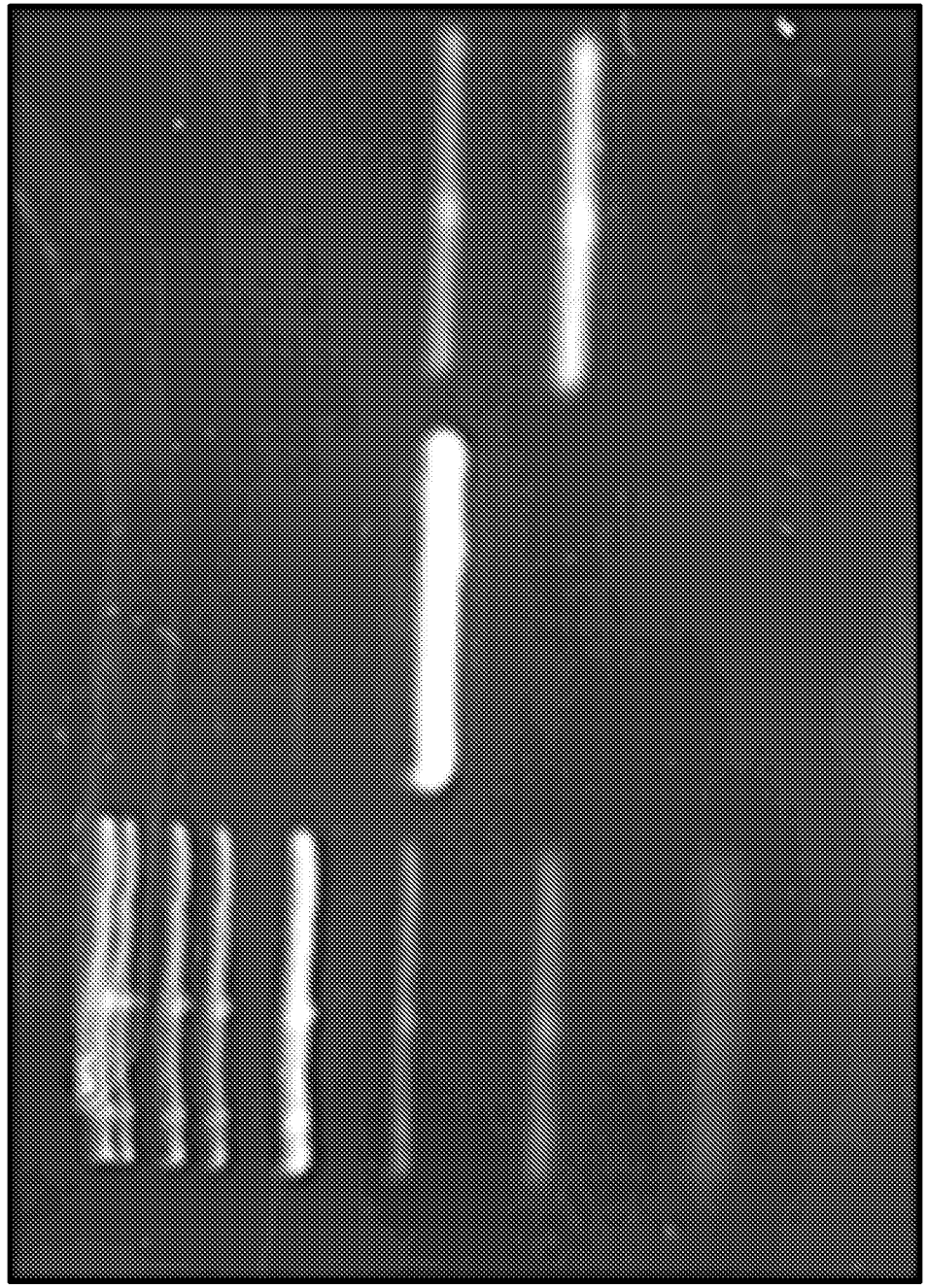
FIGS. 6A-6C: TFGβ CRISPR-mediated knockout renders CAR NK cells resistant to immunosuppressive effect of exogenous TGFβ.
Figure 6B:
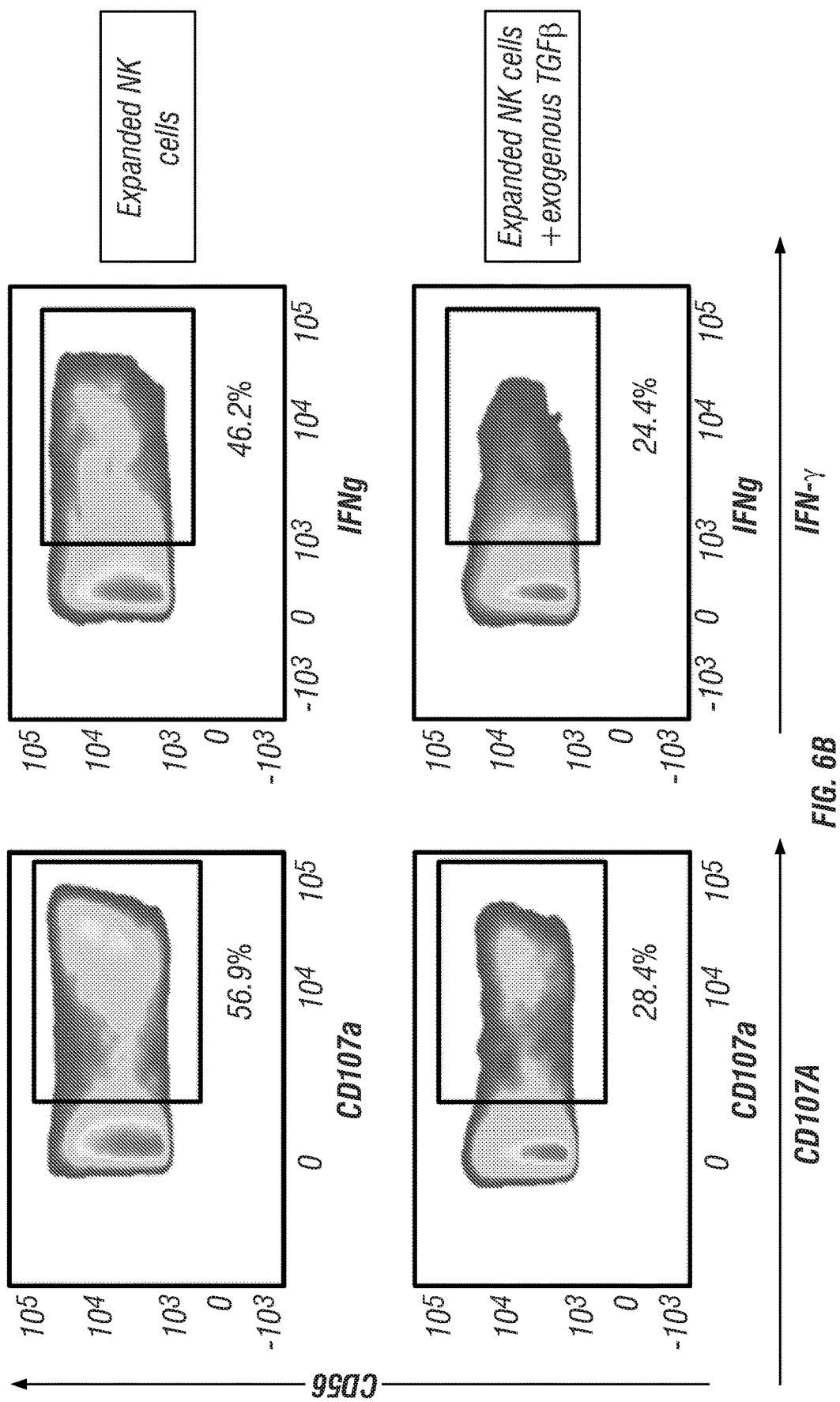
Figure 6B:
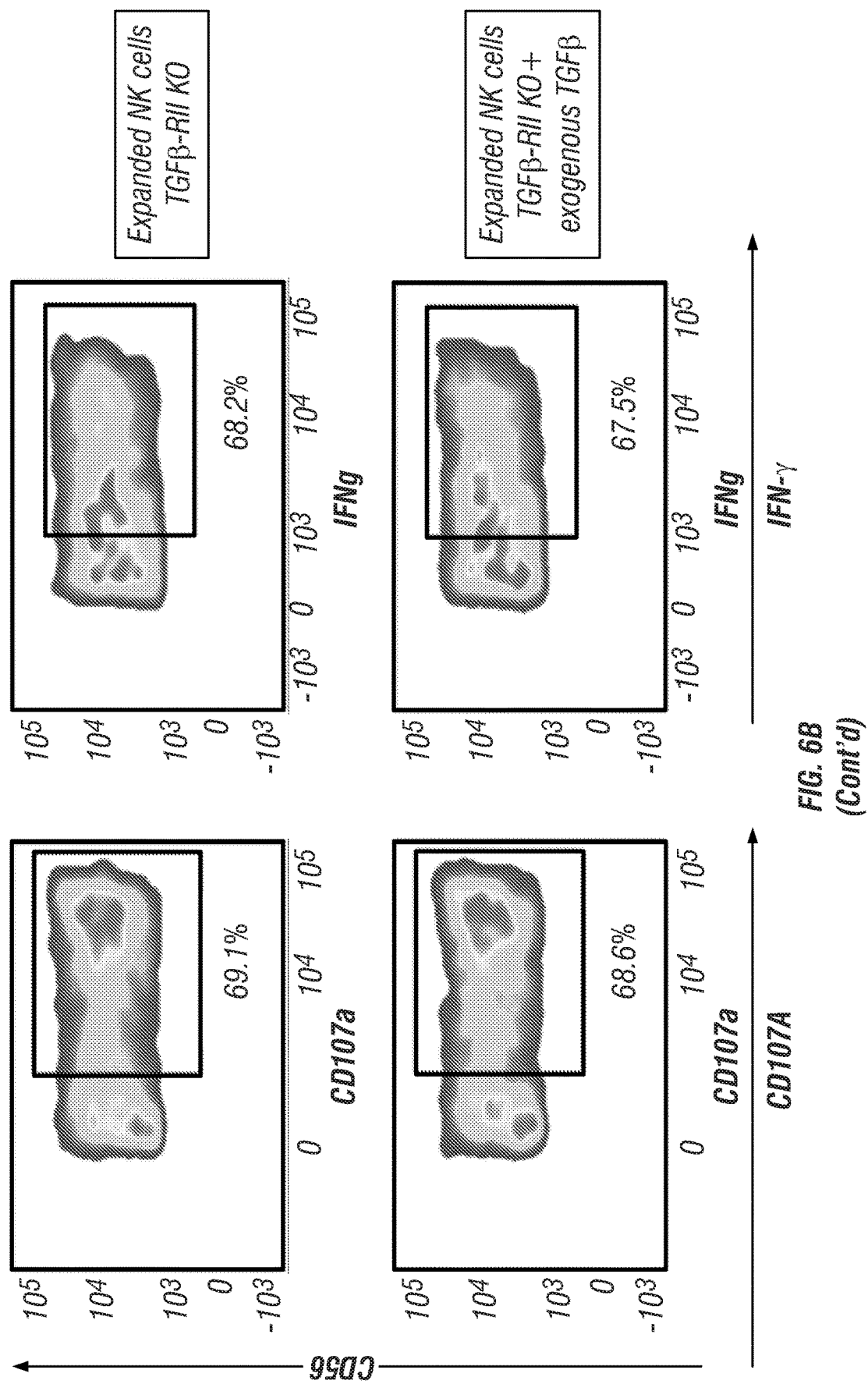
Figure 6C:
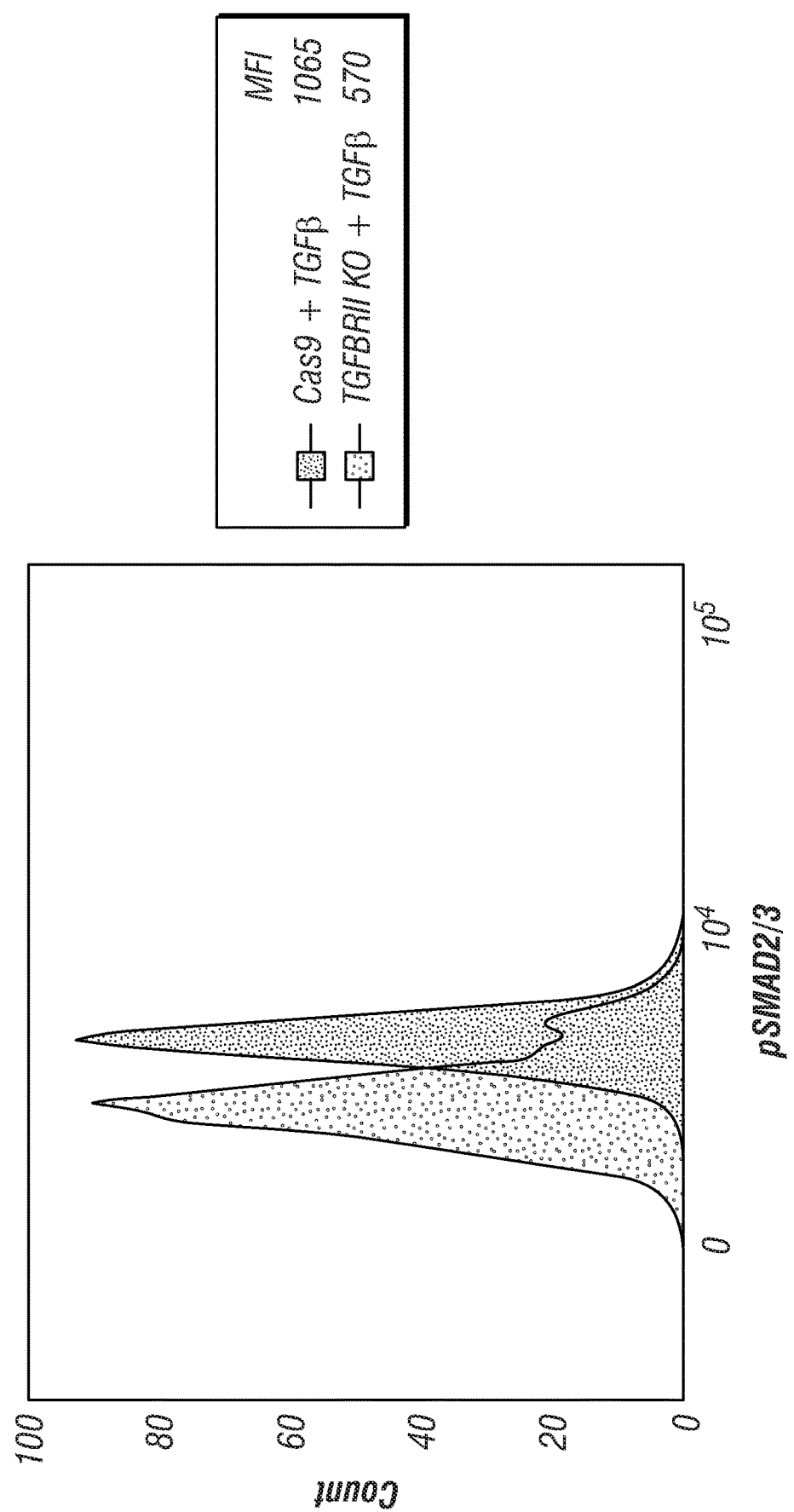

Next, CRISPR-CAS9 was used to knockout TGFβ in CAR NK cells to render CAR NK cells resistant to the immunosuppressive effect of exogenous TGFβ. (FIG. 6A) Successful knockout of TGFβ-RII was achieved using CRISPR/CAS9 technology (Cas9 plus gRNA targeting of Exon 3 of TGFβ-RII using gRNA SEQ ID NOs:3-4) (FIG. 6A). Wild type and TGF-β-RII knockout NK cells were treated with 10 ng/ml of recombinant TGF-β for 48 hrs and their response to K562 targets was assessed. TGF-3-RII knockout NK cells were found to be resistant to the immunosuppressive effect of exogenous TGF-β (FIG. 6B). TGFβ-RII knockout by CRISPR/CAS9 technology was also found to abrogate downstream Smad-2/3 phosphorylation in response to 10n g/ml of recombinant TGF-β compared to NK cells treated with CAS9 alone (FIG. 6C). Thus, CRISPR-CAS9-mediated knockout of TGFβ-RII renders NK cells resistant to TGFβ.

Example 4—Immune Cells Engineered to Express Multiple Antigen Receptors

Immune cells, such as T cells or NK cells, are derived from blood, such as cord blood, and genetically engineered to express tumor-specific antigen receptors, such as CARs and/or TCRs (FIGS. 7A-7D). For genetic modification, the cells are transduced with a retroviral construct (FIG. 7D) to redirect their specificity to recognize two or more tumor antigens. The transduction efficiency and transgene expression are monitored. In addition, the efficacy of the immune cells at killing of antigen-specific target cells is measured by cytotoxicity assays.

To determine the anti-cancer effect of the receptor-transduced immune cells, there are infused into a mouse model of cancer. The cells are labeled with a detectable moiety for monitoring in vivo, such as by bioluminescence imaging. Engrafted mice receive antigen-specific target cells (e.g., $2\times10^6$) injected intravenously and labeled with a vector, such as an RLuc vector, to monitor tumor growth. After tumor engraftment, mice are infused intravenously with expanded transduced immune cells that are unmodified or express the antigen receptors. The animal are monitored, such as by imaging once a week for 3 weeks. The spleens, blood and lymph nodes of the mice are collected after they are euthanized.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Austin-Ward and Villaseca, *Revista Medica de Chile*, 126 (7):838-845, 1998.
Ausubel et al., *Current Protocols in Molecular Biology*, Greene Publishing Associates and John Wiley & Sons, N Y, 1994.
Bennekov et al., *Mt. Sinai J. Med.* 71 (2): 86-93, 2004.
Bukowski et al., *Clinical Cancer Res.*, 4(10):2337-2347, 1998.
Camacho et al. *J Clin Oncology* 22(145): Abstract No. 2505 (antibody CP-675206), 2004.
Campbell, *Curr. Top. Microbiol. Immunol.*, 298: 23-57, 2006.
Chothia et al., *EMBO J.* 7:3745, 1988.
Christodoulides et al., *Microbiology*, 144(Pt 11):3027-3037, 1998.
Cohen et al. *J Immunol.* 175:5799-5808, 2005.
Davidson et al., *J. Immunother.*, 21(5):389-398, 1998.
Davila et al. *PLoS ONE* 8(4): e61338, 2013.
Doulatov et al., *Cell Stem Cell.* 10:120-36, 2012.
European patent application number EP2537416
Fedorov et al., *Sci. Transl. Medicine*, 5(215), 2013.
Frolet et al., *BMC Microbiol.* 10:190 (2010).
Gaj et al., *Trends in Biotechnology* 31(7), 397-405, 2013.
Hanibuchi et al., *Int. J. Cancer*, 78(4):480-485, 1998.
Heemskerk et al. *Hum Gene Ther.* 19:496-510, 2008.
Hellstrand et al., *Acta Oncologica*, 37(4):347-353, 1998.
Hollander, *Front. Immun.*, 3:3, 2012.
Hubert et al., *Proc. Natl. Acad. Sci. USA* 96 14523-28, 1999.
Hui and Hashimoto, *Infection Immun.*, 66(11):5329-5336, 1998.
Hurwitz et al. *Proc Natl Acad Sci USA* 95(17): 10067-10071, 1998.
International Patent Publication No. WO 00/37504
International Patent Publication No. WO 01/14424
International Patent Publication No. WO 2007/069666
International Patent Publication No. WO 2007/069666
International Patent Publication No. WO 98/42752
International Patent Publication No. WO/2014055668
International Patent Publication No. WO1995001994
International Patent Publication No. WO1998042752
International Patent Publication No. WO2000037504
International Patent Publication No. WO200014257
International Patent Publication No. WO2001014424
International Patent Publication No. WO2006/121168
International Patent Publication No. WO2007/103009
International Patent Publication No. WO2009/101611
International Patent Publication No. WO2009/114335
International Patent Publication No. WO2010/027827
International Patent Publication No. WO2011/066342
International Patent Publication No. WO2012/129514
International Patent Publication No. WO2013/071154
International Patent Publication No. WO2013/123061
International Patent Publication No. WO2013/166321
International Patent Publication No. WO2013126726
International Patent Publication No. WO2014/055668
International Patent Publication No. WO2014031687
International Patent Publication No. WO2015016718
International Patent Publication No. WO99/40188
Janeway et al, Immunobiology: The Immune System in Health and Disease, $3^{rd}$ Ed., *Current Biology* Publications, p. 433, 1997.
Johnson et al. *Blood* 114:535-46, 2009.
Jores et al., *PNAS U.S.A.* 87:9138, 1990.
Kim et al., *Nature Biotechnology* 31, 251-258, 2013.
Kirchmaier and Sugden, *J. Virol.*, 72(6):4657-4666, 1998.
Leal, M., *Ann N Y Acad Sci* 1321, 41-54, 2014.
Lefranc et al., *Dev. Comp. Immunol.* 27:55, 2003.
Li et al. *Nat Biotechnol.* 23:349-354, 2005.
Li et al. *Proc. Natl. Acad. Sci. USA* 89:4275-4279, 1992.
Linnemann, C. et al. *Nat Med* 21, 81-85, 2015.
Lockey et al., *Front. Biosci.* 13:5916-27, 2008.
Loewendorf et al., *J. Intern. Med.* 267(5):483-501, 2010.
Ludwig et al. *Nature Biotech.*, (2):185-187, 2006a.
Ludwig et al. *Nature Methods*, 3(8):637-646, 2006b.
Marschall et al., *Future Microbiol.* 4:731-42, 2009.
Mokyr et al. *Cancer Res* 58:5301-5304, 1998.
Notta et al., *Science*, 218-221, 2011.
Pardoll, *Nat Rev Cancer*, 12(4): 252-64, 2012
Parkhurst et al. *Clin Cancer Res.* 15: 169-180, 2009.
Qin et al., *Proc. Natl. Acad. Sci. USA*, 95(24):14411-14416, 1998.
Rieder et al., *J. Interferon Cytokine Res.* (9):499-509, 2009.
Rykman, et al., *J. Virol.* 80(2):710-22, 2006.
Sadelain et al., *Cancer Discov.* 3(4): 388-398, 2013.
Sambrook et al., *Molecular Cloning: A Laboratory Manual*, $3^{rd}$ ed., Cold Spring Harbor Press, Cold Spring Harbor, N.Y. 2001.
Shah et al., *PLoS One*, 8:e776781, 2013.
Singh et al., *Cancer Research*, 68:2961-2971, 2008.
Singh et al., *Cancer Research*, 71:3516-3527, 2011.
Takahashi et al., *Cell*, 126(4):663-76, 2007.
Terakura et al. *Blood.* 1:72-82, 2012.
Turtle et al., *Curr. Opin. Immunol.*, 24(5): 633-39, 2012.
U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,885,796
U.S. Pat. No. 5,994,136
U.S. Pat. No. 6,013,516
U.S. Pat. No. 6,103,470
U.S. Pat. No. 6,207,156
U.S. Pat. No. 6,225,042
U.S. Pat. No. 6,355,479
U.S. Pat. No. 6,362,001
U.S. Pat. No. 6,410,319
U.S. Pat. No. 6,416,998
U.S. Pat. No. 6,544,518
U.S. Pat. No. 6,790,662
U.S. Pat. No. 7,109,304
U.S. Pat. No. 7,442,548
U.S. Pat. No. 7,446,190
U.S. Pat. No. 7,598,364
U.S. Pat. No. 7,989,425
U.S. Pat. No. 8,008,449

U.S. Pat. No. 8,017,114
U.S. Pat. No. 8,058,065
U.S. Pat. No. 8,071,369
U.S. Pat. No. 8,119,129
U.S. Pat. No. 8,129,187
U.S. Pat. No. 8,183,038
U.S. Pat. No. 8,268,620
U.S. Pat. No. 8,329,867
U.S. Pat. No. 8,354,509
U.S. Pat. No. 8,546,140
U.S. Pat. No. 8,691,574
U.S. Pat. No. 8,735,553
U.S. Pat. No. 8,741,648
U.S. Pat. No. 8,900,871
U.S. Pat. No. 9,175,268
U.S. Patent Publication No. 2010/0210014
U.S. patent. Publication Ser. No. 12/478,154
U.S. Patent Publication No. 2002131960
U.S. Patent Publication No. 2003/0211603
U.S. Patent Publication No. 2005/0260186
U.S. Patent Publication No. 2006/0104968
U.S. Patent Publication No. 2009/0004142
U.S. Patent Publication No. 2009/0017000
U.S. Patent Publication No. 2009/0246875
U.S. Patent Publication No. 2011/0104125
U.S. Patent Publication No. 2011/0301073
U.S. Patent Publication No. 20110008369
U.S. Patent Publication No. 2012/0276636
U.S. Patent Publication No. 2013/0315884
U.S. Patent Publication No. 20130149337
U.S. Patent Publication No. 2013287748
U.S. Patent Publication No. 2014/0120622
U.S. Patent Publication No. 2014022021
U.S. Patent Publication No. 20140294898
Varela-Rohena et al. *Nat Med.* 14: 1390-1395, 2008.
Wang et al. *J Immunother.* 35(9):689-701, 2012.
Wu et al., *Adv. Cancer Res.,* 90: 127-56, 2003.
Wu et al., *Cancer,* 18(2): 160-75, 2012.
Yamanaka et al., *Cell,* 131(5):861-72, 2007.
Yu et al., *Science,* 318:1917-1920, 2007.
Zysk et al., *Infect. Immun.* 68(6):3740-43, 2000.

What is claimed is:

1. An immune cell engineered to express human IL-15 (hIL-15) and at least two antigen receptors, wherein the at least two antigen receptors comprise one or more chimeric antigen receptors (CAR) and/or one or more T cell receptors (TCR), wherein the immune cell is engineered to have essentially no expression of glucocorticoid receptor, TGFβ receptor, and/or CISH.

2. The immune cell of claim 1, wherein the immune cell is engineered to express hIL-15, a CAR, and a TCR.

3. The immune cell of claim 1, wherein the immune cell is engineered to express 3, 4, or 5 antigen receptors.

4. The immune cell of claim 1, wherein the immune cell is further defined as a T cell, peripheral blood lymphocyte, NK cell, invariant NK cell, NKT cell, or stem cell.

5. The immune cell of claim 4, wherein the stem cell is a mesenchymal stem cell (MSC) or an induced pluripotent stem (iPS) cell.

6. The immune cell of claim 1, wherein the immune cell is derived from an iPS cell.

7. The immune cell of claim 4, wherein the immune cell is allogeneic or autologous.

8. The immune cell of claim 1, wherein the immune cell is engineered to express one or more additional cytokines.

9. The immune cell of claim 8, wherein the one or more additional cytokines are IL-21 and/or IL-2.

10. The immune cell of claim 1, wherein the immune cell is isolated from peripheral blood, cord blood, or bone marrow.

11. The immune cell of claim 10, wherein the cord blood is pooled from 2 or more individual cord blood units.

12. The immune cell of claim 1, wherein the immune cell further expresses a suicide gene.

13. The immune cell of claim 1, wherein the at least two antigen receptors comprise antigen binding regions that bind one or more tumor associated antigens.

14. The immune cell of claim 13, wherein the tumor associated antigens are CD19, CD319/CS1, ROR1, CD20, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, WT-1, EGFRvIII, TRAIL/DR4, and/or VEGFR2.

15. The immune cell of claim 1, wherein an antigen binding region of a first antigen receptor is distinct from an antigen binding region of a second antigen receptor.

16. The immune cell of claim 14, wherein the antigen binding region of the first antigen receptor binds to a first antigen and the antigen binding region of the second antigen receptor binds to a second antigen.

17. The immune cell of claim 16, wherein:
(a) the first antigen is EGFRvIII and the second antigen is NY-ESO;
(b) the first antigen is HER2/Neu and the second antigen is MUC-1;
(c) the first antigen is CA-125 and the second antigen is MUC-1;
(d) the first antigen is CA-125 and the second antigen is WT-1;
(e) the first antigen is EGFRvIII and the second antigen is Mage-A3, Mage-A4, or Mage-A10;
(f) the first antigen is EGFRvIII and the second antigen is TRAIL/DR4;
(g) the first antigen is CEA-CAR and the second antigen is Mage-A3-TCR, Mage-A4-TCR or Mage-A10; or
(h) the first antigen is HER2/Neu, CEA-CAR, and/or CA-125, EGFRvIII and the second antigen is MUC-1, WT-1, TRAIL/DR4Mage-A3-TCR, Mage-A4-TCR and/or Mage-A10.

18. A pharmaceutical composition comprising an effective amount of an immune cell of claim 1.

19. A composition comprising an effective amount of an immune cell of an immune cell of claim 1 for the treatment of an immune-related disorder in a subject.

20. A method of treating an immune-related disorder in a subject comprising administering an effective amount of immune cells of claim 1 to the subject.

21. The method of claim 20, wherein the immune-related disorder is a cancer, autoimmune disorder, graft versus host disease, allograft rejection, or inflammatory condition.

22. The method of claim 20, wherein the immune-related disorder is an inflammatory condition and the immune cells have essentially no expression of glucocorticoid receptor.

23. The method of claim 22, wherein the subject has been or is being administered a steroid therapy.

24. The method of claim 20, wherein the immune-related disorder is a cancer.

25. The method of claim 24, wherein the cancer is:
(a) ovarian cancer and the immune cells have antigenic specificity for MUC-1, CA-125, and/or WT-1;
(b) lung cancer and the immune cells have antigenic specificity for NY-ESO, EGFR-vIII, Mage-A3, Mage-A4, Mage-A10, and/or TRAIL/DR4;
(c) pancreatic cancer or colon cancer and the immune cells have antigenic specificity for Mage-A3, Mage-A4, Mage-A10, and/or CEA;
(d) breast cancer and the immune cells have antigenic specificity for MUC-1 and HER2/Neu;
(e) glioblastoma and the immune cells have antigenic specificity for Mage-A3, Mage-A4, Mage-A10v, and/or EGFRvIII;
(f) sarcoma and the immune cells have antigenic specificity for NY-ESO and EGFR-vIII.

\* \* \* \* \*

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Ex3 NR3C1 sG1

<400> SEQUENCE: 1
tgctgttgag gagctgga                                                        18

<210> SEQ ID NO 2
<211> LENGTH: 18
<212> TYPE: DNA
<213> ORGANISM: Artificial Sequence
<220> FEATURE:
<223> OTHER INFORMATION: Ex3 NR3C1 sG2

<400> SEQUENCE: 2
agcacaccag gcagagtt                                                        18

<210> SEQ ID NO 3
<211> LENGTH: 18
<212> TYPE: DNA
<213> ORGANISM: Artificial Sequence
<220> FEATURE:
<223> OTHER INFORMATION: EX3 TGFBR2 sG1

<400> SEQUENCE: 3
cggctgagga gcggaaga                                                        18

<210> SEQ ID NO 4
<211> LENGTH: 18
<212> TYPE: DNA
<213> ORGANISM: Artificial Sequence
<220> FEATURE:
<223> OTHER INFORMATION: EX3 TGFBR2 sG2

<400> SEQUENCE: 4
tggaggtgag caatcccc                                                        18

<210> SEQ ID NO 5
```

```
<211> LENGTH: 20
<212> TYPE: DNA
<213> ORGANISM: Artificial Sequence
<220> FEATURE:
<223> OTHER INFORMATION: Overlap sequence

<400> SEQUENCE: 5
ttaatacgac tcactatagg                                              20

<210> SEQ ID NO 6
<211> LENGTH: 20
<212> TYPE: DNA
<213> ORGANISM: Artificial Sequence
<220> FEATURE:
<223> OTHER INFORMATION: Overlap sequence

<400> SEQUENCE: 6
gttttagagc tagaaatagc                                              20
```